US008314283B2

(12) United States Patent
Kingsford et al.

(10) Patent No.: US 8,314,283 B2
(45) Date of Patent: Nov. 20, 2012

(54) MEDICAL WRAPS

(75) Inventors: Howard A. Kingsford, Amherst, NH (US); Holly Isabelle, Deerfield, NH (US); George A. Provost, Litchfield, NH (US); William H. Shepard, Amherst, NH (US)

(73) Assignee: Velcro Industries B.V., Willemstad, Curacao ( * ) Notice: Subject to any disclaimer, the term of this patent is extended or adjusted under 35 U.S.C. 154(b) by 1789 days.

(21) Appl. No.: 10/738,847

(22) Filed: Dec. 16, 2003

(65) Prior Publication Data

US 2004/0167456 A1 Aug. 26, 2004

Related U.S. Application Data

(60) Provisional application No. 60/434,085, filed on Dec. 16, 2002, provisional application No. 60/494,653, filed on Aug. 12, 2003.

(51) Int. Cl.
*A61F 13/00* (2006.01)
*A61F 7/00* (2006.01)

(52) U.S. Cl. ........................................ 602/41; 607/108

(58) Field of Classification Search .................. 602/1, 2, 602/41, 42, 60–62, 75, 76; 607/108–112
See application file for complete search history.

(56) References Cited

U.S. PATENT DOCUMENTS

| | | | |
|---|---|---|---|
| 3,000,384 | A | 9/1961 | Piers, Jr. |
| 3,086,529 | A | 4/1963 | Munz et al. |
| 3,203,551 | A | 8/1965 | Loan |
| 3,255,749 | A | 6/1966 | Smithers |
| 3,279,008 | A | 10/1966 | Wallach |
| 3,426,363 | A | 2/1969 | Girard |
| 3,474,171 | A | 10/1969 | Scharpf |
| 3,947,927 | A | 4/1976 | Rosenthal |
| 3,955,728 | A | 5/1976 | Jackson et al. |
| 3,999,483 | A | 12/1976 | Grundy |
| 4,041,549 | A | 8/1977 | Atkinson |

(Continued)

FOREIGN PATENT DOCUMENTS

| | | |
|---|---|---|
| DE | 299 20 079 | 5/2000 |

(Continued)

OTHER PUBLICATIONS

Written Opinion from International Preliminary Examining Authority.

(Continued)

*Primary Examiner* — Patricia Bianco
*Assistant Examiner* — Tarla Patel
(74) *Attorney, Agent, or Firm* — Fish & Richardson P.C.

(57) ABSTRACT

A medical wrap includes a flexible, sheet-form substrate with a discrete medical function delivery region having a surface adapted to be placed against a patient's skin to provide a desired medical effect. The substrate carries a field of fibers exposed on one side thereof for engagement by fastener elements, and an array of fastener elements extending from a side of the substrate opposite the exposed fibers. The fastener elements each have a respective stem extending integrally from a film of resin disposed in a band across the substrate and encapsulating surface features of the substrate. The fastener elements are constructed to snag the exposed fibers when the substrate is wrapped about a patient in an overlapping manner, to secure the wrap about the patient with the medical function delivery region in a desired position. The wrap is useful as a hot or cold pack, medical dressing or drug delivery device.

40 Claims, 68 Drawing Sheets

U.S. PATENT DOCUMENTS

| | | | | | |
|---|---|---|---|---|---|
| 4,079,767 | A | | 3/1978 | Howard | |
| 4,088,136 | A | | 5/1978 | Hasslinger | |
| 4,213,548 | A | | 7/1980 | Wood | |
| 4,273,130 | A | | 6/1981 | Simpson | |
| 4,280,489 | A | | 7/1981 | Johnson, Jr. | |
| 4,396,013 | A | | 8/1983 | Hasslinger | |
| 4,527,566 | A | * | 7/1985 | Abare | 607/112 |
| 4,548,375 | A | | 10/1985 | Moss | |
| 4,569,348 | A | | 2/1986 | Hasslinger | |
| 4,571,245 | A | | 2/1986 | Hubbard et al. | |
| 4,592,118 | A | | 6/1986 | DeWoskin | |
| 4,628,945 | A | | 12/1986 | Johnson, Jr. | |
| 4,662,037 | A | | 5/1987 | Provost et al. | |
| 4,794,028 | A | | 12/1988 | Fischer | |
| 4,852,778 | A | | 8/1989 | Beiser et al. | |
| 4,893,381 | A | | 1/1990 | Frankel | |
| 4,894,060 | A | | 1/1990 | Nestegard | |
| 4,901,472 | A | * | 2/1990 | Donohue et al. | 47/2 |
| 4,964,402 | A | | 10/1990 | Grim et al. | |
| 4,979,953 | A | | 12/1990 | Spence | |
| 4,999,932 | A | | 3/1991 | Grim | |
| 5,007,416 | A | | 4/1991 | Burns et al. | |
| 5,020,711 | A | | 6/1991 | Kelley | |
| 5,027,801 | A | | 7/1991 | Grim | |
| 5,031,607 | A | | 7/1991 | Peters | |
| 5,078,128 | A | | 1/1992 | Grim et al. | |
| 5,088,478 | A | | 2/1992 | Grim | |
| 5,088,487 | A | * | 2/1992 | Turner | 607/108 |
| 5,101,830 | A | | 4/1992 | Duffy | |
| 5,113,877 | A | | 5/1992 | Johnson, Jr. et al. | |
| 5,125,400 | A | | 6/1992 | Johnson, Jr. | |
| 5,172,980 | A | | 12/1992 | Provost | |
| 5,193,549 | A | | 3/1993 | Bellin et al. | |
| 5,240,159 | A | | 8/1993 | Gregory | |
| 5,260,015 | A | | 11/1993 | Kennedy et al. | |
| 5,316,547 | A | | 5/1994 | Gildersleeve | |
| 5,348,530 | A | | 9/1994 | Grim et al. | |
| 5,353,525 | A | | 10/1994 | Grim | |
| 5,366,439 | A | | 11/1994 | Peters | |
| 5,368,549 | A | | 11/1994 | McVicker | |
| 5,378,224 | A | | 1/1995 | Billotti | |
| 5,392,782 | A | | 2/1995 | Garrett | |
| 5,396,894 | A | | 3/1995 | Eide et al. | |
| 5,403,413 | A | | 4/1995 | Masuda | |
| 5,407,421 | A | | 4/1995 | Goldsmith | |
| 5,409,500 | A | | 4/1995 | Dyrek | |
| 5,415,625 | A | | 5/1995 | Cassford et al. | |
| 5,441,687 | A | | 8/1995 | Murasaki et al. | |
| 5,464,385 | A | | 11/1995 | Grim | |
| RE35,113 | E | | 12/1995 | Grim | |
| 5,511,552 | A | | 4/1996 | Johnson | |
| 5,520,622 | A | | 5/1996 | Bastyr et al. | |
| 5,527,267 | A | | 6/1996 | Billotti | |
| 5,551,496 | A | | 9/1996 | Gray, Jr. | |
| 5,570,824 | A | | 11/1996 | Lyon et al. | |
| 5,582,584 | A | | 12/1996 | Billotti | |
| 5,595,069 | A | | 1/1997 | Gies | |
| 5,614,057 | A | | 3/1997 | Conley, Jr. et al. | |
| 5,662,599 | A | | 9/1997 | Reich | |
| 5,678,558 | A | | 10/1997 | Johnson | |
| 5,700,257 | A | | 12/1997 | Minick et al. | |
| 5,700,340 | A | | 12/1997 | Johnson | |
| 5,785,673 | A | | 7/1998 | Billotti | |
| 5,800,372 | A | | 9/1998 | Bell et al. | |
| 5,843,018 | A | | 12/1998 | Shesol et al. | |
| 5,857,220 | A | | 1/1999 | Erny et al. | |
| 5,865,821 | A | | 2/1999 | Lowey | |
| 5,900,350 | A | | 5/1999 | Provost et al. | |
| 5,911,612 | A | | 6/1999 | Steger | |
| 5,967,308 | A | | 10/1999 | Bowen | |
| 6,017,072 | A | | 1/2000 | Grant | |
| 6,036,718 | A | | 3/2000 | Ledford et al. | |
| 6,040,493 | A | | 3/2000 | Cooke et al. | |
| 6,054,091 | A | | 4/2000 | Miller et al. | |
| 6,055,668 | A | | 5/2000 | Gros et al. | |
| 6,080,347 | A | | 6/2000 | Goulait | |
| 6,093,202 | A | | 7/2000 | Dyken et al. | |
| 6,115,891 | A | | 9/2000 | Suenaga et al. | |
| 6,163,939 | A | | 12/2000 | Lacey et al. | |
| 6,202,260 | B1 | | 3/2001 | Clune et al. | 24/30.5 R |
| 6,210,389 | B1 | * | 4/2001 | Long et al. | 604/391 |
| 6,233,945 | B1 | * | 5/2001 | Kohout | 62/4 |
| 6,248,419 | B1 | | 6/2001 | Kennedy et al. | |
| 6,251,131 | B1 | | 6/2001 | Kohout | |
| RE37,338 | E | | 8/2001 | McVicker | |
| 6,290,662 | B1 | | 9/2001 | Morris et al. | |
| 6,306,112 | B2 | | 10/2001 | Bird | |
| 6,310,036 | B1 | | 10/2001 | Browdie | |
| 6,320,095 | B1 | | 11/2001 | Wall | |
| 6,342,285 | B1 | | 1/2002 | Shepard et al. | |
| 6,393,843 | B2 | | 5/2002 | Kohout | |
| 6,409,691 | B1 | | 6/2002 | Dakin et al. | |
| 6,409,748 | B1 | | 6/2002 | DeCarlo et al. | |
| 6,432,125 | B2 | | 8/2002 | Kohout | |
| 6,438,965 | B1 | | 8/2002 | Liao | |
| 6,440,159 | B1 | | 8/2002 | Edwards et al. | |
| 6,460,541 | B1 | | 10/2002 | Shah et al. | |
| 6,719,711 | B1 | | 4/2004 | Islava | |
| 6,936,018 | B2 | * | 8/2005 | Chalek | 602/2 |
| 6,955,847 | B1 | | 10/2005 | Itou et al. | |
| 2002/0022108 | A1 | | 2/2002 | Krantz et al. | |

FOREIGN PATENT DOCUMENTS

| | | |
|---|---|---|
| WO | WO 91/07151 | 5/1991 |
| WO | WO98/02120 | 1/1998 |
| WO | WO 00/03667 | 1/2000 |
| WO | WO 00/27721 | 5/2000 |
| WO | WO00/27721 | 5/2000 |
| WO | WO 01/67911 | 9/2001 |
| WO | WO 02/38096 | 5/2002 |

OTHER PUBLICATIONS

Communication from a foreign patent office in a counterpart application (PCT IPER).

* cited by examiner

MEDICAL WRAPS

CROSS-REFERENCE TO RELATED APPLICATIONS

This application claims the benefit of the filing dates or U.S. Provisional Applications Nos. 60/434,085 and 60/494,653, filed Dec. 16, 2002 and Aug. 12, 2003, respectively, and the contents of these prior applications are incorporated herein by reference in their entirety.

TECHNICAL FIELD

This invention relates to conformable, self-securing wrappings that provide therapy, treatment, and other medical functions, and to methods to manufacture and use of such wrappings.

BACKGROUND

Medical wraps or wrappings are employed to wrap about portions of the human or animal body for medical treatment. Well-known examples include elongated bandages. However, some medical wraps provide functions in addition to serving as bindings. For example, some wraps structurally support and stabilize broken or sprained limbs and joints. Others are employed to hold hot packs or cold packs up against the skin.

SUMMARY OF THE INVENTION

Conformable, self-securing function-delivery wrapping products are fabricated from running length unions of molded and other mass-produced surface fastener materials combined with synthetic resin sheet or film. Among effective low-cost wrappings provided are products intended to be wrapped about the body or its major extremities for athletic, medical and veterinary use, for instance to deliver cold and hot therapy, enable drug delivery, and facilitate measuring and monitoring functions.

We use the term “surface fasteners” to refer to fasteners such as hook and loop fasteners in which molded hook elements, such as single hook shapes, mushroom shapes, palm tree shapes or of other shapes, releasably engage in loop elements as provided by low-cost non-woven or light-weight knit materials. The term “surface fasteners” as used here also refers to so-called “self-engaging” fasteners that have fastener elements of one or more kinds that engage with like fasteners on another surface and to fastener surfaces of materials that are adhesive or cohesive or otherwise engage with one another by action of overlying surfaces.

In preferred embodiments, surface fasteners, such as male fastening elements or fastener element preforms, are continuously produced either at the time of the union or as preformed material. In instances in which a surface fastener comprises hooks or at least their stems, these are preferably formed in mold cavities of a mold roll and a plastic sheet or flange is simultaneously formed to enable union with other components of the composite.

The preformed web material may also advantageously be a structural member of the wrapping, or a material defining or helping to define the function-delivery section of the wrapping. In other examples, a web element, for instance preformed plastic sheet or a non-woven material, that is to form part of the wrapping, by heat and pressure acting on deformable resin, is joined to another preformed material which may be a fastener or function-delivery component. In many preferred cases the pressure for the union is provided by a continuously turning pressure roll.

In cases where a wrapping is constructed for medical or veterinarian use, the function to be performed with respect to a living body may include conditioning, therapy, pain relief, detection, monitoring, measuring and diagnosis. For instance, the wrapping may apply thermal treatment or thermal therapy, either as a hot pack, cold pack, warm pack, or thermoelectric unit; it may apply a therapeutic, imaging, measuring or monitoring instrument to the body; it may apply pressure for support or measurement; it may apply a therapeutic agent, such as application of a transdermal medication under warm conditions enhancing permeation of the skin, or it may apply medication suitable for skin, wounds, or incisions, etc.

In one aspect, the invention features a method of treating living tissue, the method including providing a wrap that includes a flexible, sheet-form substrate having a field of fibers exposed on one side thereof for engagement by fastener elements. The substrate also includes an array of fastener elements extending from a side of the substrate opposite the exposed fibers, the fastener elements each having a respective stem extending integrally from a film of resin disposed in a band across the substrate, the substrate including a pouch in a discrete medical function delivery region adapted to be placed against living tissue to provide a desired medical effect. The method also includes wrapping the wrap about living tissue, with the medical function delivery region placed to provide treatment to the tissue, and engaging the field of fibers with the fastener elements to secure the wrap about the tissue.

In some cases, the pouch is disposed at one end of the substrate and the method includes placing the function delivery region against the tissue to be treated before wrapping the wrap about the tissue. In some cases, the function delivery region includes a wound covering and the treatment includes wound protection and fluid absorption. For example, the pouch may contain a dressing sponge or other absorbent material.

In some cases, the pouch contains a material substantially colder than the tissue to be treated, for removing heat from the tissue. In some cases, the pouch contains a material substantially warmer than the tissue to be treated, for heating the tissue. In some cases, the wrap is constructed to apply pressure against the tissue when the substrate is wrapped about the tissue and over the pouch under tension.

In some cases, the fastener elements are disposed in a discrete region adjacent to an end of the substrate. For example, the fastener elements may be disposed adjacent to an end of the substrate furthest from the pouch. For some applications, the substrate includes a non-fastening, graspable end region extending beyond the region of fastener elements.

In some cases, the substrate is resiliently stretchable in a direction extending between the function delivery region and the array of fastener elements, and the method includes resiliently stretching the substrate during wrapping and before engaging the field of fibers with the fastener elements. The longitudinal resiliency of the substrate can help maintain a shear loading on the fastening elements as wrapped, and pressure against the tissue.

In some cases, the wrap is of a length sized to enable wrapping the wrap about an extremity, torso, or head of a human being or animal in an overlapped condition, the tissue comprising human or animal tissue. For example, the tissue may of a human finger, the method including wrapping the wrap about both the finger and an adjacent finger to constrain movement of the wrapped fingers.

In some cases, the pouch contains a functional agent in an inactivated state, the method including activating the functional agent to begin treatment. For example, the functional agent may include unmixed ingredients that, when activated by mixing, generate an endothermic reaction, or an ingredient that, when activated by exposure to air, generates an exothermic reaction.

Particularly for applications in which the underlying tissue is tender or damaged, the fastener elements and field of fibers are advantageously configured to enable removal of the wrap from the tissue by application of a peeling force of less than about 0.2 pound of force per transverse inch of engaged width of the engaged fastener elements, or more preferably less than about 0.1 pound of force per transverse inch of engaged width, to limit tissue trauma during wrap removal. By "transverse inch of engaged width of the engaged fastener elements" we mean the effective width of engagement of the fasteners, perpendicular to the applied peel load, across which the engaged fasteners develop a peel resisting force. For configurations in which multiple, parallel strips of fasteners extend along the peel direction, the engaged width is the sum of the engaged widths of each of the fastener strips, for example.

In some embodiments, the function delivery region contains a medicament for medical treatment of the tissue.

In some cases, the wrap is in an unused state as provided, the method further includes, after medical treatment, removing the wrap from the tissue and disposing of the removed wrap as waste.

In some cases, the tissue is of a tree or other vegetation.

In another aspect, the invention features a medical wrap that includes a flexible, sheet-form substrate carrying a field of fibers exposed on one side thereof for engagement by fastener elements, and an array of fastener elements extending from a side of the substrate opposite the exposed fibers, the fastener elements each having a respective stem extending integrally from a film of resin disposed in a band across the substrate and encapsulating surface features of the substrate, the fastener elements constructed to snag the exposed fibers when the substrate is wrapped about the living tissue in an overlapping manner, to secure the wrap about the tissue. The wrap defines a pouch in a discrete medical function delivery region adapted to be placed against living tissue to provide a desired medical effect.

In some cases, the function delivery region is disposed at one end of the substrate.

In some embodiments, the medical wrap is contained in a sealed package with the substrate wrapped about the end at which the pouch is disposed, with the fastener elements releasably snagging fibers of the substrate to hold the substrate in a wrapped condition.

For some applications, the function delivery region includes a wound covering. For example, the pouch may contain a dressing sponge or other absorbent material, such as a combine dressing.

In some cases, the pouch contains a material substantially colder than normal human body temperature, for removing heat from human tissue. In some other cases, the pouch contains a material substantially warmer than normal human body temperature, for heating human tissue. In some cases, the wrap is constructed to apply pressure against the tissue when the substrate is wrapped about the tissue and over the pouch under tension.

In some cases, the fastener elements are disposed in a discrete region adjacent to an end of the substrate. For example, the fastener elements may be disposed adjacent to an end of the substrate furthest from the function delivery region. For some uses, the substrate includes a non-fastening, graspable end region extending beyond the region of fastener elements.

In some cases, the substrate is resiliently stretchable in a direction extending between the function delivery region and the array of fastener elements. In some cases, the medical wrap is of a length sized to enable wrapping the wrap about an extremity, torso, or head of a human being or animal in an overlapped condition.

In some cases, the pouch contains a functional agent in an inactivated state. For example, the functional agent may includes unmixed ingredients that, when activated by mixing, generate an endothermic reaction, or an ingredient that, when activated by exposure to air, generates an exothermic reaction.

In some cases, the fastener elements and field of fibers are configured to enable removal of the wrap from the tissue by application of a peeling force of less than about 0.2 pound of force per transverse inch of engaged width of the engaged fastener elements, to limit tissue trauma during wrap removal. For some uses, the peeling force is less than about 0.1 pound of force per transverse inch of engaged width.

In another aspect, the invention features a method of forming medical wraps for delivering medical functions, the method including introducing a sheet-form, flexible substrate into a gap defined by a mold roll and an opposed cooperating member, the mold roll defining an array of blind cavities shaped to form fastener elements or fastener element stems. The method also includes extruding resin into the gap to fill the cavities and commingle with surface features of the substrate, thereby forming a band of resin extending along the substrate, with an array of fastener element stems extending integrally therefrom. The method also includes securing a field of exposed fibers to a surface of the substrate, cutting across the substrate to form individual wraps, each wrap of a length sufficient to extend about a human limb and having a segment of the band of resin extending thereacross; and providing the wrap with a medical function delivery pouch for containing materials selected to provide medical treatment to living tissue when the wrap is wrapped about the tissue.

In some cases, the method further includes, after forming the band of resin, forming engageable heads on the fastener element stems.

In some embodiments, the method further includes inserting an absorbent pad into the pouch.

In some cases, the method further includes inserting an activatable, thermic material into the pouch.

In some cases, providing the pouch comprises attaching a preformed pouch at an end of the substrate, such as by welding material of the pouch to the substrate. For example, the pouch material may be welded to a strip of the extruded resin spaced apart from the band of resin having fastener element stems.

In some other examples, adding the pouch includes forming a pouch from the substrate.

In some constructions, the method further includes heat sealing the substrate to close the pouch with contents in the pouch.

In another aspect, the invention features a medical wrap including a flexible, sheet-form substrate carrying a field of fibers exposed on one side thereof for engagement by fastener elements. The medical wrap also includes an array of fastener elements extending from a side of the substrate opposite the exposed fibers, the fastener elements each having a respective stem extending integrally from a film of resin disposed in a band across the substrate and encapsulating surface features of the substrate, the fastener elements constructed to snag the exposed fibers when the substrate is wrapped about living tissue in an overlapping manner, to secure the wrap about the tissue. The fastener elements and field of fibers are configured to enable removal of the wrap from the tissue by application of a peeling force of less than about 0.2 pound of force per transverse inch of engaged width of the engaged fastener elements, to limit tissue trauma during wrap removal.

Preferably, the peeling force is less than about 0.1 pound of force per transverse inch of engaged width.

Preferably, the fastener elements and field of fibers are configured to resist an applied shear load, along the wrap, of at least 1.0 pound per square inch of engaged fastener area.

Preferably, the medical wrap a total weight of less than about 150 grams per square meter of overall wrap area (more preferably, less than about 120 grams per square meter).

In another aspect, the invention features a thermic treatment wrap that includes a flexible, sheet-form substrate carrying both a field of fibers exposed on one side thereof for engagement by fastener elements, and an array of fastener elements extending from a side of the substrate opposite the exposed fibers adjacent one end of the substrate, the fastener elements each having a respective stem extending integrally from a film of resin disposed in a band across the substrate and encapsulating surface features of the substrate. The wrap defines a pouch containing a material activatable to initiate a thermic reaction, for transferring heat with respect to a patient about which the wrap is wrapped in overlapping manner, with the fastener elements engaging the fibers of the substrate to hold the pouch against the patient.

In some cases, the activatable material produces an endothermic reaction when activated, for removing body heat. In some cases, the activatable material produces an exothermic reaction when activated, for warming the patient. In some cases, the pouch is disposed at one end of the substrate. In some cases, the thermic treatment wrap is contained in a sealed package with the substrate wrapped about the pouch, with the fastener elements releasably snagging fibers of the substrate to hold the substrate in a wrapped condition. In some cases, the substrate has a nominal width shorter than its length, and wherein the pouch is disposed substantially within the width of the substrate, such that the wrap effectively envelops the pouch when wrapped about the patient, to hold the pouch in place.

Another aspect of the invention features a medical wrap comprising a flexible, sheet-form substrate with a discrete medical function delivery region having a surface adapted to be placed against a patient's skin to provide a desired medical effect. The substrate carries a field of fibers exposed on one side thereof for engagement by fastener elements, and an array of fastener elements extending from a side of the substrate opposite the exposed fibers. The fastener elements each have a respective stem extending integrally from a film of resin disposed in a band across the substrate and encapsulating surface features of the substrate, and the fastener elements are constructed to snag the exposed fibers when the substrate is wrapped about a patient in an overlapping manner, to secure the wrap about the patient with the medical function delivery region in a desired position.

In several respects, the invention features medical wraps that can be made so lightweight and inexpensive as to be practically disposable, yet useful for performing critical medical functions. In this sense, their disposability can help to reduce the need for in-field sterilization of such components, and the risk of contamination. By configuring the fasteners to have particularly low peel resistance, the wraps can be removed without significant trauma to underlying tissue, making them particularly useful for wound and burn care. Many practical configurations of the wraps are readily manufacturable in continuous processes on standard bag-making equipment, and integrating the fastener components into the substrate of the wraps can significantly reduce the complexity and assembly costs of the overall products. Moreover, wraps can be produced with particularly low overall weights and material costs.

Details of embodiments are set forth in the accompanying drawings and the description below. Other features, objects, and advantages will be apparent from the description and drawings.

DESCRIPTION OF DRAWINGS

FIG. 1A' is a side view of the wrapping shown in FIG. 1A.

FIG. 1B' is a further magnified view of one useful form of hook.

FIG. 5 is a magnified partial cross-section taken parallel to the axis of the forming roll showing a formation on the mold roll for defining a fold axis.

FIG. 12B is a perspective view of the step of inserting a treated gauze pad into the pouch of the wrapping of FIG. 12A during the process illustrated in FIG. 9A while

FIG. 38 is a perspective view of a wrapping for a tree.

Like reference symbols in the various drawings indicate like elements.

DESCRIPTION OF EMBODIMENTS

Figure 1D:
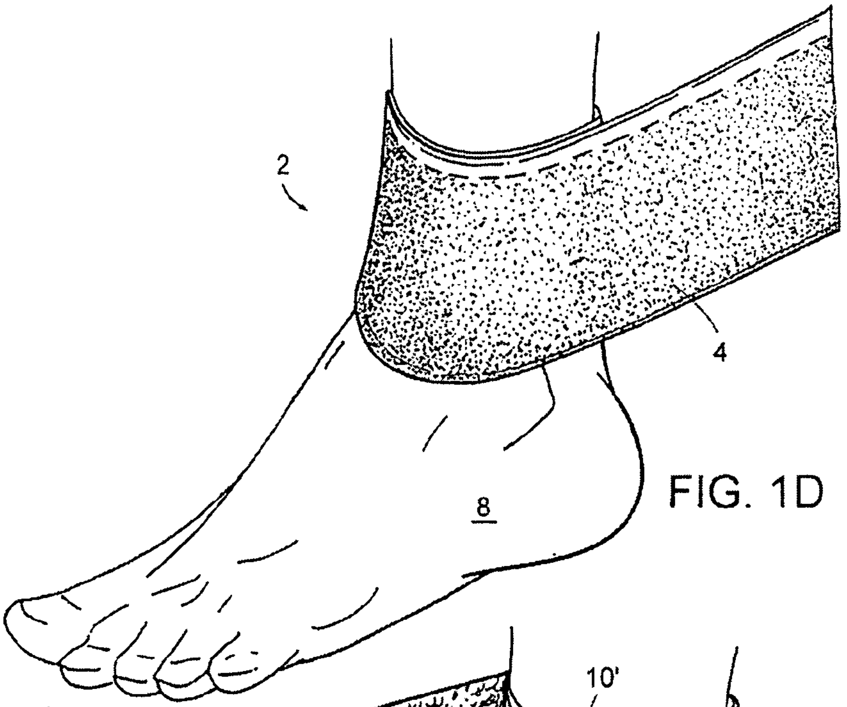
FIG. 1D is a perspective view of the wrapping of FIG. 1A shown more fully wrapped about the ankle.
Figure 1A:
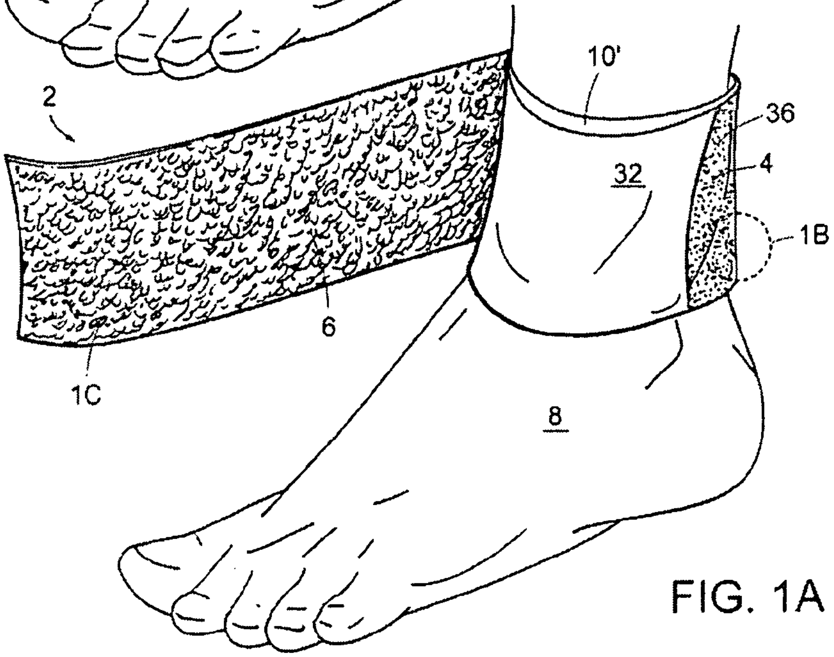
FIG. 1A is a perspective view of a wrapping for a human ankle.
Figure 1A:
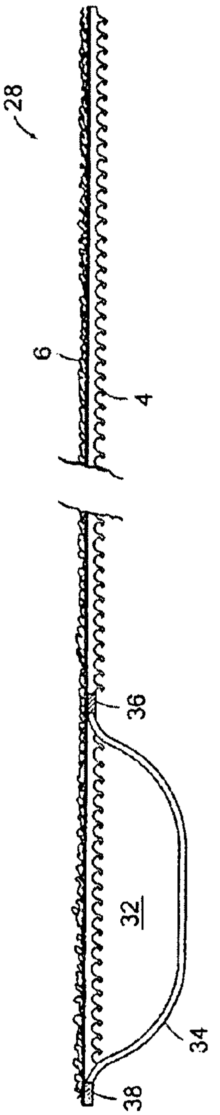
Figure 37:
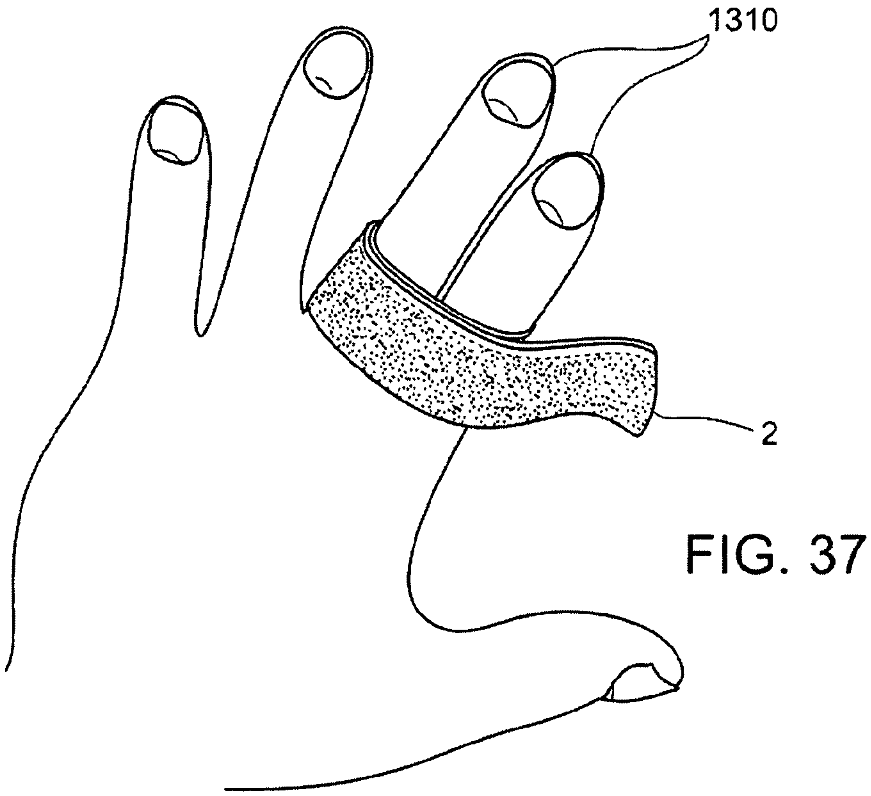
FIG. 37 is a perspective view of a wrapping for human fingers.

A specific product 2, illustrated in FIGS. 1A and 1D, is an extended, flexible, self-securing, function-delivering wrapping having broad fields of engageable hook and loop fasteners 4 and 6, respectively. The product 2 is shown being wrapped about an ankle 8 (or fingers 1310 shown in FIG. 37). The field of loop fasteners 6 disposed on the inside surface is arranged to engage the field of hooks 4 on the outside of the wrapping. The wrapping defines a functional zone 10, which can be held with desired pressure upon an injured region of the ankle by appropriate user-applied tension as the wrapping is applied while the corresponding portion of the field of loops 6 progressively engage upon corresponding portions of the field of hooks. In this case the entire wrapping is secured, with no free end to dangle or be cut away.

Such products are conveniently manufactured by uniting a preformed web of loop material with a running length or lengths of plastic hooks, or hook preforms that are subsequently finished into loop-engageable hooks. Appropriate welds are formed to define the functional region, and the continuous material is cut at a selected repeat length, either to complete the wrapping, or to complete a subassembly of it.

Figure 1B:
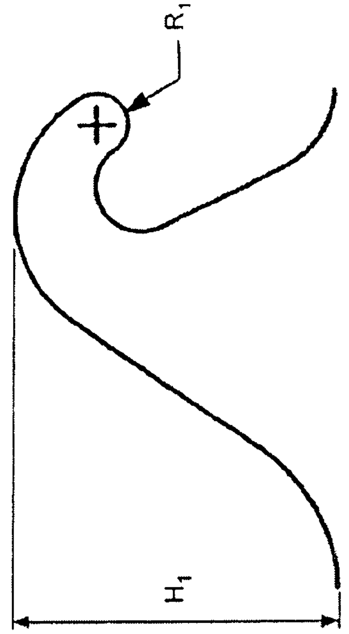
FIG. 1B is a highly magnified diagrammatic view of one embodiment of a hook fastener portion of one side of the wrapping of FIG. 1A.
Figure 1B:
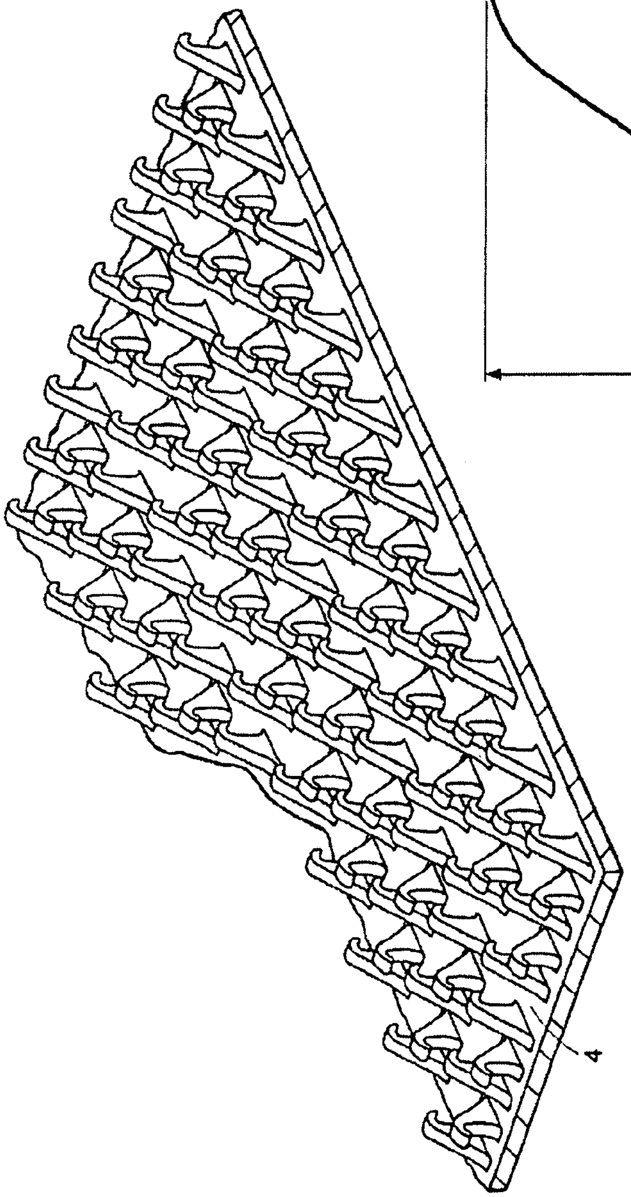
Figure 1C:
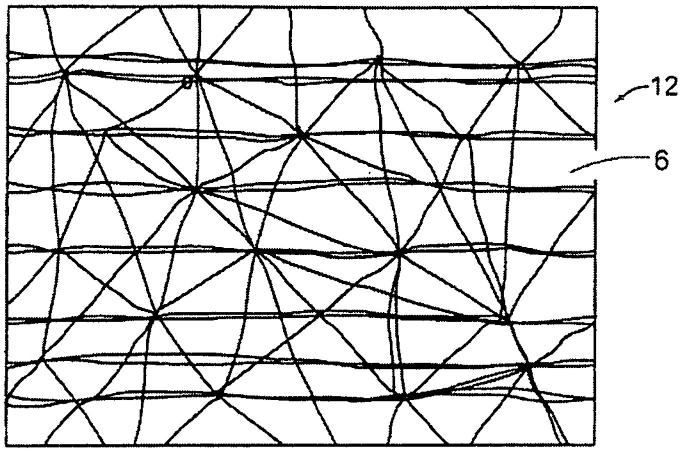
FIGS. 1C and 1C' are magnified diagrammatic and photographic views, respectively, of a non-woven loop fastener material.
Figure 1C:
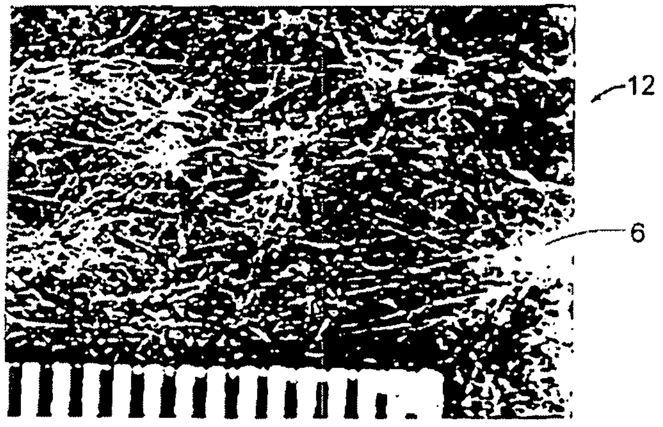

As a specific example, shown by FIG. 1B, the hook fasteners 4 may be of molded form available from Velcro, USA under designation CFM29, shown magnified in FIG. 1B'. Its dimensions are $H_1$ of 0.0149 inch and $R_1$ of 0.0015 inch. As a specific example, referring to magnified FIG. 1C, a loop material 12 may for instance be non-woven hook-engageable material, available from Velcro, USA as loop L3310, shown diagrammatically in FIG. 1C', formed according to techniques shown in U.S. Pat. No. 6,342,285, the full content of which is hereby incorporated by reference. In other cases of hook and loop construction, other low-cost hook forms and loop materials may be employed, for instance hooks formed by post-forming molded stems and loops formed by light weight, inexpensive knit materials, for instance knitted loop material having a weight of less than 4 ounces per square yard, preferably less than 2 ounces per square yard.

In cases where the wrapping 2 is used to apply a wound dressing or other therapy to a wound or tender area, the hooks 4 are designed to peel easily off from the loops 6, yet resist substantial shear loads of at least about 1.0 pound per square inch of engaged fastener area. The particularly low peel resistance, preferably a maximum of about 0.2 pounds of force per transverse inch of engaged width of the engaged hooks and loops, or even lower than about 0.1 pounds of force per transverse inch of engaged width for some applications, allows a paramedic or other user to release the wrapping 2 easily to limit additional trauma and pain to the wound while removing the functional area 10 from the wound or tender tissue. This preferable low peel design of the hooks 4 and the loops 6 also applies to other embodiments of wound and therapeutic wrappings described below.

Figures 1E, 1F, 1G:
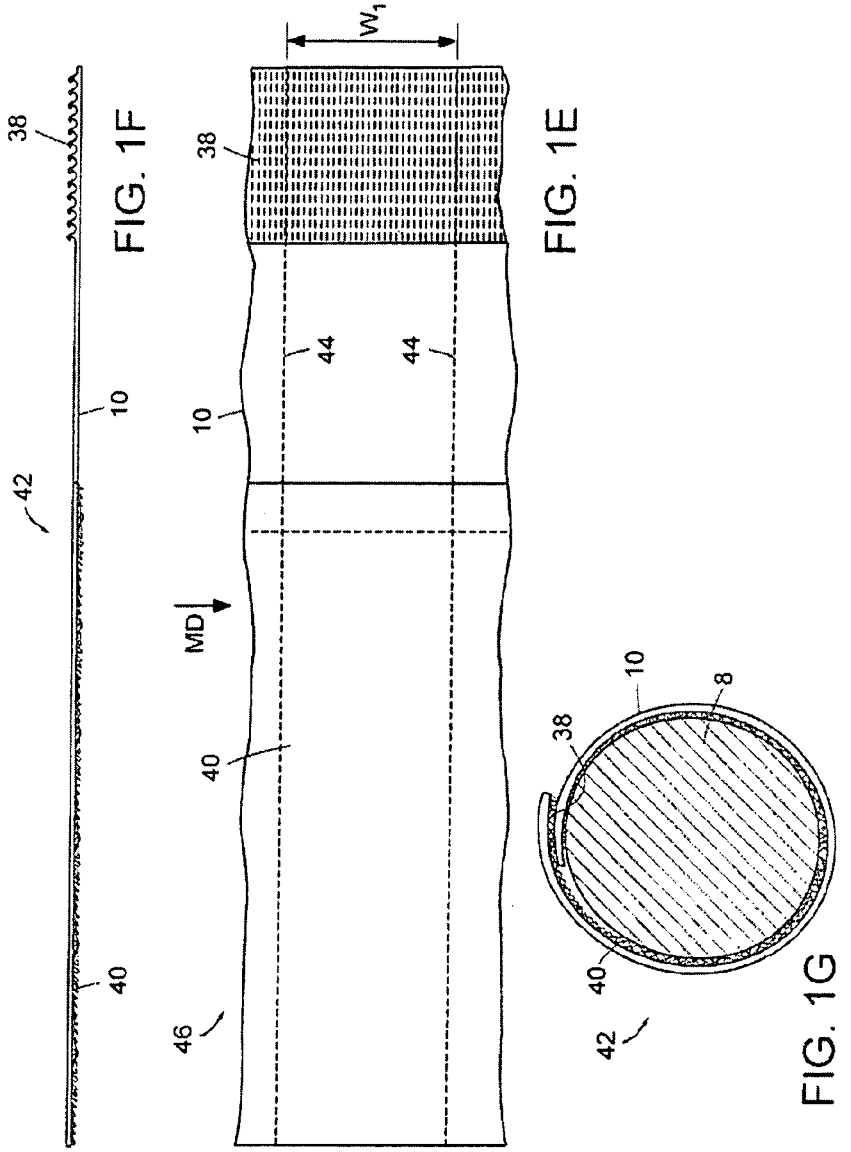
FIG. 1E is a plan view of a composite sheet formed by a calender process in which a hook band and a loop band are combined with an intervening plastic sheet band, the composite sheet cut transversely to the machine direction in sections to form an elongated wrapping.
FIG. 1F is a diagrammatic, edge view of a wrapping formed of the material of FIG. 1F.
FIG. 1G is a diagrammatic top view of the wrapping of FIG. 1F wrapped about an ankle and fastened by engagement of hooks and loops.

For the product of FIGS. 1D and 1E and many other products, union of continuous components into a continuous composite starting material for the wrapping is accomplished by action of pressure and heat produced by roll action. Examples of that are shown in FIGS. 2 and 2A, 3 and 3A, 4 and 4A, 4B and 18.

Figure 4A:
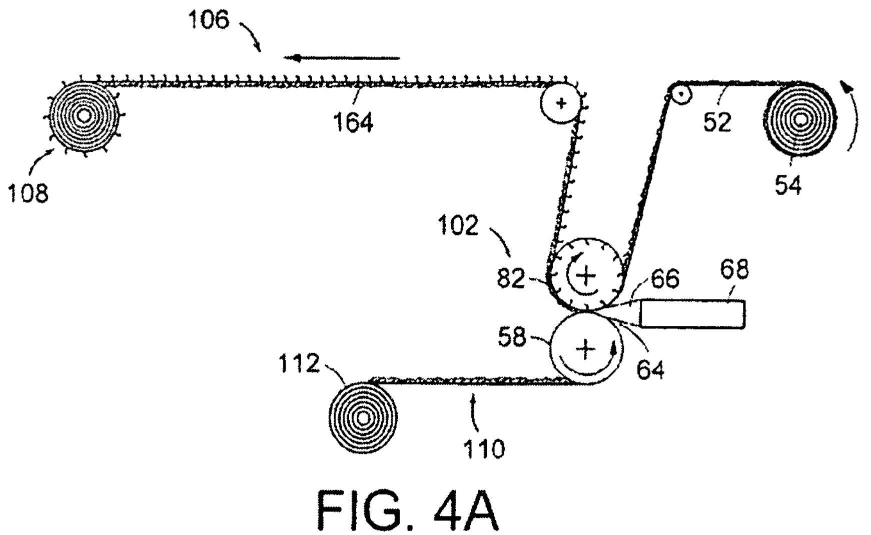
FIGS. 4 and 4A are respectively similar views of a machine performing the functions of FIGS. 2 and 3 while producing a single continuous, composite sheet having two preformed fastener components and a molded fastener component, united in situ as a composite.
Figure 4:
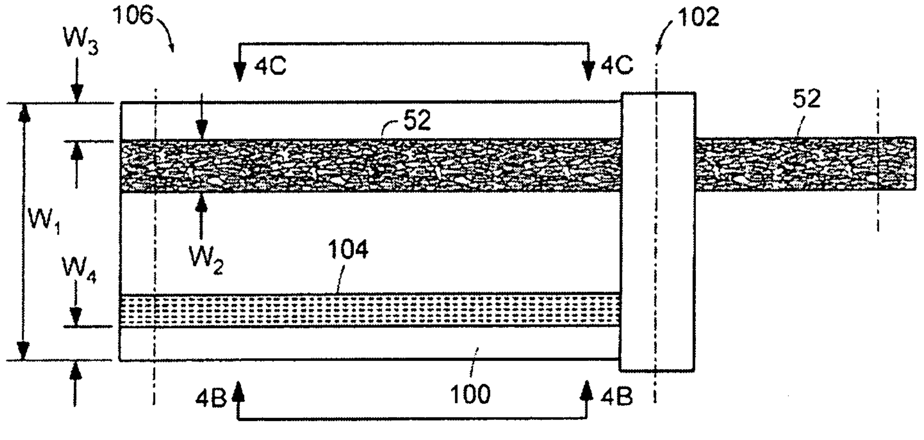

The apparatus and method employing a modification of the apparatus depicted in FIGS. 4 and 4A can produce the product 2 illustrated diagrammatically in FIGS. 1D and 1E. The apparatus 14 produces composite material 16. The roll 18 is not employed and the web material 20 provided at roll 22 is of width corresponding to the width of the pattern of hook molds 24 on the mold roll 26. A cut length 28 of this composite material 16 may be joined at 30, as shown in FIG. 1A, to a pouch structure 32 formed, e.g., of preformed plastic film or one or both sides. Referring to FIG. 1A', a band of preformed plastic film 34 is molded at joints 30 and 36 to the hook side of the composite material 16. Hooks 4 within the pouch 32 are thus able to engage and a pack (not shown) having loop material on a matching face may be inserted into the pouch 32. The function zone 10 includes the pouch 32.

Referring further to FIGS. 1E and 1F, sections 38 and 40 of continuous length include complementary surface fasteners (e.g., hooks 4, loops 6) on opposite sides of a wrapping 42 of FIG. 1F formed along lines 44 from a running length of material 46 shown in FIG. 1E. The functional zone 10, positioned here between fastener sections 38 and 40, can be constructed and arranged to receive additional material to provide a function (beyond mere securing of the wrapping 42) with respect to the body (e.g., 8) about which the wrapping 42 is wrapped. The function is performed by direct action of a suitable delivery member of the wrapping 42 upon the body 8 or by the wrapping 42 serving as a carrier for a device or material that performs the function. The wrappings 2, 42, in diagrammatic FIGS. 1D and 1F, are sized to extend about the girth of the object 8 being wrapped and to overlap upon itself. In FIG. 1G, the wrapping 42 is shown wrapped about ankle 8 (shown diagrammatically) and fastened as illustrated. Loop engageable hooks 4 on one side of the wrapping 42 are engaged by a band of hook-engageable loops 6 on the other side. At intervals, the composite sheet 50 of FIG. 1E is cut along the lines 44 in a direction transverse to the machine direction MD, in other words, transverse to the direction in which the composite continuous sheet 50 is produced by the pressure action. Generally, the completed wrapping 42 is constructed to cause its function delivery section 10 to be pressed against the part 8 of the body to which it is applied through tension borne by complementary releasable surface fasteners, in the embodiment shown, hook and loop fastener components.

Figure 2A:
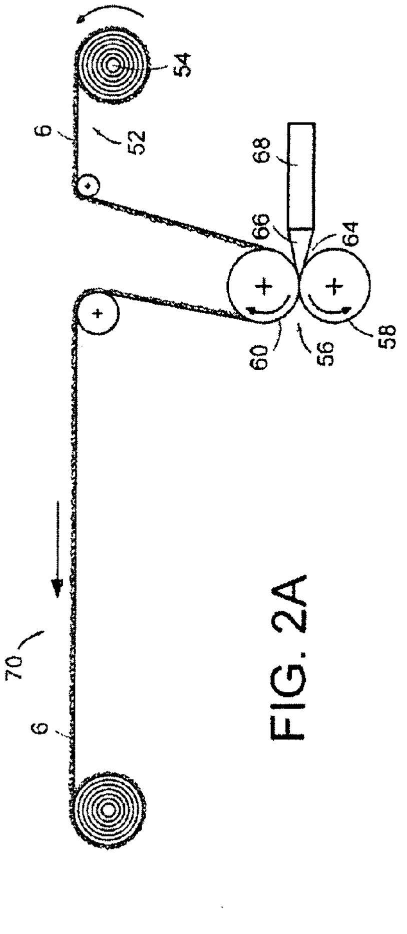
FIG. 2 is a diagrammatic plan view, and FIG. 2A a diagrammatic end view, of a calender-forming-and-uniting machine producing a continuous composite, flexible web material from which wrappings are formed.
Figure 2:
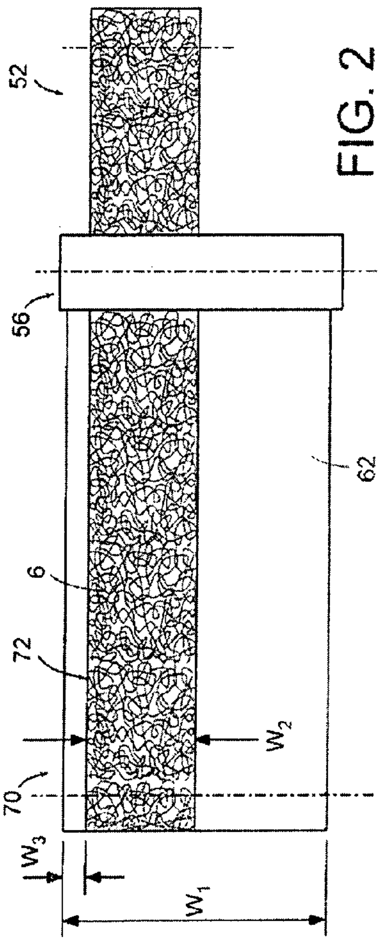

For more particulars of one example of manufacturing a continuous, composite material for a function-delivering wrapping, reference is made to FIGS. 2 and 2A. A preformed material 52, for instance a material defining hook-engageable loops 6 on one side, is introduced as a continuous running length from supply roll 54 into a calender stack 56 comprised of rolls 58 and 60. The calender stack 56 is constructed and arranged to produce a length-wise continuous flat, thin plastic sheet 62 by calender action upon a relatively thick sheet of hot, deformable resin 64. The resin 64 is furnished through a flat die 66 of an extruder 68. In an example, the plastic sheet 62 produced by the calender stack 56 has width $W_1$, for instance 17 inches, and the preformed material 52 being introduced to the calender stack 56 has width $W_2$, for instance 7 inches. The preformed material 52 is applied as a continuous machine-direction band upon the plastic sheet 62 being continuously formed by the resin material 64 being introduced into the nip of the calender stack 56. Under pressure produced by calender rolls 58 and 60, the preformed material 52 becomes embedded or in situ laminated to one side of the plastic sheet 62 being formed. In this example, plastic sheet 62 being formed is wider than the segment of preformed material 52, and the preformed material 52 is introduced inwardly of one edge of plastic sheet 62 (In other cases the preformed material 52 and the plastic sheet 62 may be coterminous to the edges or the preformed material 52 may extend transversely slightly or, in important cases, far beyond a wide or narrow resin sheet being formed).

In the case illustrated in FIGS. 2 and 2A, where preformed material 52 is loop defining material with loops 6, the outer edge of the preformed material 52 is spaced inwardly from the edge of the plastic sheet 62 a distance $W_3$, for instance 1.5 inch. A continuous length composite sheet 70 is a sheet of continuous plastic of $W_1$ inches width with a $W_2$ inch wide band 72 of loop material near but spaced from one edge. The continuous length composite 70 serves as a low cost multi-featured preform material for manufacture of conformable wrapping products (e.g., 2, 42). A completed self-securing wrapping material (e.g., 2, 42) may be formed by joining a preformed band of loop-engageable hooks 4 to an appropriately selected region of the resultant composite sheet 70. Preferably, the band of hooks 4 is formed by molding synthetic resin (e.g., 64) as will be described. Joining the preformed band of hooks 4 to the composite sheet 70 may be done by heat sealing of compatible surfaces of the hook band 4 and the preformed composite 70 or by other joining techniques such as by use of pressure-sensitive or curable adhesives. Afterwards, the material is processed to produce the completed wrapping (e.g., 2, 42), for instance employing techniques described below.

Advantageously for many of these embodiments, the roll formed sheet 62 of the composite 70 and a subsequently joined preformed band of molded loop-engageable hooks or hook performs are of the same or weld-compatible resin and integral welding flanges or other weld regions are provided on the hook band. For instance both the material of sheet 62 and the material of the separately hook band or a joining flange associated with the hook band are both of polyethylene, PVC, polypropylene or nylon, including copolymers and blends. The compatible portions of the two preforms are joined by continuous or spot welding techniques, such as by heat sealing as with polyethylene, use of RF heating as with PVC, or use of ultrasonic welding as with a number of suitable materials.

Figure 3A:
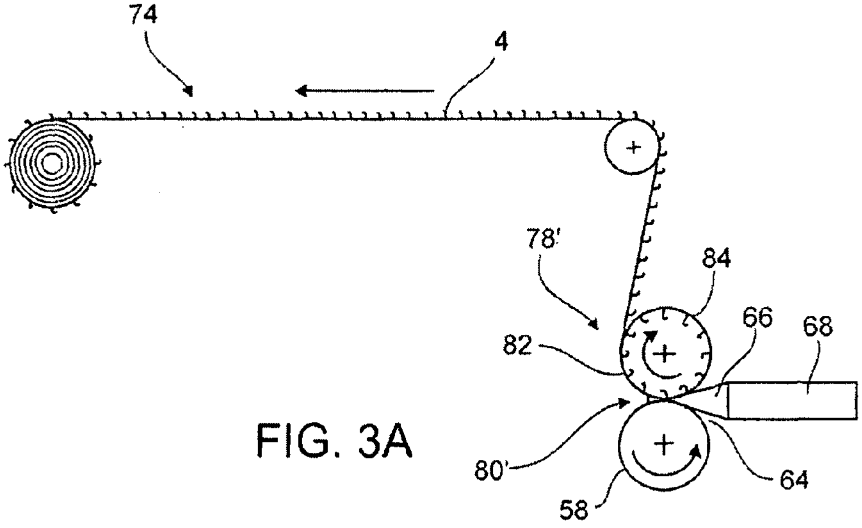
FIGS. 3A and 3B are respectively similar views of a calender-forming and molding machine producing a continuous composite, flexible web material.
Figure 3B:
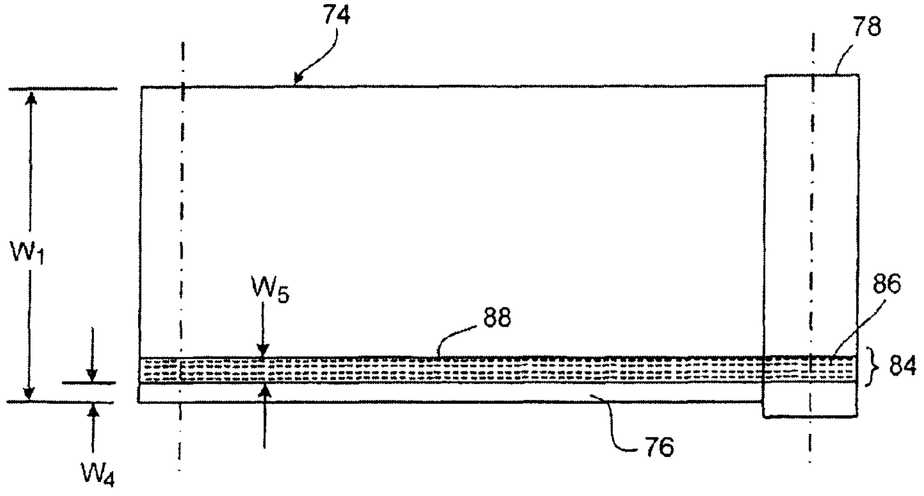

In an example of continuously producing a composite wrapping-forming component 74 illustrated in FIGS. 3A and 3B, a flat plastic sheet 76 of width $W_1$ is produced by calender action of a calender stack 78 upon the formable resin 64 extruded by the flat die 66 from moldable resin provided by the extruder 68. In this case no preformed material is introduced to the forming nip 80. An upper roll 82 of the calender stack 78, in a width-wise defined region 84, has mold cavities 86 in its surface that define loop engageable hooks 4, stems or other hook preforms, self-engaging formations, or other fastener features. In the illustrated embodiment, loop-engageable hooks 4 of form shown in FIGS. 1B and 1B' are molded at hook section 88 located distance $W_4$, for example 1.25 inches, from the edge of the material 74. In this example, the hook band 88 is of width $W_5$, for example 1.5 inches. This process, with fixed mold cavities, can produce the loop-engageable hooks 4 such of FIGS. 1B and 1B' or hook preforms of a selected desired shape or shapes suitable for post-forming action, etc. Molding occurs as the calender stack 78 produces the component 74. A completed self-securing wrapping material (e.g., 2, 42) may be completed by joining a preformed band of loop material 12 to an appropriately selected section of the component 74. Heat sealing, adhesive, or other joining processes may be employed, dependent upon the material and construction of the loop material 12 and the required quality of the joint. For instance, if a binder material in the back of a preformed loop material 12 is an acrylic resin, a heat seal weld may be formed to the sheet 76 along marginal edges, or mid bands of the loop material 12, by heat sealing action with a compatible plastic of the carrier sheet 76. For instance, the sheet 76 may be of polyethylene. In other cases, loop material 12 or other fastener material may be formed in place upon the carrier sheet 76 after the carrier sheet 76 is formed.

In the example of FIGS. 4 and 4A, both hook 4 and loop fastener 6 components are joined in situ to a plastic carrier sheet 100 being produced by calendering action of a calender stack 102. Preformed hook-engageable loop material 52 is introduced into the calender nip, as in FIGS. 2 and 2A, while a band 104 of loop engageable hooks 4 is molded in situ, as described with respect to FIG. 3. This forms a continuous sheet 106. In the embodiment of FIG. 4, the continuous sheet 106 exiting the process has respective continuous machine-direction bands 104, 52 of hook fastener 4 and loop fastener 6 components at appropriate locations on the plastic carrier sheet 100, all components having been united in situ by the sheet-forming and joining calender process. The continuous sheet 106 is wrapped up in a roll 108.

The general concept of in situ lamination is explained in U.S. Pat. No. 5,260,015 by Kennedy et al., and in situ lamination of strips of molded hooks 4, per se, is disclosed in U.S. Pat. No. 6,205,623 by Shepard et al., which are hereby incorporated by reference. By such methods, hook fastener elements 4 or element preforms, such as discrete stems, can be molded to extend integrally from one side of a film of resin (e.g., 100) that encapsulates features, such as surface fibers (e.g., 6), of an underlying substrate to produce a strong and permanent bond.

Figure 4B:
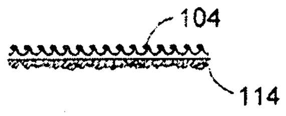
FIGS. 4B and 4C are magnified side views taken on lines 4B-4B and 4C-4C respectively on FIG. 4.
Figure 4C:
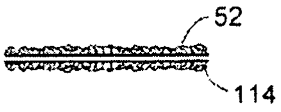

In the example of FIG. 4, the bands 104, 52 of hooks 4 or hook preforms and loops 6 are shown disposed on the same surface of the continuous sheet 106. However, by alternatively, or simultaneously having a continuously supplied loop material 110 following the path from takeoff roll 112 on the opposite side of the incoming resin 64, the loop material 110 of loop material is introduced to the lower roll 58 on the bottom side of the plastic sheet 100. Referring to FIGS. 4B and 4C, the loop material 110 becomes a band 104 so that the band 104 or bands of hooks 4 or hook preforms and a band 114 or bands of loops 6 are disposed on opposite sides of the formed continuous sheet 106. The arrangement of FIG. 4A, without use of the roll 108, may be employed to form the wrapping of FIGS. 1F and 1G.

Figure 4D:
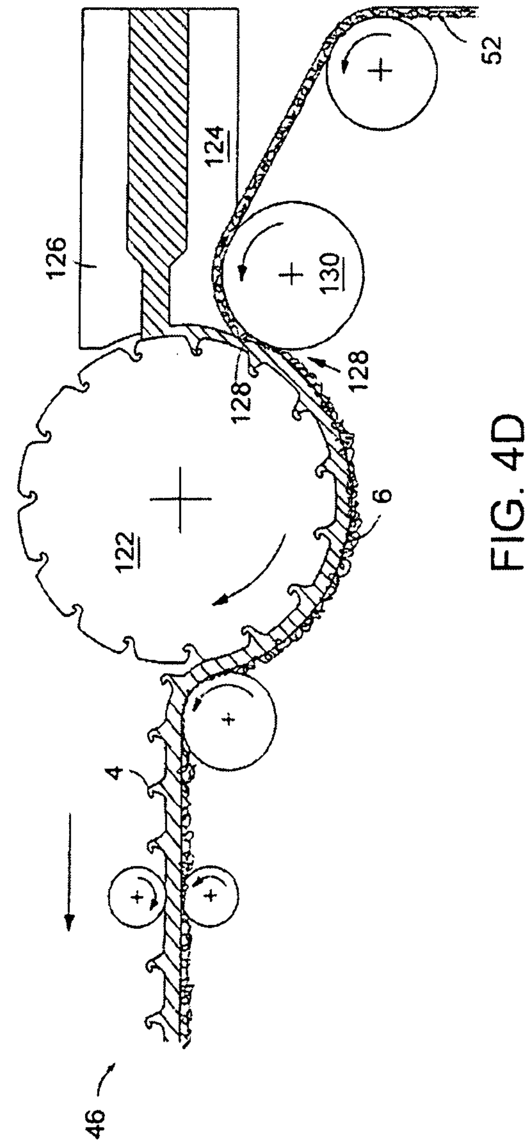
FIG. 4D is a diagrammatic cross-sectional view (thicknesses grossly exaggerated) of another machine forming a material similar to that produced by the machine of FIGS. 4 and 4A, in this case the hook and loop bands residing on opposite sides of the resultant composite.

Another apparatus and process, as illustrated in FIG. 4D, can be employed to form the material 46 of FIG. 1E and the wrapping 42 of FIGS. 1F and 1G. In this case, the material 40 having a section 38 with hooks 4 extending from a plastic sheet base layer is formed by a mold roll 122 having hook cavities, e.g. of width $W_5$ (shown in FIG. 3B), as the plastic from the extruder passes through a gap formed between the mold roll 122 and a complementary-shaped extension 124 of the extrusion die 126. While the resin is still molten, the loop material is introduced and laminated in situ to the resin at a nip 128 formed between the mold roll 122 and pressure application roll 130. At this point the hooks 4 are still in their mold cavities, protected from the effects of laminating pressure. The material 46 of width $W_1$ with hooks and loop bands (as shown in FIG. 1E) can thus be produced.

In these and other roll-forming arrangements, provisions may be included to impart cross-machine strength to the formed composite web. In some cases this is provided by a cross-machine-strong preformed fastener material or its carrier. In other cases, a reinforcing scrim may be introduced to the roll-forming station in a manner by which the scrim is embedded in the sheet being formed. Examples are introduction of an open reinforcing scrim on the molding roll side of resin entering the forming gap through which the resin passes in entering the mold cavities, and co-extruding two layers of resin while interposing a running length of the scrim between the layers before the layers enter the forming gap. The coextruded resin may be of the same or compatible materials. In one case a relatively stiff resin is employed to form the hooks and a thin upper part of the base layer, and a compatible resin, for instance a copolymer or blend, having elastomeric properties may form the predominate thickness of the base layer under the hooks and a calendered sheet extension as well. In this manner a wrapping material with elastic properties is formed. In some cases the reinforcing material may be omitted. In other cases the predominate thickness of the base layer may instead be selected for its toughness and the reinforcing layer may be omitted.

Figures 5, 5A, 5B, 6:
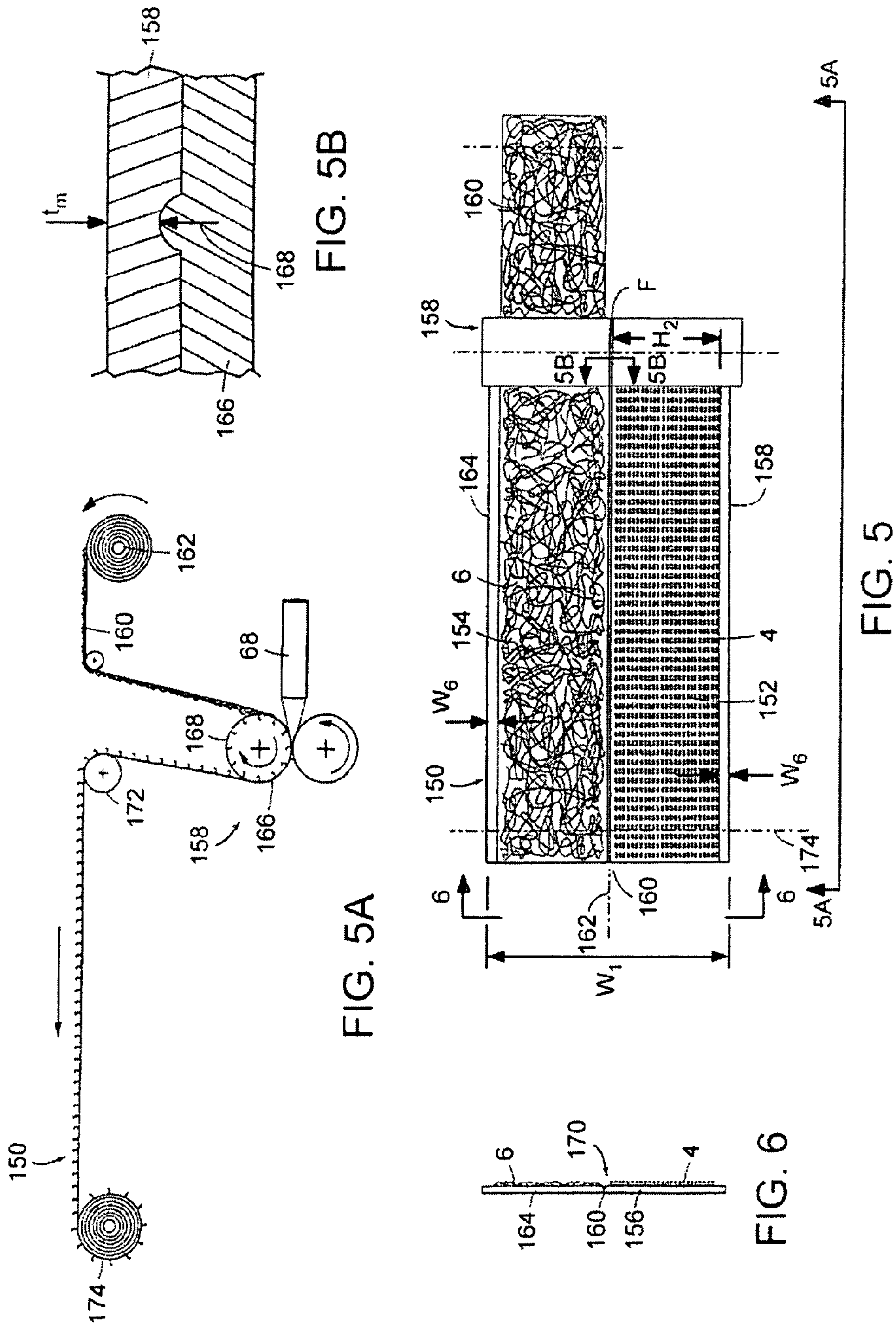
FIGS. 5 and 5A are diagrammatic plan and end views of a machine forming a continuous, composite flexible material having similarities to that formed in FIG. 4, but with much wider bands of hooks and loops.
FIG. 5B is a cross section view taken on line 5B-5B of FIG. 5.
FIG. 6 is a transverse cross-section taken on line 6-6 of FIG. 5.
Figure 7:
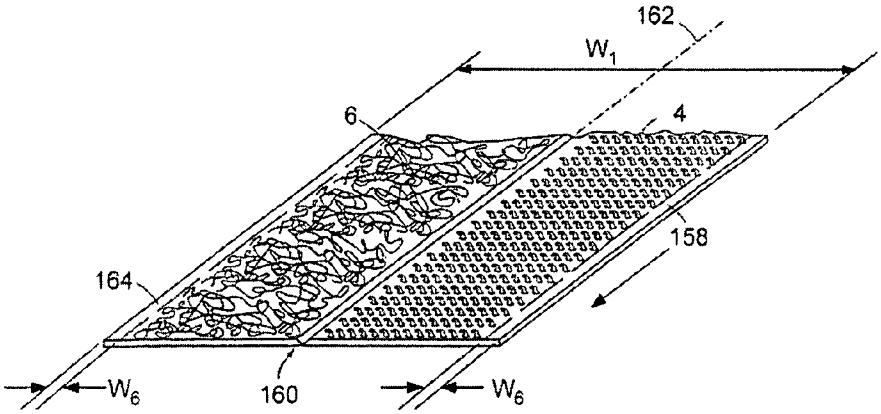
FIG. 7 is a perspective view of the sheet-form material resulting from the continuous calender roll process illustrated in FIGS. 5 and 5A.
Figure 7A:
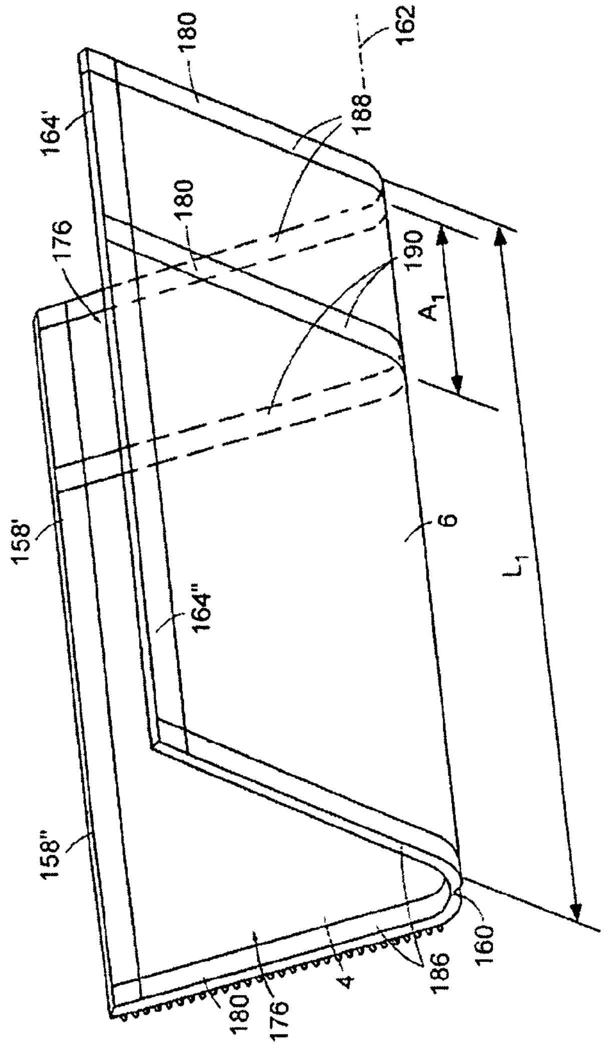
FIG. 7A is a diagrammatic perspective view with thicknesses exaggerated of the material of FIG. 7 while it is being partially folded.

In a further example, the basic apparatus and process described with respect to FIGS. 4 and 4A is employed in FIGS. 5 and 5A, except that wider loop material is used and there is a wider mold cavity section in the mold roll to form composite material 150. Two parallel fastener bands 152,154 of loop-engageable hook 4, and hook-engageable loop 6, respectively, are formed on the same side of an in situ produced machine-wide plastic carrier sheet 156. Resin is introduced into the nip of a calender stack 158 over the full roll width. In a manner similar to that illustrated in FIG. 2, the preformed loop material 160 from supply roll 162 is of appropriate width and position to leave, at the adjacent edge, a weld flange 164 free of loop material. The width $H_2$ of the mold section of roll 166 which carries mold cavities 168 is also sized slightly less than half of the width of plastic sheet 156. This produces the wide band 154 of hooks 4 or hook preforms that is bordered at the outside edge by weld flange 158 of calender-produced plastic sheet. Referring also to FIGS. 5B, 7 and 7A, a narrow center region 160 between the bands 152, 154 of hook and loop is also devoid of hooks and of loop material. A central machine-direction fold axis 162 is defined by suitable formation of the surface of roll 166 to facilitate folding the laminate, crosswise to the machine direction. For example a small, circumferential central raised formation 168 (FIG. 5B) on the surface of roll 166, forms in the plastic sheet 158 a machine direction region or notch 170 of decreased thickness $t_d$, about which the plastic sheet 158 will preferentially fold in creating the continuous wrapping composite 150. In some preferred cases, weld bands of plain resin (not shown) lie along each side of the fold line axis 162, to enable welding of the two plastic layers together in this region after folding. Following molding and in situ laminating, the wrapping material 150 is cooled, removed from the mold roll, passed over tension roll 172 and rolled up into supply roll 174.

As shown in FIGS. 6 and 7, the specially adapted composite starting material 150 for forming self-securing, function delivery conformable wrappings is thus a wide roll-formed sheet 156 having hook and loop bands 152 and 154 of substantially half-width extent of the sheet 156, and integral outer weld flanges 158, 164 of width $W_6$, e.g. about 0.5 inch, comprised of plain flat resin sheet. The material 150 is produced by pressure action by a roll, preferably the calender action shown in FIG. 5A. This material 150 is suitable for forming one or more carrier pockets or pouches 176, see FIG. 7B, and the remainder of the body of an extended, conformable wrapping (e.g., 2).

Figures 7B, 7C:
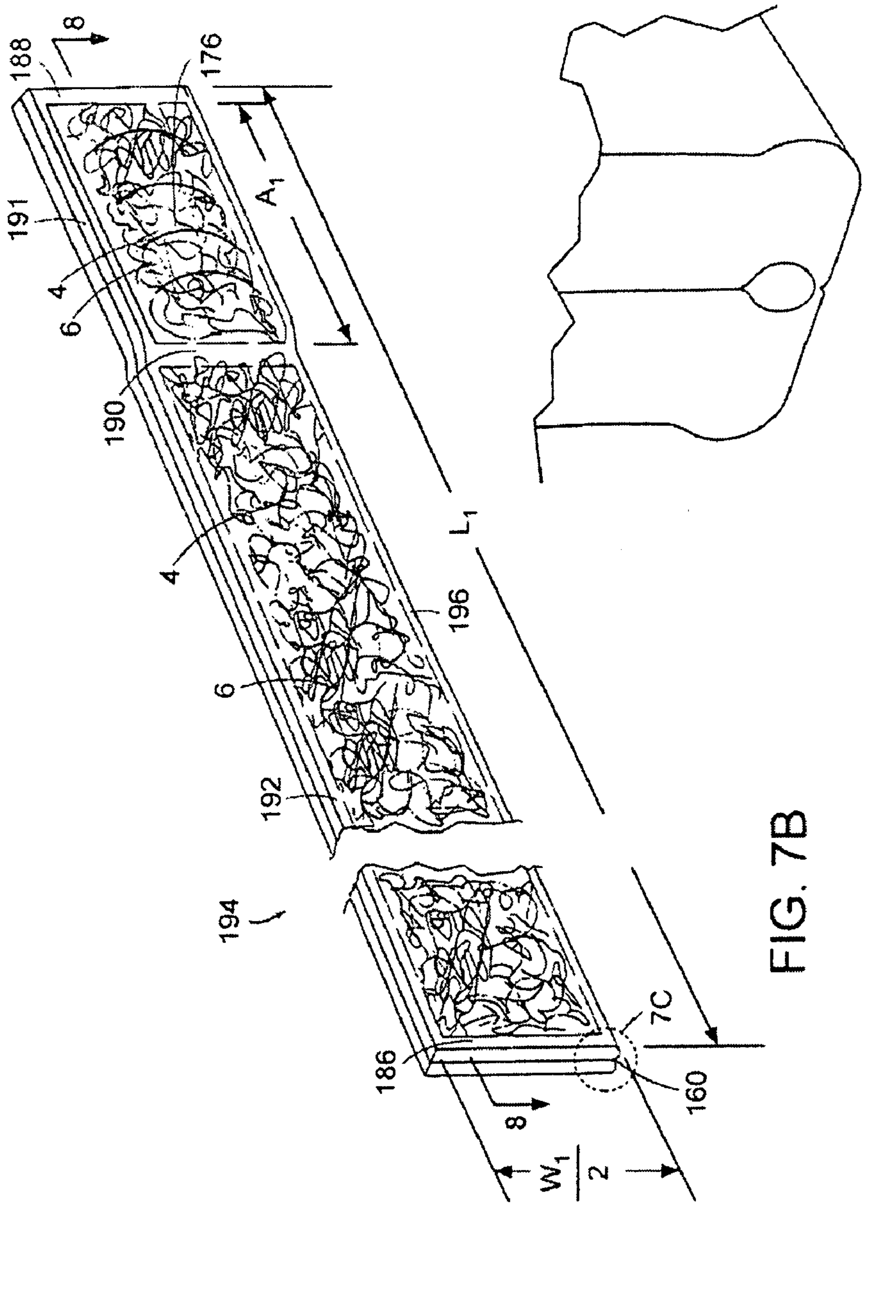
FIG. 7B is a perspective view of a flexible wrapping with a formed pouch made of the material of FIG. 7A.
FIG. 7C is a magnified view showing the fold at the reduced section at the lower edge of the wrapping of FIG. 7B.

As suggested in FIGS. 7A, and 7B, as this material 150 is folded about middle machine direction fold axis 162, the weld flange sections meet, i.e. weld flange at 158', 164' and the location of a pouch to be formed and weld flange sections along the main body, 158", 164". These weld flange sections can be selectively welded together to create a flattened tube covered with loop-engageable hooks 4 and hook-engageable loops 6 on the oppositely directed sides. In FIG. 7A, lines 180 transverse to axis 162 define regions where transverse welds may be formed. FIG. 7B illustrates the welded wrapping unit. Welding flange sections 158', 164' of FIG. 7A form weld 182 and flange sections 158", 164" form weld 184, each parallel to axis 162. Transverse end weld portions 186, 188 and internal pouch-defining weld 190 complete the unit.

As an option, weld flange sections 158, 164 at one or more pouches 176 being formed are left free to provide a top pouch opening or openings for access by the user. The continuous sheet 150 that has been folded in half about axis 162 is advantageously transversely welded with double width at 158, 164 in an in-line process, at a selected repeat length to define the length of the flexible wrapping unit. After this, the running length of material 150 is cut at the repeat length, to form weld regions 186 and 188.

As another option, plain weld flange sections 158 and 164, illustrated in FIG. 7B, may be omitted and the fields of hooks 4 and loops 6 allowed to extend to the edges of the wrapping 150. In this case, the welds 191 and 192 are formed by application of heat and pressure through the hooks 4 and the loops 6 to cause the corresponding portions (158, 164) of the plastic backing to weld together.

Figure 7D:
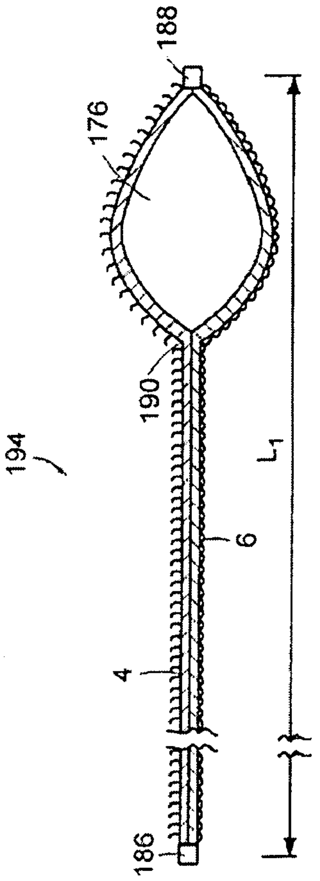
FIG. 7D is an edge view of the embodiment of FIG. 7B, showing a bulge attributable to a filled pouch.

As mentioned previously, transverse welds at the ends, 186 and 188 (typically sections of a double wide single weld which is cut to sever the leading unit during production) define the repeat length for the continuous production process. Each repeat length of the material 150 is a wrapping 194. As desired, a selected number of intermediate transverse welds 190 are applied through the thickness of the hook section 152 and the loop section 154 of the composite material 150 to form one or more pouches 176 of limited dimension along the wrapping 194, or to provide optional cut lines at which the user may choose to shorten the wrapping 194 by cutting. In the example of FIG. 7B, one intermediate weld 190 defines the pouch 119 with the end weld 188. By suitable placement of transverse weld 190, each pouch 176 is formed of selected width to accept a device, instrument, a preformed pack or loose substance to provide the desired action upon the body 8 about which the wrapping 194 is to be affixed. The wrapping 194 with the multi-purpose pouch 176 is illustrated in FIGS. 7B, 7D and 8.

The resultant flexible wrapping 194 is of selected length $L_1$ to match and exceed the girth of the ankle, knee, torso or other part of the body or other object to be wrapped. In advantageous embodiments pouch 176 is filled with a preformed chemical pack (for instance a hot or cold pack), a coherent gel or loose filling suited to be heated or cooled for applying thermal treatment, loose reactive chemicals, a thermo-electric unit for cooling or heating, fluid absorbing cotton or gauze, drug carrying material or an air or liquid bladder. After insertion of the desired contents, the weld flanges 158', 164' may be welded at the pouch 176 to form a sealed container, e.g. to form a reaction or protective chamber or suitable hook and loop arrangement may be provided to secure the pouch contents or to close the opening of the pouch 176. The material of the layer of the substrate that is to lie between the skin and the hot or cold pack should be selected to limit the rate of heat transfer into or out of the skin, to reduce the risk of excessive heating or cooling.

The resultant wrapping 194 is thus comprised of a composite, laminated sheet 158 folded along machine direction axis 162 at the reduced thicknesses fold formation $t_n$, the inwardly directed surfaces of plastic resin joined at selected weld lines, one face of this extended wrapping substantially completely covered with loop-engageable hook fasteners 4 and its oppositely directed face substantially completely covered with hook-engageable loops 6. Variations include a series of discrete, spaced apart continuous bands of the two fastener materials, effectively enabling engagement of all or selected regions of the faces of the wrapping while economizing with respect to the amount of fastener employed. As shown, the plastic backings of both faces enable welding together along selected weld lines that form welds 188 and 190). After insertion of contents, the top flanges 158' and 164' may be sealed together to complete a sealed pouch 176 in a wrapping 194 having length $L_1$ and height $W_1/2$, or other securing or closure provisions may be employed. Advantageously, in many instances, bottom weld 196 that is parallel to top welds 191, 192 is formed at weld bands provided immediately above the fold line 160.

For low cost wrappings, it is advantageous that the pouch contents are inserted during manufacture of the wrapping 194. This is done while top edges of the pouch 176 are unsealed. The nature of the contents and their method of insertion depends upon the desired function. In cases that a preformed flexible package or device is to be inserted into the pouch 176, the pouch 176 may thereafter remain open, or it may be sealed. If chemical reactants or drugs are introduced into the pouch 176, the edges of the pouch 176 are sealed together with precision to provide a fluid-tight reaction chamber or protective pouch capable of safely holding the chemical reactants or drugs. By making the film of in situ laminate of resin capable of strong continuous heat seals, such as polyethylene, the flanges (e.g., 188, 190) can be heat-sealed to each other to provide water tightness and strength along the edges as well as along the pouch walls. This ensures containment of the chemical reactants. An advantageous resin for such embodiments is commercially available linear, low-density polyethylene such as LL-6407 Exxon Mobile resin.

In instances in which the pouch 176 is left permanently open, such as to enable the user to remove a cold pack, hot pack or other device and replace it with another pack of the same or different function, closing flaps may be formed of the composite material 194 and suitable strips or spot regions of surface fasteners are provided to close the pouch 176 and secure its contents, but enable it to be opened and closed for reuse.

For many functions performable by the wrappings (e.g., 194), conventional materials are useful. Typical reagents for a chemically-activated cold pack is ammonium nitrate and a separate, rupturable packet of water. To activate the cold pack, the water packet is broken by the user, initiating reaction of the water and ammonium nitrate as an endothermic reaction that creates a useful cold surface. In other cases a cooling fluid, gel or loose material is provided in a separate packet or in the pouch defined by the wrapping. Such materials may be pre-cooled by the user by storage in a freezer, or a regulatable thermoelectric cooler may be inserted in the pouch (e.g., for moderate, continual cooling).

An insertable hot pack may contain material that can be heated by a microwave oven, e.g. a packet containing microwavable gel or heatable granules, or the pouch of the wrapping may contain the particles, and the entire unit may be placed in the oven. An exothermically reactive mixture may be provided such as are employed with hand warmers, such as iron particles with carbon and salt; when exposed to air, the salt absorbs moisture, initiating oxidation of the iron particles and production of heat. A regulatable thermoelectric heater may be inserted in the pouch.

As previously noted, by selecting the location for the end cut of the wrapping 194, a conformable, function-delivering wrapping 194 of any desired length may be manufactured. A wrapping (e.g., 194) longer than that normally required to wrap around the part of the body, such as an ankle, is useful to cover a range of sizes or enable other uses. Since the surfaces of the wrapping (e.g., 194) can be continuously covered by engageable fastening materials, the excess length may be wrapped upon and secured to itself, avoiding loose ends. A universal, long wrapping can be usefully formed, to wrap around numerous components of the body, for instance the ankle, elbow and knee, even the head, of children, youth and adults. Likewise an extended veterinarian wrapping may be provided for use with a range of sizes of animals. As previously suggested, the wrapping may usefully be provided with a number of spaced apart transverse weld lines at which it may be selectively cut to shorten the wrapping to the length required. In other cases, as in a hospital or emergency setting, a continuous roll of the conformable wrapping with a sequence of repeating, spaced apart pouches and cut lines is provided from which a conformable, self-securing wrapping of any desired length may be taken. Tear strips at the cut lines may be provided, that enable the wrapping to withstand the desired tension during use, but which are readily severable as by provision of a special tear string, these are useful for shortening the wrapping and for removing and disposing of the wrapping in cases in which the fasteners are not readily releasable.

In the case of a hot pack, if the wrapping is made with sufficient length, one can wrap it from the backside, around the waist of a person, to apply heat to the lower back. A typical dimension for $L_1$ to be useful about the ankle, knee and the head is in the range of 26-28 inches. About the waist, a length of 50 or 60 inches can be appropriate. For applications to the back by a user without assistance, the pouch is advantageously placed in the middle of the wrapping. This enables attachment of the wrapping while achieving proper placement of the treatment zone in the middle of the back.

In advantageous embodiments, fibrous loop material is so located in the wrapping as to lie against the skin when the wrapping is in place. This can provide soft, smooth comfortable contact. Such loop material can be of materials selected to act as a slight thermal barrier to prevent uncomfortable contact of cold or hot plastic directly against the skin.

The wrapping may be constructed to be drawn tightly and secured, in a manner to produce compression against a desired region to be treated. Such snug cinching can ensure that the pack or instrument is intimately associated with the region to be treated for thermal therapy, drug delivery, etc. For a cold or hot pack applied to the ankle or knee of a person, for instance, the wrapping is constructed to withstand a cinching force of between about 3 and 6 pounds.

Furthermore, a dressing, pack or instrument inserted in the pouch may be configured to provide a bulge in the wrapping of desired form, shaped to produce a desired degree of localized pressure to enhance intimate contact with the region to be treated or to provide desired support.

Figure 8A:
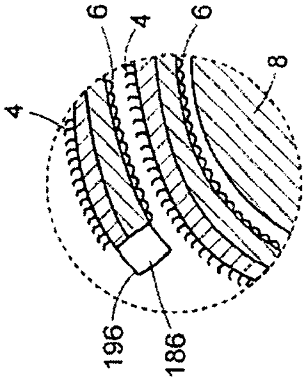
FIG. 8A is a further magnified diagrammatic view of the end fastening portion of FIG. 8.
Figure 8:
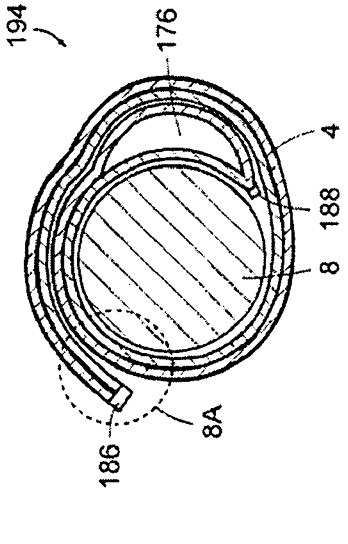
FIG. 8 is a diagrammatic, highly magnified cross-sectional view of the embodiment of FIG. 7B taken on line 8-8 showing the flexible wrapping wrapped about an object, positioning the filled pouch with respect to it.

Referring to FIGS. 8 and 8A, wrapping 194 securely holds the contents of the pouch 176 close to body part 8, for instance an ankle or arm. The wrapping fastens to itself by touching the loops 6 to the hooks 4 as illustrated in FIG. 8A. Because of the weld 186 provided at the free end of the wrapping 194 shown in FIG. 7B, a small dead region 198 of fastener material is provided that is incapable of fastening engagement. This provides an easy peel, free standing tip to grasp to initiate unwrapping. Thus, while the entire length of excess wrapping tightly engages itself without an undesirable loose tail, the extreme tip 198 remains free to be grasped.

Selection of a suitable preformed non-woven material depends upon cost, quality and number of uses objectives, e.g. whether it is to be a single use device or whether a number of repeated uses are desired. For economy, a non-woven product formed by needling staple fibers followed by stretching and binding as shown in U.S. Pat. No. 6,342,285 is useful. This material is available from Velcro, USA as loop L3310. To enable a large number of repeated openings and closing, the loop material may be a knit fabric with acrylic binder at its back such as Loop 3905 available from Velcro, USA. For intermediate cost applications, extremely light weight knitted materials may be employed.

For low cost synthetic resin (e.g., 64) for the hooks 4, good weldability, good sealing qualities, etc., polyethylene is advantageous, while for certain performance characteristics, other resins are selected, e.g. PVC for comfort, conformability, or RF welding; polypropylene for strength and cost; and polyester for high strength applications where a degree of stiffness of the wrapping is useful.

In another embodiment having extensive loop coverage and breathability, the plastic sheet side of the laminate in the loop area is not entirely covered with resin sheet. Instead, as will be described for the example of FIGS. 14 and 14C, parallel, spaced apart bands of resin are provided between which are bands of porous loop material, free of resin. The free regions provide porosity that enables air or moisture to pass through. Such a wrapping is useful for the case in which a preformed cold pack is dropped into a pocket formed by the wrapping. Two major plastic bands, for instance, may be provided on the porous material in such an embodiment, at the top and bottom long edges of the wrapping, to enable major welds to be strategically placed for holding a folded assembly together. Between those weld regions, only two or three narrow beads or bands of resin may be employed, such as bands ⅛ inch wide, that leave most of the area free to breathe. Such beads or bands of resin enable formation of spot welds sufficient to define a pouch capable of retaining an inserted pack or device. During formation of the wrapping, these beads or bands of resin, carried on the inside surface of the porous material, are engaged by a transversely extending weld bar to form spot welds to matching, weldable portions on the opposite side of the folded material. Where the opposite side comprises a continuous plastic base layer, welding of a portion of each bead is assured wherever a cross-wise extending linear heated weld bar may engage the plastic bead against the opposed plastic surface. In such cases, little care is needed to provide registry.

Figure 9A:
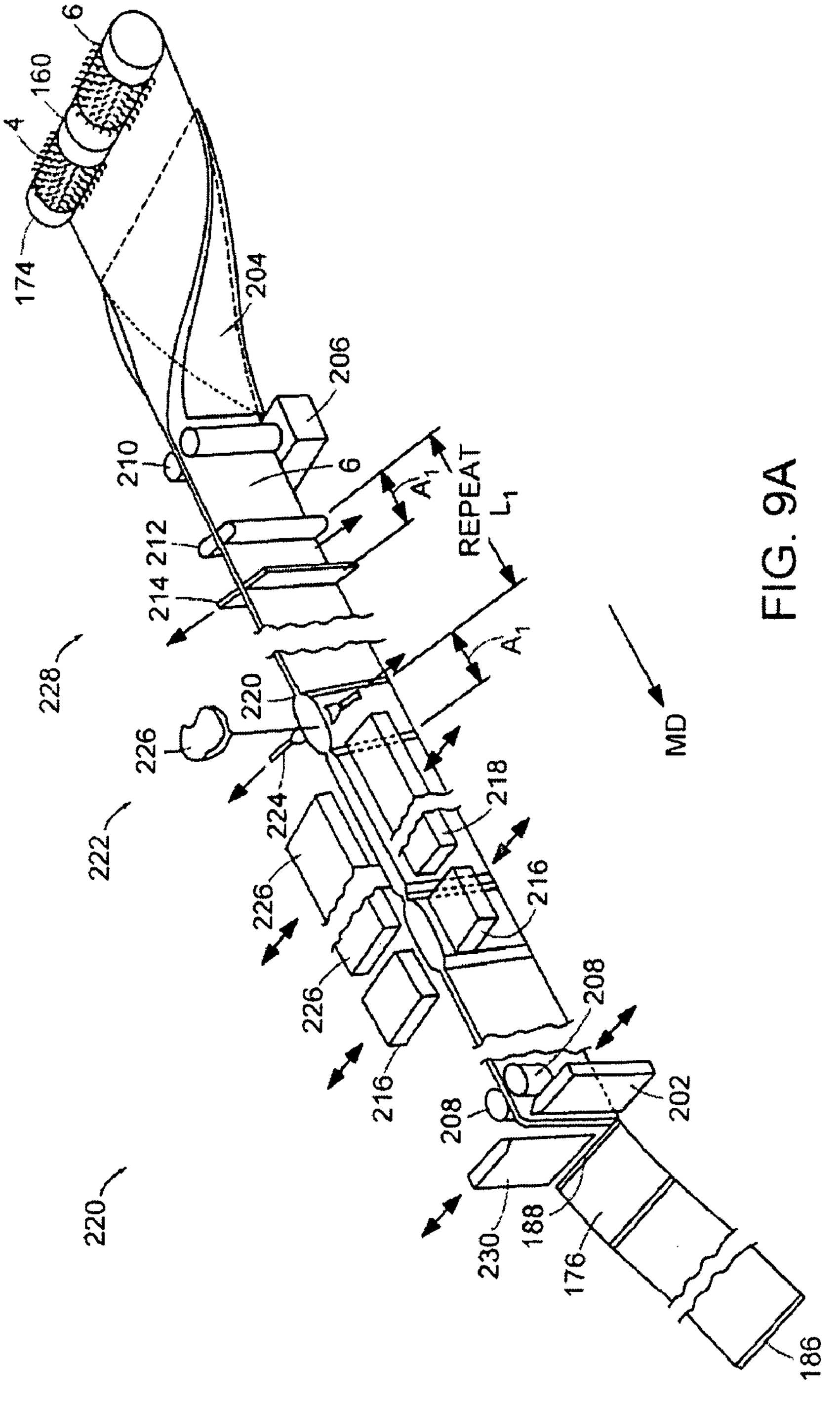
FIG. 9A is a perspective view of a machine for forming a conformable wrapping from a supply of preformed starting material that previously was formed with a roll process.
Figure 9B:
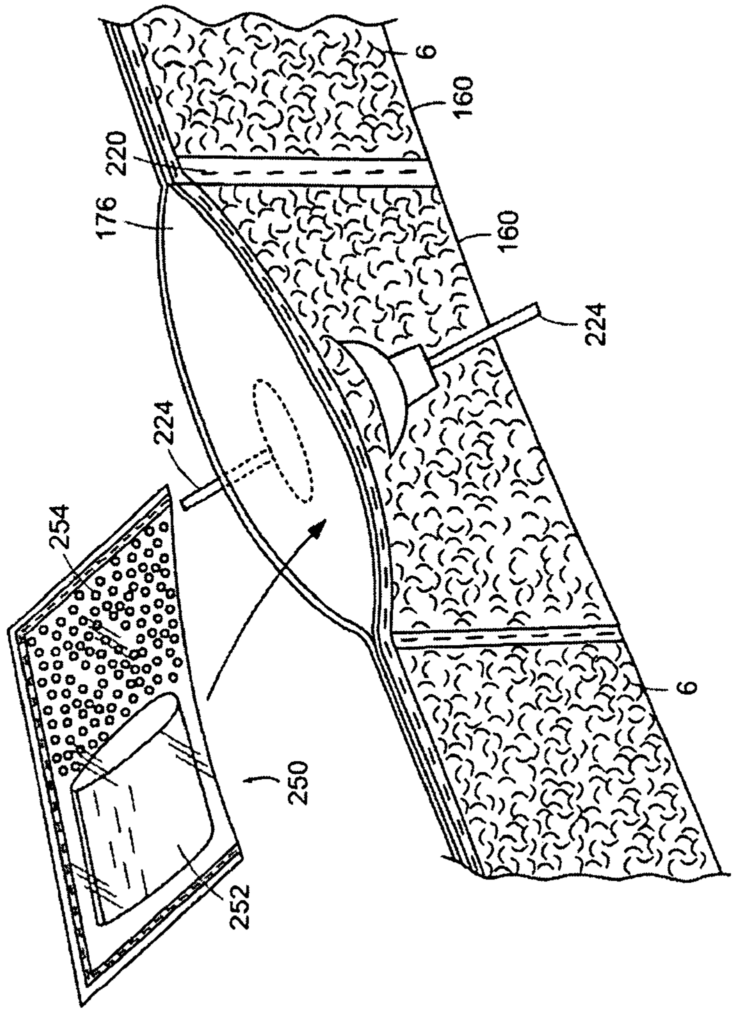
FIG. 9B is a perspective view of the step of inserting a preformed cold pack into the wrapping of FIG. 7B during the process of FIG. 9A.

Examples of in-line production of conformable wrappings using composite starting materials formed as described above, by example, will now be described. In FIG. 9A, the operative components of a horizontal poucher machine 200 are shown, which has been specially adapted to form the extended, self-engaging wrappings 194. The poucher 200 extends from a supply roll 174 of the preformed material to a cutoff blade 202. In this example, a specially prepared, continuous composite component 150, produced according to FIGS. 5 and 5A, is lead from the supply roll 174 into a former 204. Once centered on former 204, the composite passes through drive stations 206 and 208 located near the entry and exit of the machine 200, respectively, and which are coupled to act in unison. Rolls 210 extending the full width of the composite material 150 at drive station 206 pull the sheet-form composite 150 through the former 204. In coordination with the downstream drive station 208, the rolls 210 also tension the material 150 at sealing stations 212, 214, 216 and 218. A heat seal 220 that forms separated heat seal portions 186 and 188 of FIG. 7A, 7B and a heat seal 190 are formed at stations 212 and 214, respectively, as shown in FIG. 9A. By indexing action, the web 150 passes from the weld station to filling station 222. Here the two welds 220 and 190 are positioned on opposite sides of a pair of oppositely acting separators, such as suction cups 224, as shown by FIG. 9B. By the suction cups 224 engaging respective sides of the web 150 at the pouch 176, and then moving in opposite directions away from each other, the top of the pouch 176 between welds 220 and 190 is opened to enable a preformed pack or loose contents 226 to drop into the pouch.

One alternative method for opening the sides of the pouch 176 is to use hook fasteners 4 and loop fasteners 6 to engage and pull back the loop and hook sides of the material, respectively. This can be used to open the sides slightly, at which time spreader blades can be inserted and spread apart to complete the action. Another method for opening is to place the fold axis 162 slightly off center of the overall web width. Thus, when folded about axis 162, one edge of the folded material will extend higher than the other. Given height difference between opposed edges, high-pressure air blown into the pouch area or mechanical means such as pinchers can open the sides.

Downstream drive station 132 in conjunction with drive station 208 indexes the folded and welded material from the filling station 222 to the top seal station 226. Sealing jaws of station 226 with motion similar to that of the heat seal bars at stations 212 and 214, move in to seal and out to release. While the machine 200 is forming a pouch 176 at station 228, and filling a previously formed pouch 176 at station 222, the sealing jaws at station 226 engage to seal shut the top of the wrapping and form weld 192 along the non-pouch top of the wrapping 194. Simultaneously, if desired, the sealing jaws at station 216 engage to seal shut the top of a previously filled pouch 176 to form weld 191, securing the contents in the pouch 176. Where the top of the pouch 176 is to be left open, sealing jaws at station 216 are not used. Meanwhile, the downstream cutting jaws 202,230 sever the double width seal 220 formed at heat-seal jaws 212 to form trailing weld portion 188 of the leading unit and leading weld portion 186 of the next units 194. This severs the leading wrapping 194 from the continuous assembly formed from the continuous material 150.

The repeat length $L_1$ for the system 200 illustrated, established by the desired length of the conformable self-securing wrapping product 194, extends from the sealing bar 212 to previous weld 220 formed by the bar 212 at the upstream end of filling station 222. This repeat length is adjustable between production runs by adjusting machine index, to determine the length of the self-securing wrapping 194 being produced. The distance between seal jaws 212 and 214 is also adjustable along the length of the machine 200, the spacing depending on whether larger or smaller pouch space is desired, based upon volume or size of the contents 226 to be inserted. Additional heat seal jaws may be provided to form multiple pouches in a single wrapping 194, or to locate the pouch 176 at the center or other desired location of the wrapping 194, or to provide optional cut lines at which users may shorten the product 194 as with a scissors or portable knife blade.

At the end of the pouch forming line, the knife edge 202 cuts the product 194 against anvil 230, to sever the leading wrapping unit 194. The finished unit 194, shown falling off after cutting, may instead pass to a shingled inching conveyor (not shown) from which it is removed and packed in cases. Standard production throughput may be of the order of 100 to 200 units per minute, in many cases the limiting factor is how fast the contents may be placed in the pouch 176.

Since the machine 200 has a start/stop operation, with dwell time required, a conventional provision such as an accumulator may be provided to provide a constant turning of the supply roll.

During operation of the machine 200, during the fold, seal, fill, and cut sequence, the continuous composite sheet 150 advances in-line in continuous sheet form from roll 174 with hook and loop bands of the preformed composite material 150 facing downward. As the composite material 150 moves from supply roll 174 to drive station 206, the material 150 folds along the machine direction about the fold axis 162 so that the plastic backings of the sides are brought face-to-face, positioned to be heat sealed together, while the hook and loop panes are caused to lie on opposite outside faces of the unit 150. The sides are heat sealed transversely to machine direction at sealing stations 212,214 by heated heat seal bars 226, 218 that move in, seal and return in a forming cycle. The seal 220 that is formed by heat seal bar 212, being twice as wide as the seal 190 that is formed by bar 214, enables the final cut at blade 202 to bisect that seal 220 to form trailing weld 188 of the leading wrapping unit 194 and leading weld 186 of the next unit 194. The pouch 176 for each unit 194 is formed by the two transverse heat seals 188 and 190, the top machine-direction seal 191, if employed, and the bottom fold 160 of the material 150, (and additional bottom seal 196 when employed). Each time the web 150 stops at the fill station 222, an appropriate separator separates the sides of the pouch 176 sufficiently to enable a duck bill dispenser or other suitable device to enter and place in the pouch 176 a discrete chemical pack, loose chemicals, or other devices, material or instruments to be carried in the pouch 176. The final drive station 208 has specially shaped drive elements to engage and drive the composite 150 while accommodating passage of the bulged pouches 176. In one case, as shown, a short drive pair engages the upper edge only of the formed wrapping material 150 to pull the material 150 through the machine 200 and advance it to the cut-off station having blade 202 and anvil 230.

For wrapping products 194 in which it is desired to enable the user to insert and remove packs from the conformable wrapping, top sealing bars 216 are inoperable and top weld 191 of FIG. 7B is not formed.

In some instances, the wrapping 194, with or without a packet or device inserted in the pouch 176, moves to a kit-assembly station where the wrapping 194, with open or openable pouch 176 is assembled in an overall kit along with a supply of the same or different pouch inserts that may be selected for use. This provides the capability of employing the same wrapping a number of times, such as to carry out a prolonged treatment with a sequence of the same kind of inserts, or to treat a region to different condition at different times, e.g. cold therapy for a fresh injury, and heat therapy later on.

FIG. 9B shows a preformed cold pack 250 containing a rupturable water bag 252 and loose chemicals 254 within a flexible reaction container being inserted into open pouch 176 of a conformable wrapping 194 before sealing the top of the pouch 176 during the forming sequence illustrated in FIG. 9A. Given the finished wrapping 270 of FIGS. 10 and 10C, the user squeezes the pouch 176 to break water bag 252. Reaction between the water and chemicals 254 causes the area of the body 8 touched by pouch 176 to become cold (or hot if exothermic materials are substituted). In some instances it is advantageous to include an insulator sheet at the backside of the pack 250. This provides a pack with two rates of heat transfer. Thus after the fast cooling or heating side of the pack 250 has been in place for 10 or 15 minutes, the wrapping may be undone, the packet reversed in its pouch, and the wrapping rewrapped to place the insulated side, slower heat transfer next to the skin. This enables continuous treatment while avoiding over-chilling or frostbite or over-heating from prolonged contact with the higher rate heat-transfer sides thus to void thermal injury.

Figure 10A:
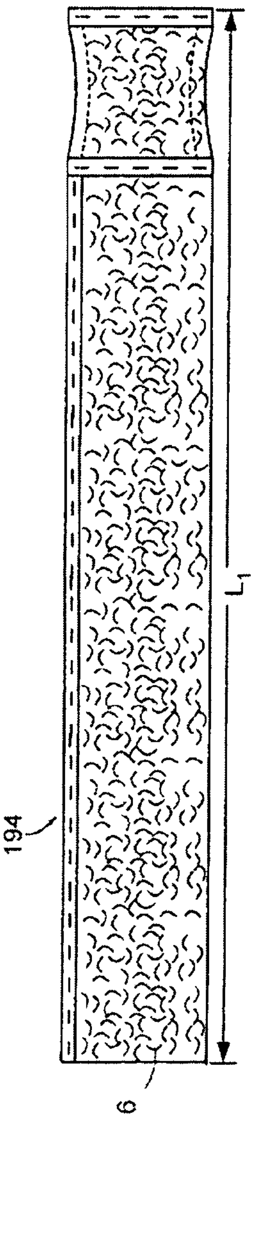
FIG. 10 is a partial perspective view and FIG. 10A a plan view of the finished embodiment produced by the step of FIG. 9B.
FIG. 10B is a partial diagrammatic side view in smaller scale of the step of inserting a preformed, breakable water bag and loose chemicals during the process illustrated in FIG. 9A to enable an endothermic or exothermic reaction in the pouch of the wrapping of FIG. 7B.
FIG. 10C is similarly a partial side view of the finished embodiment of FIG. 10B.
Figure 10B:
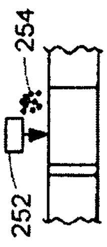
Figure 10C:
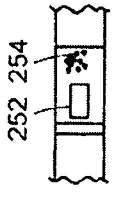
Figure 10:
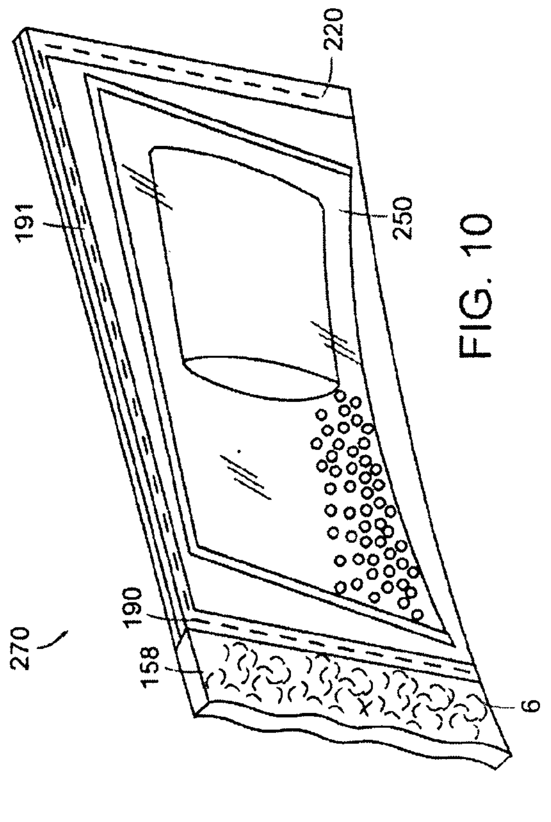

For another class of embodiment, a rupturable bag of water 252 and loose chemicals 254 are directly inserted into pouch 176 of the wrapping 194, as shown by FIG. 10B, to produce the completed wrapping 270 shown in FIG. 10C. For example, for a cold pack, ammonium nitrate is the loose chemical 254 in the water-tight pouch 176 of the wrapping 270. Upon breaking water pack 252 an endothermic reaction, proceeds with the sealed pouch 176 of the wrapping 270 serving as the reaction chamber. In another embodiment, loose calcium chloride or magnesium sulfate is the loose chemical, and an exothermic reaction proceeds with water released from the water pack 252, to heat the treatment area. Other embodiments may use other chemicals as the loose chemical for endothermic or exothermic reactions, or additional chemicals as buffer agents to slow the reaction for extending the life or reduce the intensity of the thermal treatment.

Figure 11:
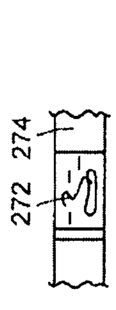
FIG. 11 is similarly a partial side view of an embodiment of FIG. 7B containing a preformed gel in the pouch of the wrapping.

An additional class of embodiments made for instance with the apparatus and process described with respect to FIG. 7B is illustrated in FIG. 11. A gel pack 272 is inserted in the pouch 176 of the wrapping 194 for reusable thermal treatment. The user simply heats the gel pack 272 with its extended wrapping 274 in a microwave oven for hot treatment or cools the gel pack 272 with its wrapping 274 in a freezer for cold treatment. In other cases, the pouch walls define the containment of loose gel or particles that when heated or cooled perform the desired thermal therapy.

Figures 12, 12A:
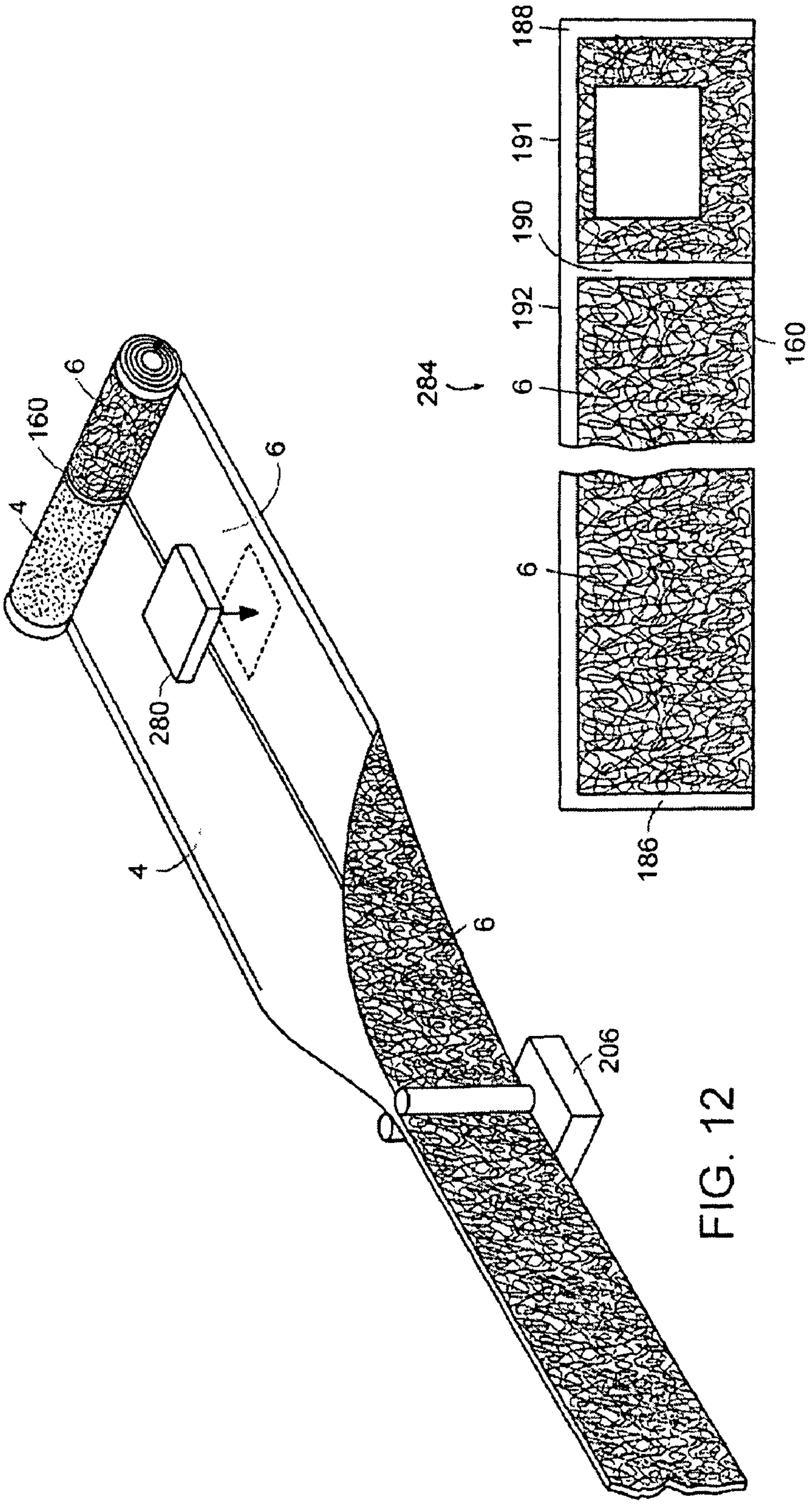
FIG. 12 is a perspective view illustrating a portion of the process employed to make the embodiment of FIG. 12A.
FIG. 12A is a plan view of a wrapping made by the process illustrated in FIG. 9A having a window cut out in the pouch area.
Figure 12B:
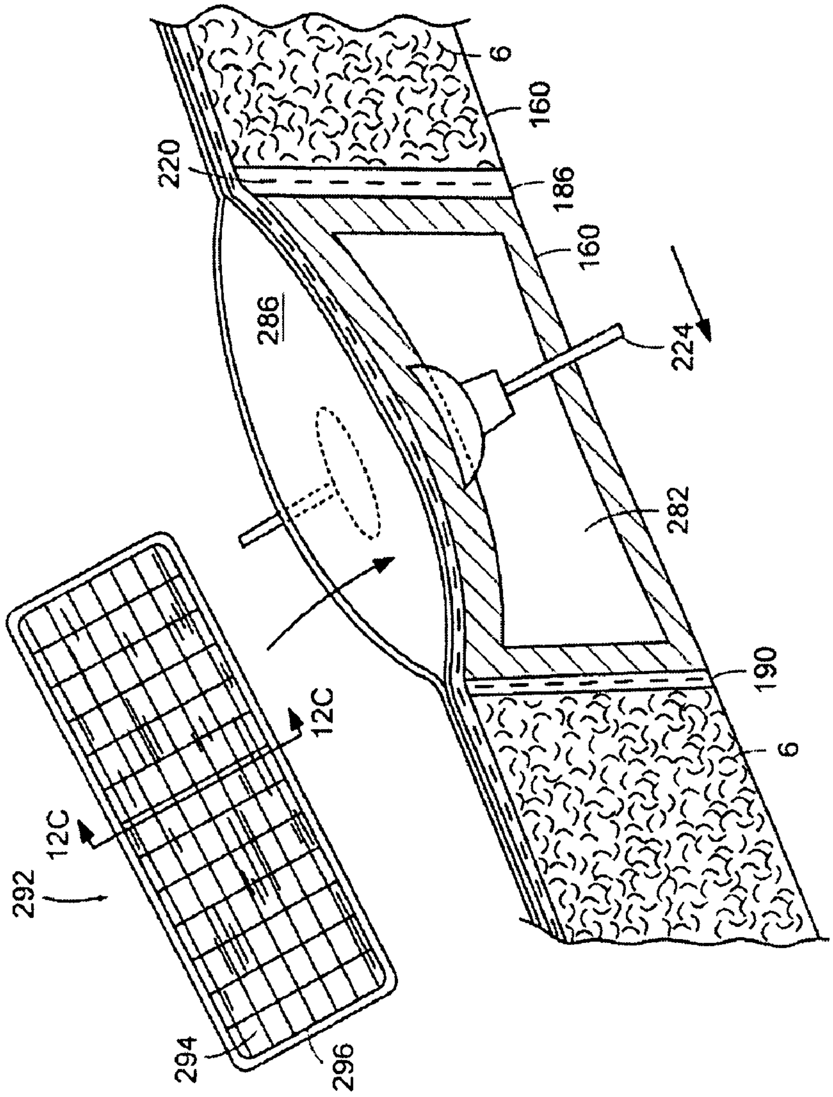

A modification to the continuous assembly process of FIG. 9A, shown in FIG. 12, adds the important step of die stamping, using die stamp 280, to create an open window 282 in the pouch area on the loop side. This forms a pouch 286 with window 282. The window 282 is formed before folding the composite pre-formed material 150. The resulting product 284 is illustrated in FIG. 12A. The window 282 on the user side of the pouch 286 enables contents held in the pouch 286 (see FIG. 12B) to directly contact the treatment area. These provisions enable forming economical embodiments, for instances, of combined wound dressings and self securing wrappings. The window 282 on the outside layer of the pouch 286 enables holding larger items in the pouch 286 than is permitted by the geometry of the pouch 286 itself, by enabling protrusion through the window 282 of an enlarged portion of an inserted pack 250 or device. The window 282 also enables access to tubes or electrical connections for various medical and monitoring procedures. Given the window 282, FIG. 12B illustrates insertion of a device 290 during in-line manufacturing. The separator system 224, such as a suction cup or pincer pair, grips the portion of the side of the pouch 176 above the window 282 to spread open the mouth of the pouch 176 for insertion of desired contents, such as the wound dressing 292 shown.

Figure 12D:
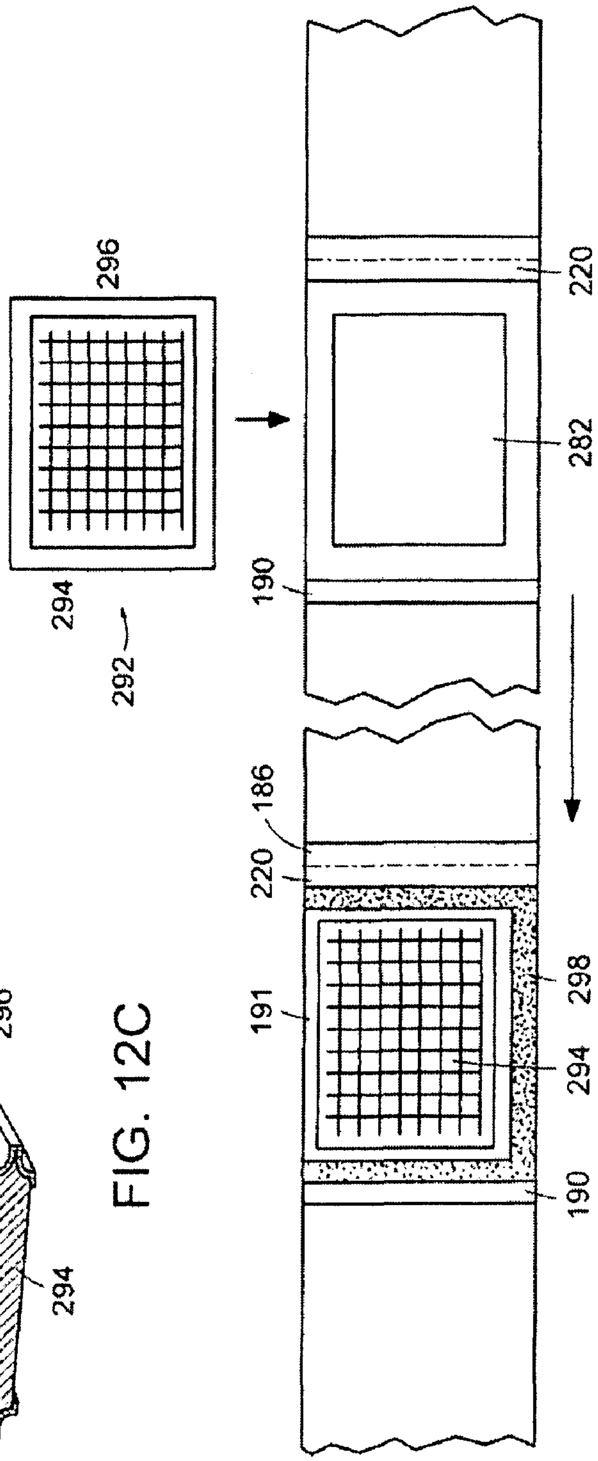
FIG. 12D is a side view of the continuous composite sheet during the process illustrated in FIG. 12B and subsequent sealing of the gauze pad.
Figure 12C:
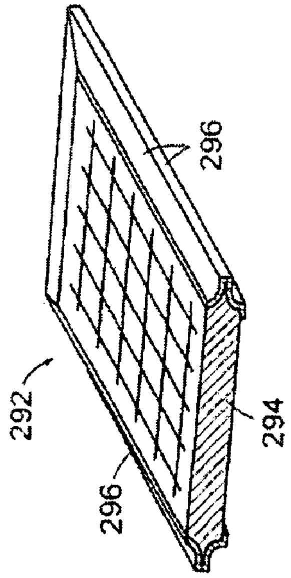
FIG. 12C is a partially cutaway perspective view of the treatment insert.
Figure 12E:
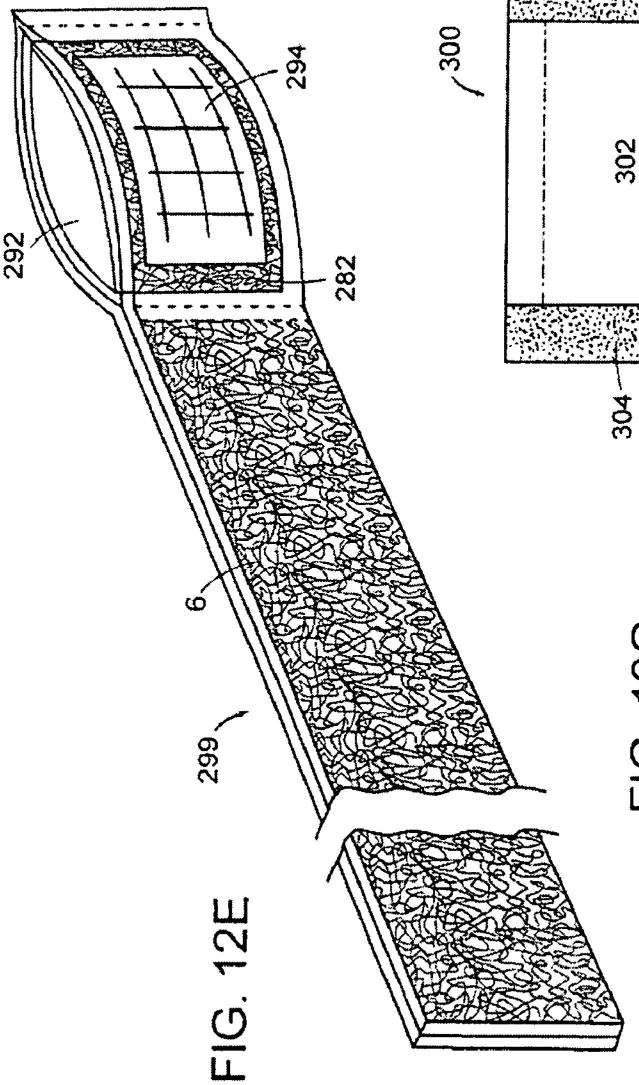
FIG. 12E is a perspective view of the finished embodiment produced according to FIGS. 12B, 12C, and 12D.

Dressing 292 held within the pouch 286 is positioned to contact a wound or incision through the window 282, as illustrated in FIGS. 12C-12E. Referring to FIG. 12E, treated rectangular gauze pad 294 is surrounded by a thin plastic flange 296 about its perimeter. The gauze pad 294 is coated or has embedded in it drugs or agents to help seal a wound, speed its healing, administer anesthetic, etc. One example is fibrin powder coated on the gauze pad in concentration selected to accelerate blood clotting and lessen blood loss from a severe wound. The thin plastic flange 296 stabilizes the pad 294 within the pouch perimeter so that the gauze does not slip from window 282 during storage or use. The gauze insert 292 may be prevented from slipping by sizing the insert 292 to fit snugly in the pouch 286. In another case the flange 296 is appropriately welded to wall portions of the pouch 286. For instance, the top portion of the flange 292 is sealed along with weld flanges 158 and 164 to form weld 191 along the top of the pouch 286 by weld sealer 216 in the process described with respect to the assembly system 200 of FIG. 9A, see also FIG. 12D. For additional security, an additional welding step employing a suitably shaped heat seal die, or dies, not shown, can heat seal or otherwise weld some or all of the remaining three sides in the area 298 as illustrated in FIG. 12D. Such welds are facilitated by selection of the resin of flange 296 to be weld-compatible with the resin layer forming the inside surfaces of the pouch 286.

Figure 12F:
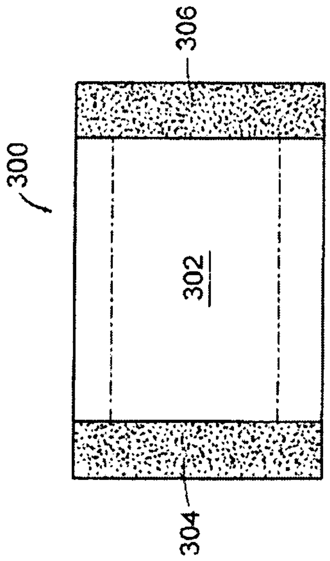
FIG. 12F is a plan view of a pressure sensitive cover that may hygienically seal the wound dressing until usage.
Figure 12G:
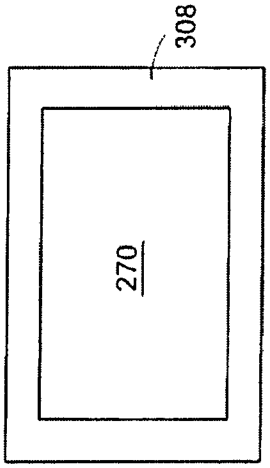
FIG. 12G is a plan view of the embodiment of FIG. 12D folded and inserted in a sterile pack.

A finished conformable, self-securable wrapping 299 is illustrated in FIG. 12E with the treated gauze pad 292 showing through the window 282. To hygienically protect the wound dressing 294 inside the wrapping 270 prior to usage, a cover 300 (see FIG. 12F) with pressure-sensitive borders may be applied over the window 282 of the pouch 286. This pressure-sensitive cover 300 has an impermeable middle closure section 302 and two pressure-sensitive adhesive ends 304,306 (or a full perimeter bordered with the adhesive as suggested by the dashed lines). The cover 300 is removably applied to the wrapping 270 so that the adhesive holds the cover 300 in place. In the example shown, adhesive end 304 is placed over the weld 220 and adhesive end 306 is placed over the weld 190. In other cases loop-engageable hooks 4 are associated with the pressure sensitive material to provide secure attachment and enable the adhesive or conformable material to be formulated primarily to enable formation of a sound protective seal. For storage prior to use, the wrapping 299 can be folded into a compact form and placed in a sealed bag 308, as illustrated in FIG. 12G, which is sterilized, such as by exposure to suitable radiation.

Figure 13A:
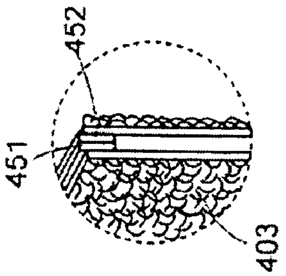
FIG. 13A is a magnified view of a portion of FIG. 13 showing a joint at the upper edge.
Figure 13:
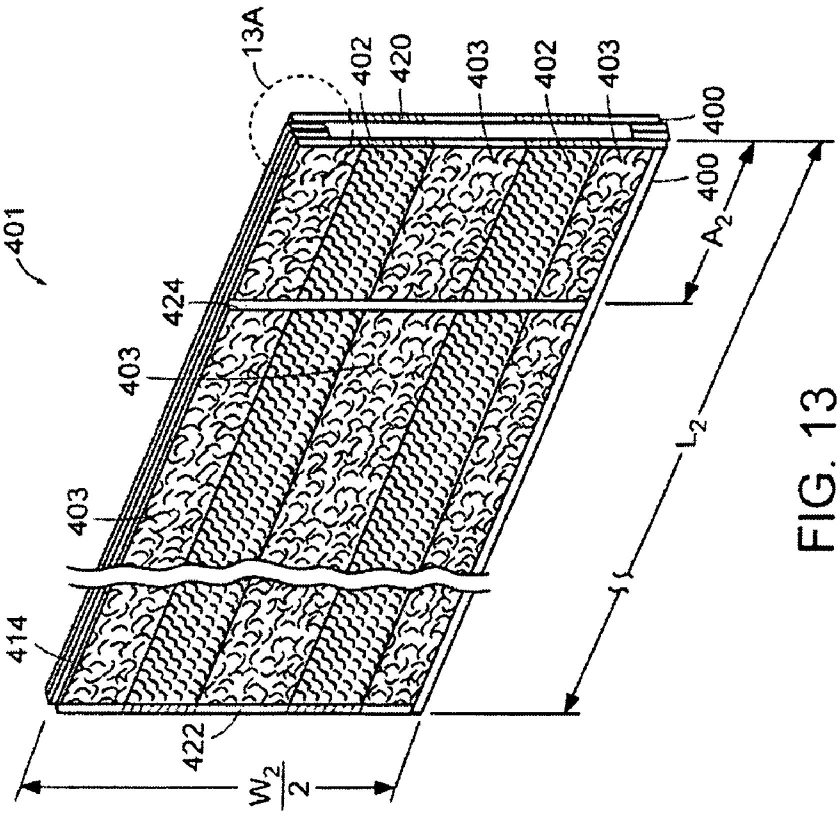
FIG. 13 is a perspective view of another extended length, conformable, self-securing, functional wrapping.

In FIG. 13 a breathable, conformable, self-securing wrapping 401 is shown, which is useful, for instance, as a medical or veterinarian wrapping to be maintained in place for an extended time. The breathable feature can prevent discomfort or harm that might occur from prevention of escape of moisture from or access of air to the region covered. This wrapping 401 represents a class of embodiments related to the of wrap 194 may be inserted into the wrapping 401 of FIG. 13. These including sealed bags or devices such as cold packs, hot packs, gel packs, air bladders, monitoring instruments, and wound treatments.

Figure 14B:
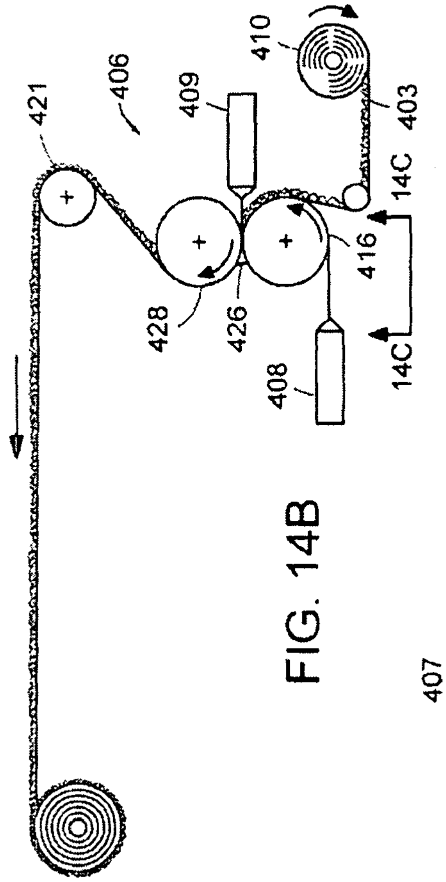
FIGS. 14, 14A, 14B, and 14C illustrate the machine and process for forming the material of FIG. 13.
Figure 14:
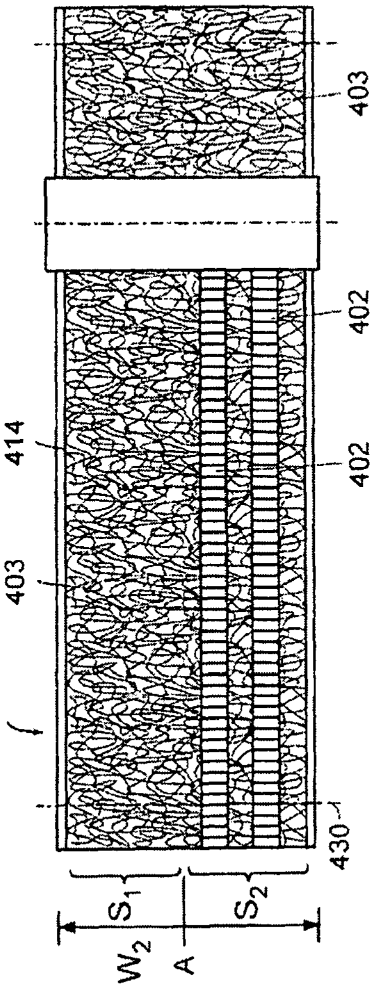
Figure 14C:
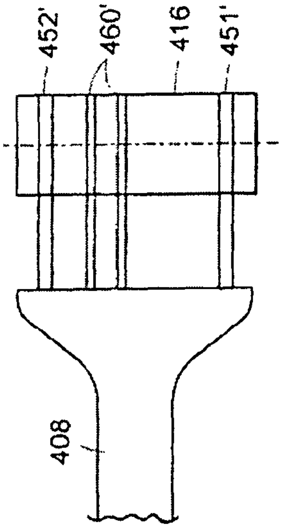
Figure 14A:
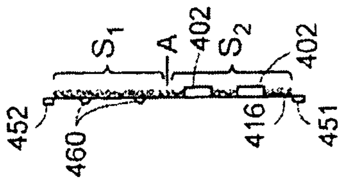
Figure 15:
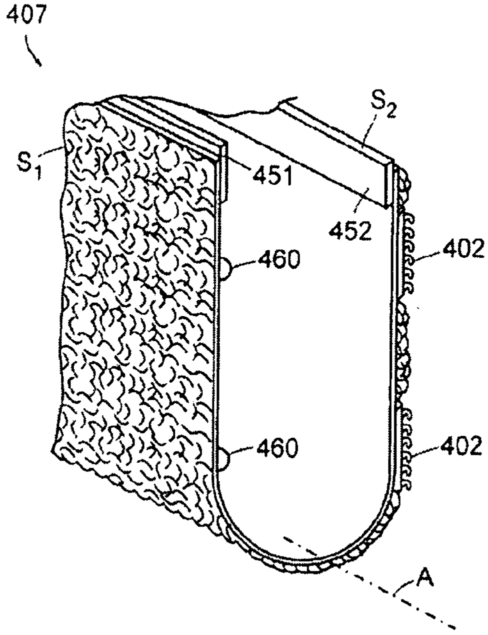
FIGS. 15 and 15A are perspective views showing, respectively, how the sheet is partially and completely folded together in forming the wrapping of FIG. 13.
Figure 15A:
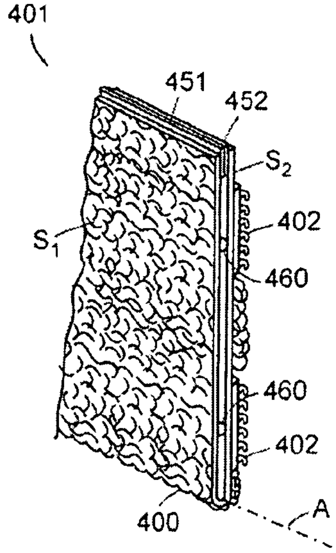

In FIG. 13, a porous non-woven loop material 403 such as L3310 non-woven, available from Velcro USA, may be employed to form the wrapping 401. Referring also to FIGS. 14, 14A and 14B, a hook and loop composite 407 is formed using two discrete bands of hook 402, tacking beads 460 (shown in FIG. 14A) and edge welding flanges 451,452. These are directly applied by in situ lamination and forming in this embodiment. The formed continuous hook and loop composite 407 is adapted to be folded about a fold line A that is positioned with respect to beads 460 and hook bands 402 so that when the composite 407 is folded, the resin beads 460 register with the backs of hook bands 402 (as illustrated in FIGS. 15 and 15A), and weld flanges 451 and 452 on opposite edges can be welded together to close and seal the folded material 407.

The parallel tacking beads 460 on the back-side of the loop material 403 enable tack welding by the side seal bars (e.g., 212,214 in FIG. 9A) at opposite ends of the wrapping 407 and at any transverse boundary of the pouch 176 being formed. The preformed loop material 403 of FIGS. 13, 14 and 14A extends the full width of the material between the welding flanges 451,452. The loop material 403 is of open construction, i.e. there is no continuous resin lamination on its backside, so that the loop material 403 is air permeable. Thus, one full side, $S_1$, of the folded material is permeable exposes hook-engageable loop 6. On the reverse side, $S_2$, as shown in FIG. 14A, the area is also permeable except at the locations of the two bands 402 of hooks 4. These hook bands 402 are formed in the machine direction from extruded bands of resin laminated in situ directly to the loop surface material 403, and molded into hooks 4 or hook preforms by registering mold cavities in a molding roll 428.

An apparatus and process for making the wrapping 407 will be described with reference to FIGS. 14, 14A, 14B and 14C. An extruder 409 provides to the nip 426 molten strips of resin of width corresponding to the width of the desired two bands of molded hooks 402, see for instance, FIGS. 3 and 3A. A second extruder 408 provides strips of resin for the two tacking beads 460 and the two marginal weld flanges 451, 452. As illustrated in FIG. 14C, extruder 408 applies its four bands of resin to bottom roll 416 which is subsequently engaged by the backside of loop material 403. The preformed air permeable loop material 403 is led from a supply roll 410 to a bottom roll 416 of a calender stack 406. Completion of the in situ lamination is achieved by the pressure in the calender nip 426 formed by pressure roll 416 and mold roll 428. The bands of resin 460' correspond to tacking beads 460 and bands 451' and 452' correspond to welding flanges 451 and 452. As the loop material 403 passes through the nip 426, the two resin bands 451' and 452' are laminated to the air permeable material 403 and extend from its edges as free flanges of plastic web formed by suitable formations in the rolls 416, 426. Resin of the additional bands of resin applied above the loop material 403 by extruder 409 enters mold cavities in mold roll 428 to form hook bands 402. The hook bands 402 comprise hooks 4 or hook preforms molded integrally with a base resin layer that is in situ laminated to the loop web 403 by the action of the calendar nip 426. After cooling, the finished wrapping material 407 is removed from the mold roll 428 and rolled up in supply roll 430, in which form it is delivered to the wrapping forming machine (e.g., 200).

As illustrated in FIGS. 13, 14 and 14B, in manufacture, the non-woven fabric sheet 403 of running length, bearing a field of loop-engageable loops 6 on one side, is folded along line A. The front face of the assembly 401 in FIG. 13 (side $S_2$ in FIGS. 14 and 14A) has two separate bands 402 of hooks 4 while the remainder of the front face and the entire back face $S_2$ of the sheet 407 comprises the air-permeable non-woven loop fabric 403. Using the machine 200 (referring to FIG. 9A), the backings of both faces $S_1$ and $S_2$, in the inside of the fold A, are sealed together at seal lines 422, 424 and 420 at the intersections of the machine direction tacking beads 460 with the heat seal bars 212 and 214. The top is sealed together by welding weld flanges 451 and 452, to complete a closed pouch 418 with width $A_2$ and height $W_{2/2}$, and the wrapping 401 is cut to a length $L_2$. As with the embodiment of FIG. 7D, the pouch 418, when filled, forms a bulge that is useful to press the contents of the pouch 418 against a body part 8 (as illustrated in FIG. 8 and FIG. 8A). The wrapping 401 fastens to itself by touching the non-woven loop material 403 to the hook surface 4 as illustrated in FIG. 8. This embodiment, as was the case of the embodiment of FIG. 7D, is made using a continuous roll process to form the composite base material 407, as illustrated in FIG. 14B, and then a start/stop in-line process using the machine 200 to fold, seal, fill the pouch 418, and cut, as illustrated in FIG. 9A.

In some cases, the pouch 418, as formed by the machine 200, is not completely sealed at its making. In these cases, the pouch 418 is most suitable for holding objects such as preformed hot and cold packs, gauze and absorbent materials, air or liquid bladders, or other devices and large items.

FIGS. 13-15A have thus illustrated a continuous calender roll process for forming a porous composite wrapping material 407 from which breathable, conformable, self-securing wrappings 401 are formed, and a process which then folds and seals the hook-bearing loop material 407 together employing parallel, longitudinal tacking beads 460 of thermoplastic resin to integrate the folded sides of the material 407 at localized regions at transverse sealing jaws 212, 214. The clamping pressure of transverse sealing jaws 212,214 where engaged, melt and fuse corresponding portions of those thermoplastic, longitudinal beads 460 to the opposite material of hook strips 402. Conditions can be maintained that force the resin of the beads 460 to weld to the porous material 403, or to also penetrate through the porous material 403 to weld the beads 460 to the backside of the hook strips 402, while encapsulating fibers of the preformed web 403 that lie in between. The cross-section view of FIG. 15 is taken during folding. FIG. 15A shows the material 401 folded, prior to welding, showing the alignment of the tacking beads 460 with the backside of the hook bands 402. The apparatus 200 of FIG. 9A may be employed to form the wrapping 401. As before, seal jaw 212 is typically twice the width of seal jaw 214 to enable the weld to be bisected by the cut-off station 202,230 to provide end heat seals 422,420 for opposite ends of two successive wrappings 401 being formed by the in-line process of the machine 200.

The resultant wrapping 401 of composite material 407 (FIG. 14) provides a breathable surface against the skin, and is highly flexible and fabric-like. Conformable, self-securing wrappings 401 formed in this manner have numerous benefits. With appropriate choice of loop materials 403, a pouch 418 formed of this material 403 is useful to apply medicinal or therapeutic agents through the thickness of the loop material 403, such as prescription drugs for transdermal drug delivery or topical treatment. Useful, such as in the battlefield to stop blood flow, are wound dressings formed as above, in which a blood coagulant is incorporated in the material 403 of a wrapping 401 itself, or on gauze or other contents carried in the pouch 418.

Figure 15B:
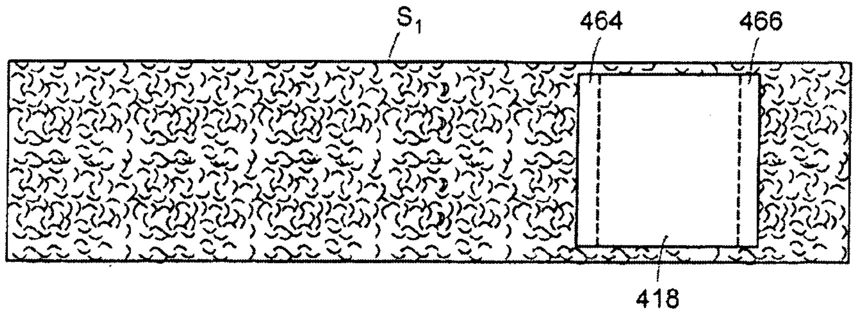
FIG. 15B is a plan view of a completed wrapping and FIG. 15C shows a side view of a treatment patch attached to the exterior loop surface of the wrapping of FIG. 15A.
Figure 15C:
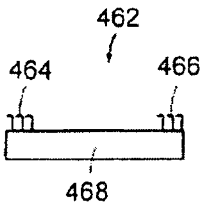

Referring to FIGS. 15B and 15C, a wound dressing 462 can be attached externally to side $S_1$. The wound dressing 462 is an exterior gauze patch assembly that includes gauze material 468 and two rows 464,466 with hooks 4 that can be secured to the exterior loop material 403 of $S_1$. A blood coagulant can also be incorporated in the gauze material 468.

Figure 38:
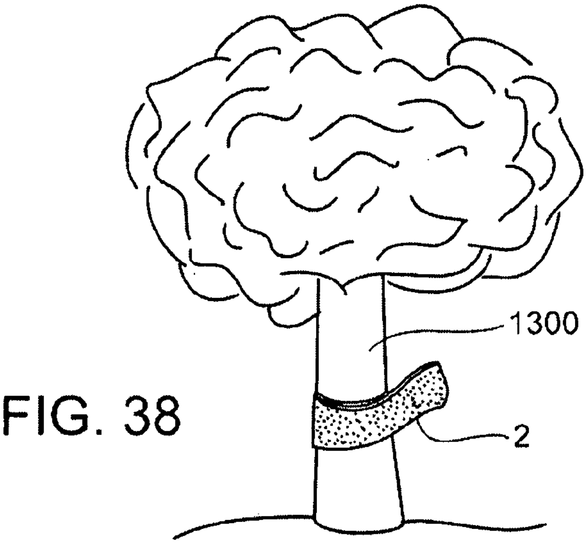

The material 403 of the wrapping of FIGS. 14 and 15 is sufficiently soft to protect delicate plant and tree material (such as tree 1320 shown in FIG. 38) about which it is wrapped. As in previous embodiments, this flexible wrapping 401 with pouch or attached patch, or impregnated treating substance can be made to any selected length.

Another embodiment is a wrapping with pouch as just described sold in unfilled condition, for use in the case in which the end user inserts a suitable pack or device, or attaches a treatment patch to the exterior via mating fasteners, to accomplish a desired treatment or task. In this case the pouch of the wrapping is left empty during formation, and the top of the pouch is left open (seal jaws 216 not being employed at the pouch during production). Advantageously, strips of opposing surface fastener materials are provided at the mouth of the pouch to permit repeated opening and closing. In other cases, the pouch of the wrapping is used to store an unused treatment patch, such as within a sterile wrap, and for activation and use, the user withdraws the patch, removes it from its wrapping and applies it via its own hook fasteners to a loop portion of the fabric adapted to be held against the skin.

In another case, an unfilled wrapping is provided to a packer for filling in a fill-and-seal machine. In this case a magazine of the empty wrappings is provided in a continuous roll. The continuous wrapping is led into a conveyor which drops the product into the empty pouch after which the pouch passes through a top sealing mechanism. Also, continuous rolls of the wrapping material may be provided to hospital or emergency care facilities, with provisions e.g. for dispensing fixed lengths or enabling selective cutting to desired length of preformed cut locations, see previous discussion above concerning the feature of a series of transverse weld lines suitable for cutting to form wrappings of desired length.

In other embodiments, pressure-sensitive sealing material is provided at the sealing flanges for sealing the wrapping.

In other embodiments, the fold line A is located off-center, providing a single layer at the top to serve as a sealing flap, and/or to facilitate opening of the pouch for insertion of the desired contents.

Figure 16A:
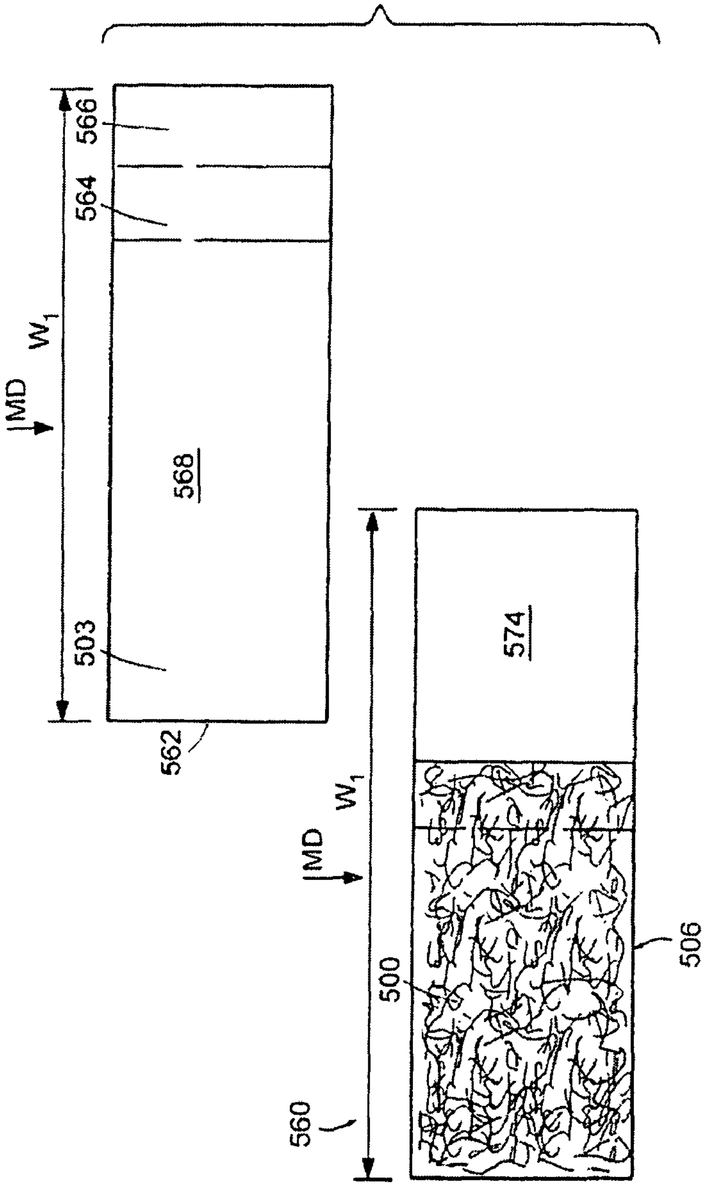
FIG. 16A is a plan view of two composite sheets of preformed starting material with engageable hooks and loops respectively.
Figure 16B:
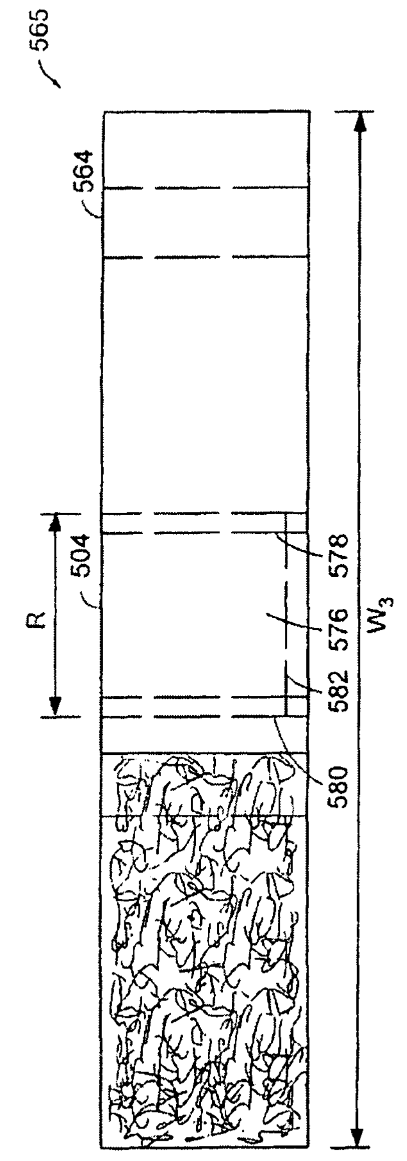
FIG. 16B is a plan view of the two sheets of FIG. 16A joined together.

Referring now to FIG. 16A, two continuous, composite wrapping materials 560,562 for forming conformable, function-delivery wrappings, are produced using, respectively, the apparatus and calender process of FIGS. 2 and 2A, to form a loop-bearing component 70, and the apparatus and calendar process of FIGS. 3 and 3A to form a hook-bearing component 74. The two components 70 (560) and 74 (562) are then joined to form a wrapping 565. Component 560 includes a loop band 500 that is in situ laminated to a calendered layer of resin 574. Only a small margin 506 of the back of the loop material 500 over-laps the calendered resin band 574, and the resin band 574 extends beyond the loop material 500. This extension of the resin band 574 is used to form one side of a pouch 504 of width R. The material 560 is cut transversely to machine direction MD to a length $W_1$. While web 560 has a loop section 500, and calender rolled sheet 574 side-by-side, in alternate embodiments the loop section 500 may instead cover the entire calendered resin to achieve more adjustability for the wrapping.

Web 562 is created using the apparatus and process illustrated in FIGS. 3 and 3A and also is cut such that its length $W_1$ is transverse to machine direction MD. Web 562, of roll-formed resin, has a hook strip 564, and a sheet-form resin flange 566 lying outwardly beyond the hook strip 564. The remainder of web 562 is calendered resin sheet 568, of length to form the other side of a pocket and a section of the body of a wrapping.

Figure 16C:
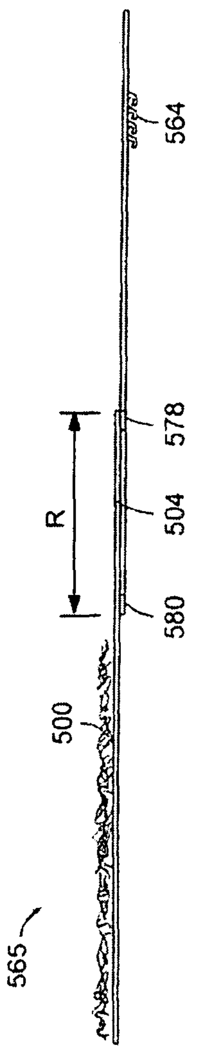
FIG. 16C is an edge view of the joined sheets of FIG. 16B.
Figure 16D:
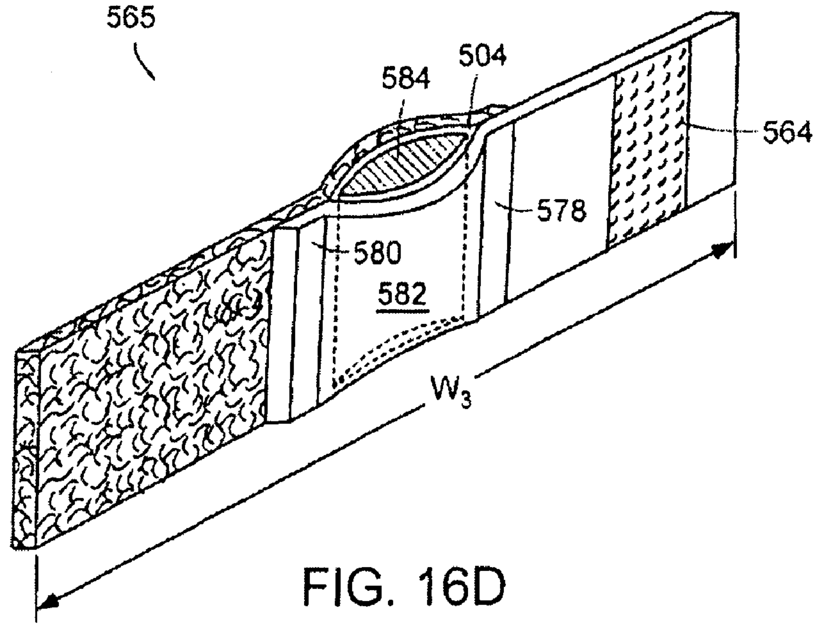
FIG. 16D is a perspective view of one embodiment having the general construction of FIG. 16C.

Referring to FIG. 16C, the two components 560, 562 are joined together with an end overlap such that the hook section 564 faces down and the loop section 500 faces up. Transverse welds 578,580 are located at respective ends of each of the overlapping component, the amount of overlap thus determining the width R of the pouch 504. The resulting wrapping 565 has an overall length $W_3$. FIG. 16D shows the joined webs 560,562 having a bottom weld 582 forming the bottom of the pouch 504 and the top of the pouch 504 left open. A functional bag 584 (e.g., a cold pack) is inside the pouch 504. Given a typical calender stack with width $W_1$ of 24 inches, a pouch width of 4 inches, and welds 580,578 of width 0.5 inch, then $W_3$ can be 43 inches when using the full width capability of the calender stack to form the two components 560,562. Wider machines can form correspondingly longer wrappings.

Figure 16E:
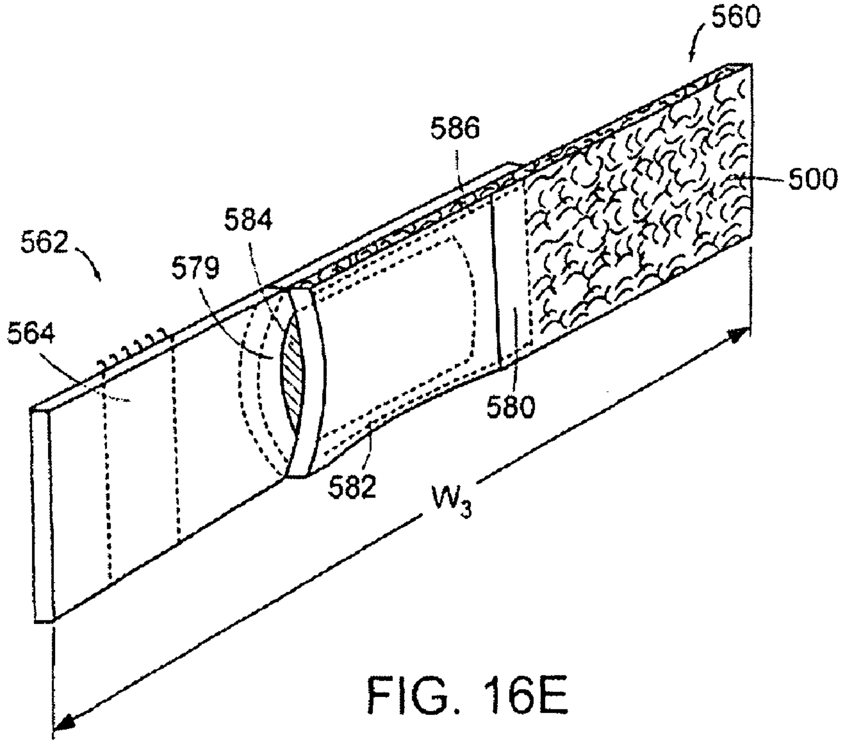
FIG. 16E is a perspective view of another embodiment having the general construction of FIG. 16C.

In another embodiment 562, illustrated in FIG. 16E, weld 578 is not created while a top weld 586 is created, extending in the direction of the length, across the top of the overlap of sheets 574 and 568. Thus, a pouch 506 is open from the side, side opening 579, and closed from the top. This allows a functional bag, device instrument or material to be placed in the pouch 506 from the side. When the wrapping 562 is wrapped around an object 8 with the loop surface 500 on the inside, the wrapping 562 covers the side opening 579 to prevent the pouch contents from slipping out.

In other embodiments related to the descriptions of FIGS. 16D and 16E, a non-woven material with acrylic binder having an elastomeric characteristic in the cross-machine direction is employed as a stretchy loop material 500. Such a material and other stretchy loop materials are described in PCT/US01/08100, published on Sep. 20, 2001, which is hereby incorporated by reference in its entirety. In such an embodiment the wrappings 562,565 of FIGS. 16D and 16E are stretchy in the direction of the length $W_3$ of the conformable wrapping (in other words, in the cross-machine direction only during the prior in situ lamination step in which the composite was formed). The elastic stretchiness achieved in the direction of the length of the wrapping enables the user to tighten the wrapping and fasten it, to permit freer motion of the wrapped object while ensuring good contact between functional region of the wrapping and the area to be treated.

Figures 17A, 17B, 17C:
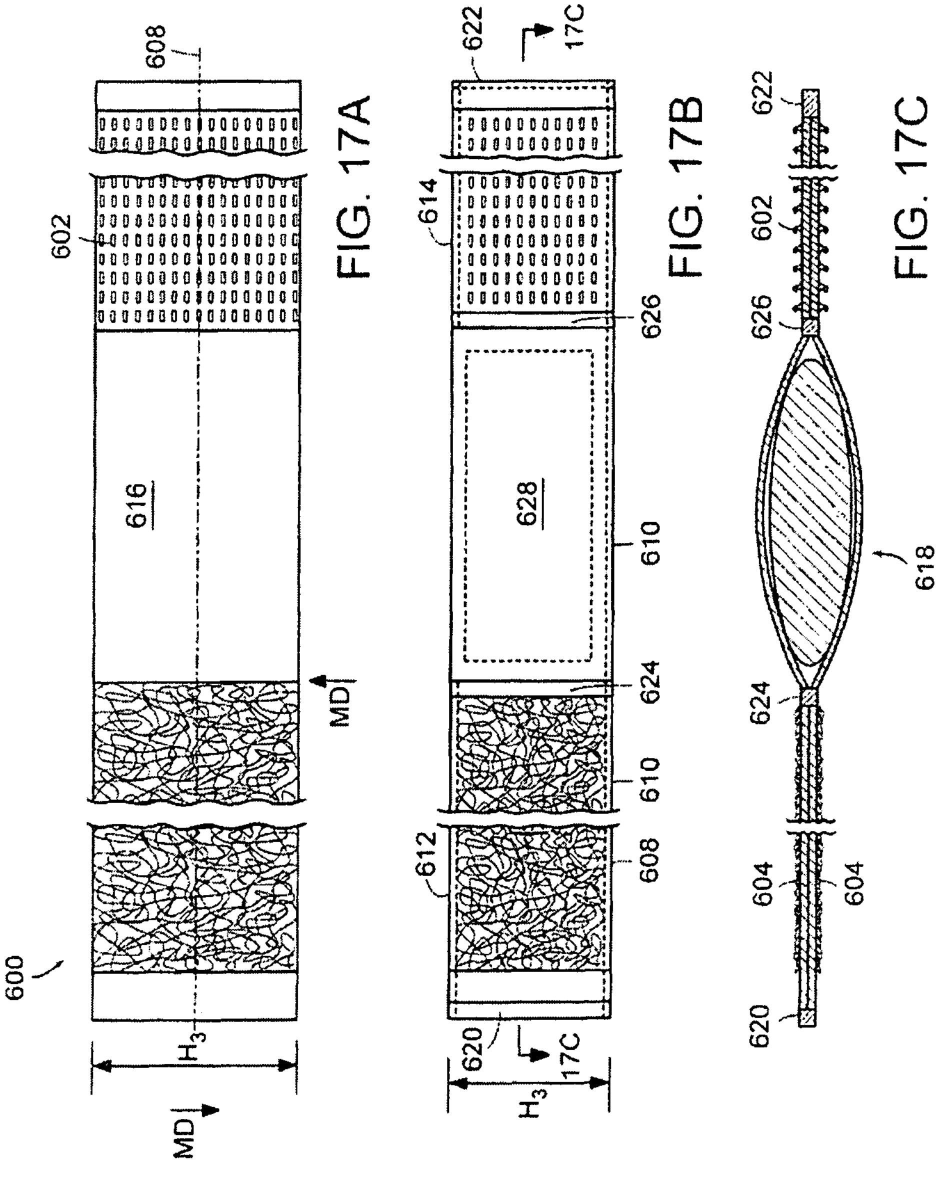
FIG. 17A is a plan view of a continuous composite sheet having bands of engageable hooks and loops.
FIG. 17B is a plan view of the sheet of FIG. 17A folded and welded to itself.
FIG. 17C is a diagrammatic cross-sectional view of the wrapping of FIG. 17B.
Figure 17D:
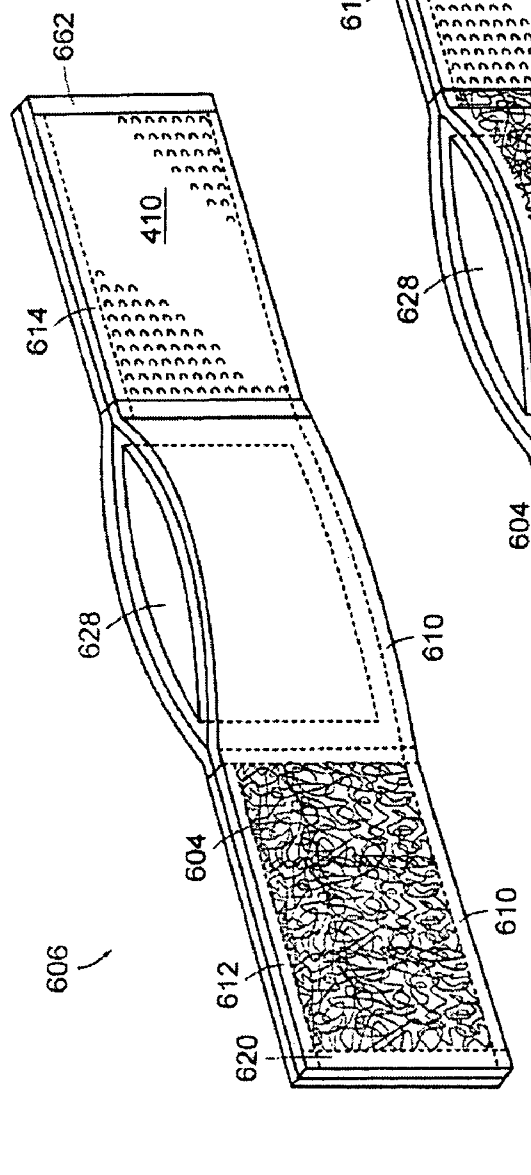
FIG. 17D is a perspective view of one embodiment having the general construction of FIG. 17C.

FIG. 17A shows a roll-formed wrapping 600 with a hook band 602 and a loop band 604. A sheet (not shown) to form the wrapping 600 may be formed using the machine and process illustrated in FIGS. 4 and 4A, or by the machine and process of FIG. 4D. After forming the continuous material, an individual wrapping 600 extending transversely to the machine direction MD is cut along transverse cut lines from the continuous sheet, the dimension of the cut material in the machine direction, $H_3$, being twice the final width $H_3$ of a finished wrapping 606 shown in FIG. 17B. This wrapping 606 is created by transversely folding the sheet 600 of FIG. 17A about center line 608, which extends transversely to the machine direction MD. The wrapping 606 has a hook section 602 and a loop section 604 each of which lies on both sides of the wrapping 600. The folded sheet 606 is welded at weld 610 along the fold line 608 and, at the opposite, open edges, two aligned welds 612,614 seal the top. The welds 612,614 are separated by a central pouch area 616 that is left open. A pouch 618 is located in the pouch area. End welds 620 and 622, extending in the original machine direction MD, join ends of the folded sheet 606 together, while intermediate welds 624 and 626 also in the machine direction define the ends of the pouch 618. The top of the pouch 618 may be left open so that a user may place a functional bag or device 628 inside, see FIG. 17C for a cross-sectional view and FIG. 17D for a perspective view of this embodiment.

In some realizations of this and other embodiments, the base fabric of the loop material 604 includes thermoplastic material, such as thermal adhesive fibers or thermoplastic binder distributed through the thickness of the material. This renders the loop material 604 capable of being heat-sealed to itself, while preserving its porous character in regions beyond the heat seal. In such cases, referring to FIG. 17C, the loop material 604 is not backed with a roll-formed sheet layer, so that the wrapping may be air-permeable.

Figure 17E:
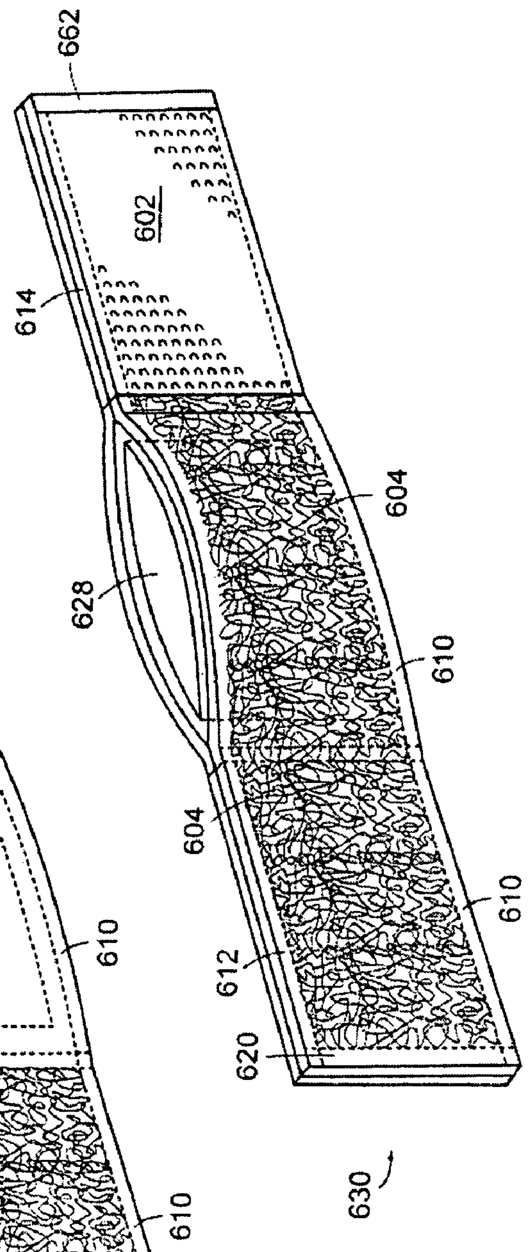
FIG. 17E is a perspective view of another embodiment having the general construction of FIG. 17C.

The embodiment 630 of FIG. 17E is similar to that of FIG. 17A except that loop material 604 illustrated in FIG. 17E extends over the pouch area 616 to provide comfort against skin, and there is more loop area to engage the hooks 4 while fastening the wrapping 630. Thus a larger range of diameters of object 628 may be wrapped by a given wrapping 630.

Figure 18:
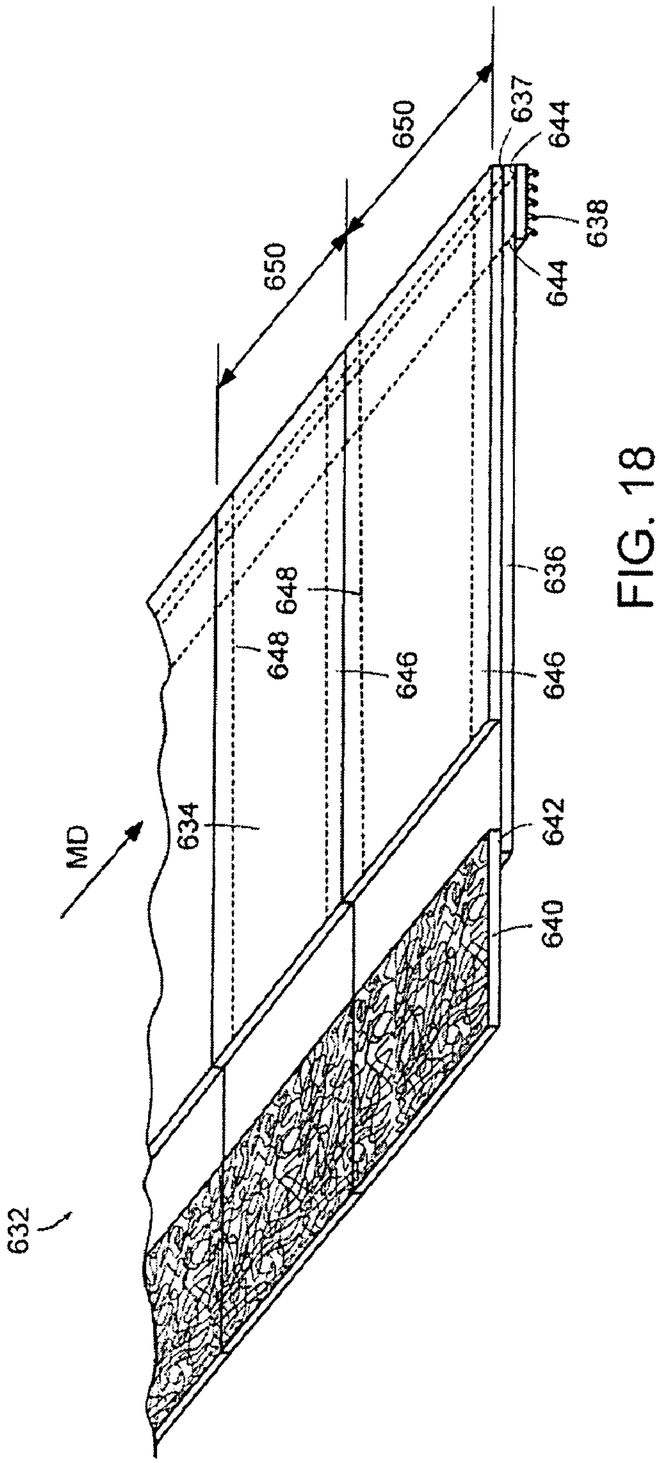
FIG. 18 is a perspective view illustrating forming a wrapping of another construction.

FIG. 18 illustrates a set of wrappings 632 formed with flat bag making equipment employing a set of continuous sheet-form materials. In FIG. 18, the wrapping 632 has a pouch and hook and loop components. The wrapping 632 provides for a cold pack or hot pack to be inserted into a pouch formed between sections of pre-formed plastic sheets 634 and 636, which may in this case be of biaxially oriented plastic film. Since sheet 634 touches the skin when the wrapping is used to hold the pouch against a body part 8, sheet 634 can be made using other, more skin friendly materials. Such materials include perforated plastic film and spun bonded TYVEK®, available from DuPont Chemical Company. In the structure of the wrapping, a top resin film or sheet 634 is joined to a bottom film or sheet 636 by weld 637. Hook fastener component 638 is a continuous hook fastener band made by calender molding thermoplastic resin such as by the process illustrated in FIGS. 3 and 3A. Loop fastener component 640 is a continuous hook-engageable loop band with a plastic backing made by calendering thermoplastic resin to the back of non-woven fabric with loops such as the process illustrated in FIGS. 2 and 2A, or the loop material may itself be heat-sealable by incorporating heat-sealable constituents such as heat-sealable fibers or binders as mentioned for the previous embodiment. Before the plastic sheets or films 634, 636 are joined, fastener components 640 and 638 are welded by a continuous weld process to the bottom sheet 636 along weld lines 642 and two weld lines 644, formed by heat and pressure as by heated rolling discs. The running top resin web 634 is then introduced in the machine direction as shown. Edge heat seals 646 and 648 extending transversely to the machine direction, which determine the repeat length, can be formed as radiant bead seals. For this purpose, a transversely extending cut-off knife is maintained very hot, such as about 700 degrees Fahrenheit. The radiant seal formed is a narrow bead, which may be no more than about 1/16 inch in width and very sharp. These seals are made when a unit is separated from the continuous material at cut-off and seal forming repeat length 650. An advantage of this construction is that hook/loop bands 638,640 may be quite narrow and economical. The preformed, oriented film or sheet providing the body of the conformable wrapping is also inexpensively fabricated. This process enables extended wrappings to be produced on common bag making machinery (such as RO-AN, Polystar, GN), of length corresponding to the maximum width capability of the machine.

Figures 19, 19A, 19B:
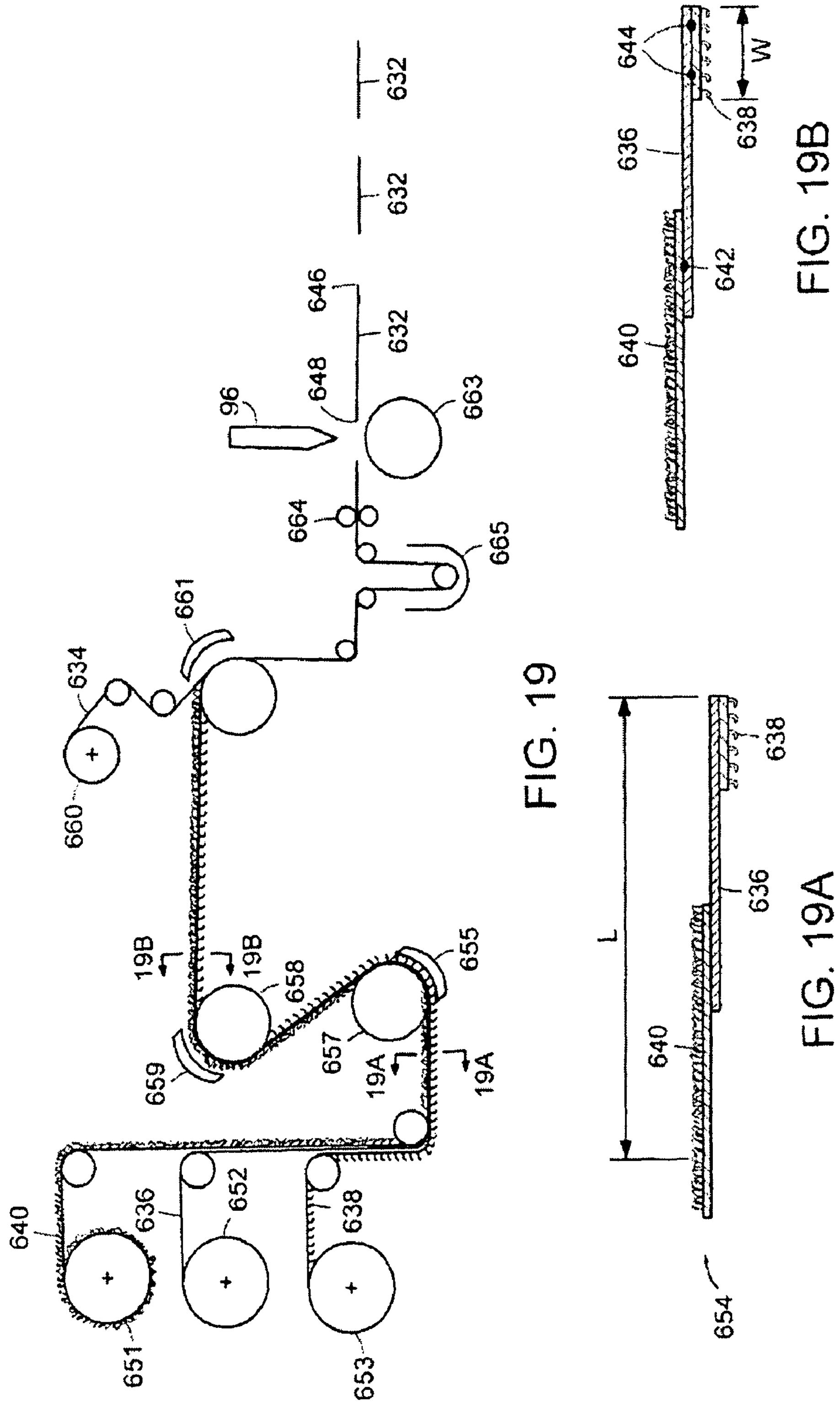
FIG. 19 is a side view of a flat bag sealing system for making the wrapping of FIG. 18.
FIG. 19A is a cross-section view of the continuous web without welds in the process performed by the system of FIG. 19.
FIG. 19B is a cross section view of the continuous web with welds in the process performed by the system of FIG. 19.

FIGS. 19, 19A, and 19B illustrate an apparatus and process for using common flat bag making machinery. At the beginning of the machine there are 3 supply rolls of continuous weld-compatible materials. Roll 651 carries non-woven loop material with thermo-plastic backing 640 (or the loop material is heat sealable without thermo-plastic backing), roll 652 carries back sheet 636, and roll 653 carries hook material 638. The webs from supply rolls 651, 652 and 653 are combined into a tri-component continuous web 654 as shown in FIG. 19A, employing thermal drag sealers 655 and 656. Each drag sealer 655,656 includes a nip formed by a round drum 657 or 658 and a heated drag profile (a member which slidingly engages the web with heat and pressure along a desired weld line). The heat, time, and pressure of the drag through the nip is requested to join two sheets through thermal welding.

The loop drag sealer 655 seals through the back web 636 into the backing of loop web 640 creating thermal seal 642 that joins webs 640 and 636.

A hook thermal drag sealer 659 seals the continuous hook web 638 to combined webs 640 and 636. In the preferred embodiment, two seal welds 644 are provided, FIG. 19B, one on each edge of the hook web 638.

Next in the process, a further supply roll 660 holds the weld-compatible front web 634. The material 634 may be biaxially oriented polyethylene, such as low density polyethylene, but can also be fibrous material such as Tyvek®, calender Tyvek®, or textured Tyvek®, or micro-perforated films that are skin friendly and enable transmission of moisture such as perspiration. A drag sealer 661 thermally seals front web 634 upon back web 636 by weld 637, shown in FIG. 18. Subsequently, a heated cut-off blade 662 severs the sheet against round anvil 663 transversely to machine direction at running length intervals while forming edge welds 646 and 648. A servo drive mechanism 664 moves the sheets along until they reach the cutoff blade 662. the anvil 663 rotates slowly as the sheet indexes to present a cool surface for each cut. The take-up dancer assembly 665 provides web inventory or film inventory so that the materials can progress with continuous motion past the drag sealers and with rapid intermittent motion the high temperature, radiant heat cut-off cycle.

In addition to providing a carrying pouch defined between to and back webs 634 and 640, the wrapping 632 can be formed as a compressive medical wrap, with integrated hook and loop closures that can be very inexpensive and disposable after single use.

In an alternative process, the material 46 formed according to FIGS. 1E and F may be employed in the machine, with or without the addition of the top sheet, depending upon the desired use.

Figure 20:
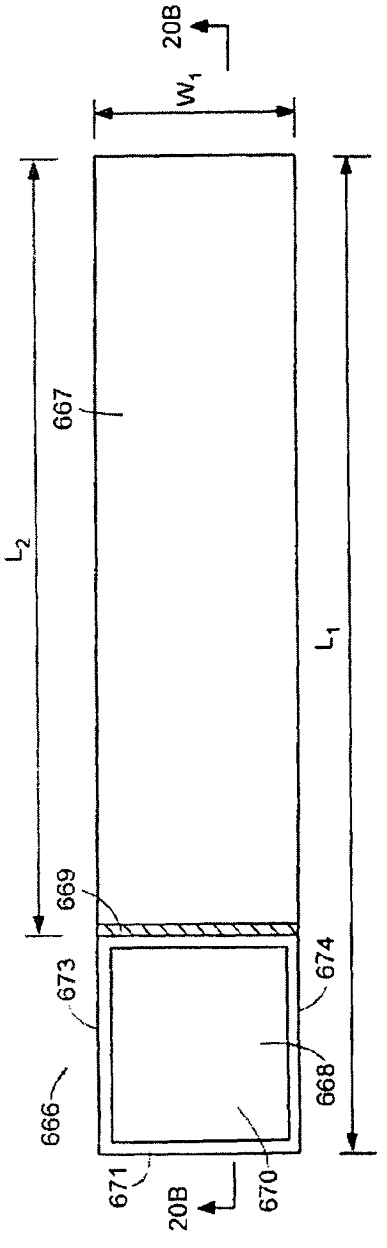
FIG. 20 is a plan view of a wrapping of another construction with an empty pouch.
Figure 20A:
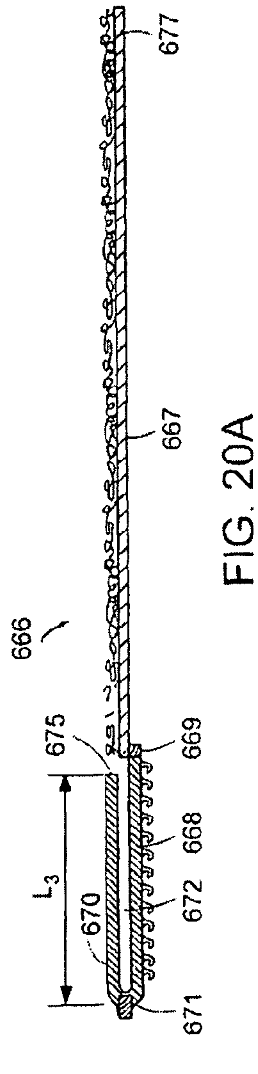
FIG. 20A is a cross section view of the wrapping of FIG. 20.
Figure 20B:
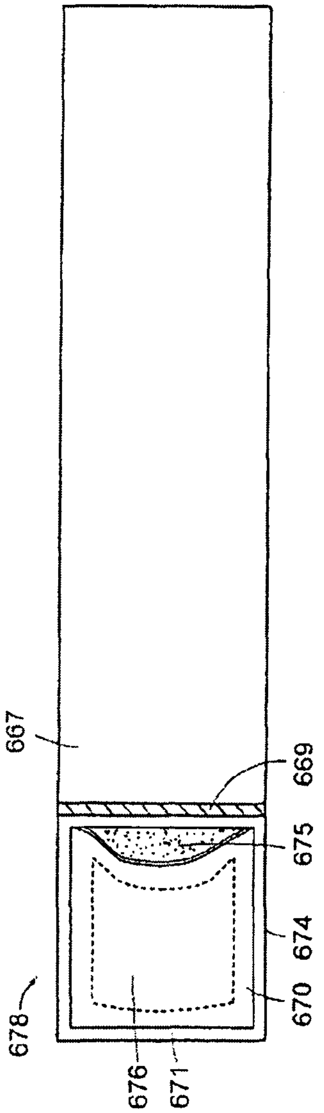
FIG. 20B is a plan view of the wrapping of FIG. 20 with a filled pouch.
Figure 20C:
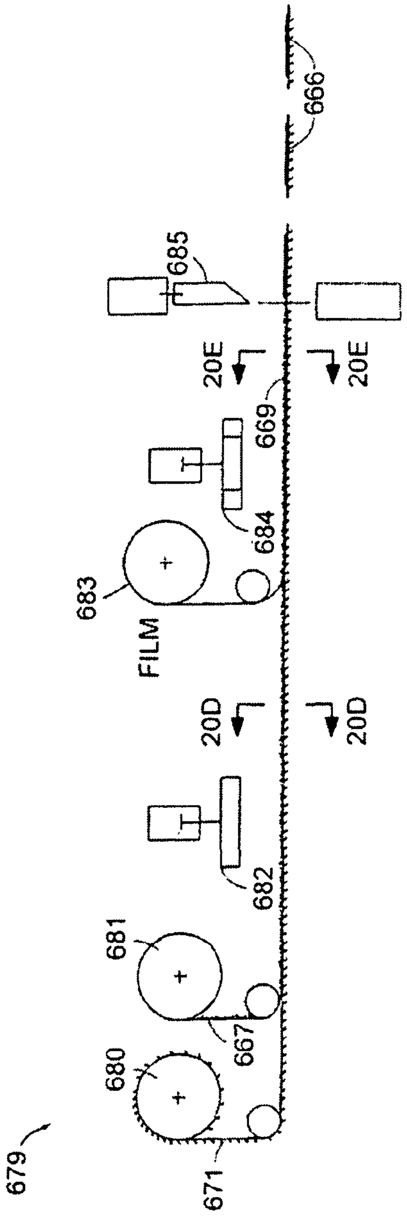
FIG. 20C is a side view of a system for making the wrapping of FIG. 20.
Figure 20D:
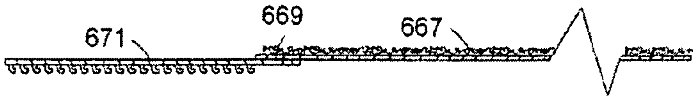
FIG. 20D is a cross section view of the continuous web in an intermediate step in the process performed by the system of FIG. 20C.
Figure 20E:
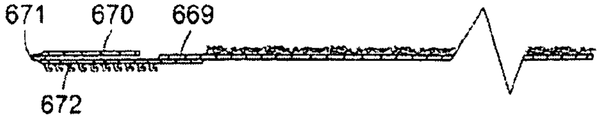
FIG. 20E is a cross section view of the continuous web in the last step of the process performed by the system of FIG. 20C before cutting off individual wrappings.

In FIGS. 20-20E a reusable, conformable wrapping 666 of length $L_1$ and width $W_1$ is formed from continuous, running length materials for securing a removable therapeutic pack against the body. A sheet of hook engageable non-woven loop fabric 667 of length $L_2$ is provided. The fabric 667 constitutes the major part (for example, greater than 3/4) of the overall length $L_1$ of the wrapping 666. A sheet of hook web 668 of length $L_3$, a minor part (for example, less than 1/4) of the overall length $L_1$ of the wrapping 666, is also provided. In the preferred embodiment, the non-woven loop material for sheet 667 is available commercially from Velcro, USA as Loop L 3310. The hook material for sheet 668 is available commercially from Velcro, USA as hook 29. The hook sheet 668 can be preformed using the process illustrated in FIGS. 3 and 3A.

This wrapping 666 of FIGS. 20-20B includes a running length of hook sheet 668, with the loop material 667 (loops facing up) at a region of overlap with a first machine direction weld 669, and then welding a single sheet of pre-formed biaxially-oriented film 670 at a second machine direction weld 671 at the outer edge of the hook material 668. A pouch 672 is then formed between the overlying film 670 and the back of the hook material 668 by applying welds at two sides, leaving one side open. In the case shown, side welds 673,674 are both made in cross machine direction leaving the pouch opening 675 at the interior of the wrapping 666.

A therapeutic pack 676 (FIG. 20B) may be placed in the pouch 672 through the opening 675. The wrapping 666 is wound around a body part with the soft loop side of 667 against the skin, holding the pouch 672 against the desired body part 8 and preventing its displacement. The loops 6 on the end region 677 of the wrapping 666 securely fasten to the hooks of 668 upon touch. Any excess length may be cut away.

In one case, the assembly 666 of hook and loop materials may be produced using in situ lamination procedure described with respect to FIG. 4, 4A or 4D, omitting any intervening calendered plastic layer and overlapping an extension of hook base layer over a margin or the loop material. In another case they my be united with discontinuous actions, now to be described. In this case the wrapping 666 is manufactured entirely by a bag machine (not shown) from the packaging industry. The bag machine brings the three sheets 667, 668 and 670 together and joins them using reciprocating heat seal jaws. Subsequently, the desired contents of the pouch 672 may be manually inserted to form wrapping 678 as illustrated in FIG. 20B.

FIGS. 20C, 20D and 20E show such an automated manufacturing process using a bag machine 679. From left to right, bag machine 679 includes a roll of continuous hook material 680, a roll of continuous loop material 681, and a reciprocating weld head 682 for weld 669. Following is a film roll 683 for the top layer of film 670 and a secondary weld head 684 for the weld 671. The weld 671 joins the film 670 to the end of the backside of the hook sheet 668. A cutoff jaw 685 slices individual wrappings 666 from the continuous web and separates welds 673 and 674 of two individual wrappings 666. The cut through the welds 673 and 674 of the continuous sheet allows weld 674 to stay on the trailing edge of one finished wrapping 666, and the weld 673 stays on the leading edge of another wrapping 666.

FIG. 20D shows the web after creation of the first weld 669. FIG. 20D shows the relationship between the hook strip 671 and the loop strip 667. FIG. 20E shows the web after the second weld head 684, illustrating the relationship of the hook and loop, and the addition of the film web 670 and the weld 669.

Plastic hook material, other than hook 29 from Velcro, USA, is suitable for this embodiment. Low cost knits or other non-wovens, other than Aspen® from Velcro, USA, can be used as well, as long as the knits are sufficiently strong to allow pulling without tearing. The plain loop material has to be somewhat stable so it can fasten to hooks properly. The hooks 4 for this embodiment are made from linear low density polyethylene and this ensures that the plastic weld 669, between the hook sheet 671 and the plastic binder or loop fabric 667, is sufficiently strong.

Typical biaxially-oriented films for preformed sheet 670 are polyethylene or polypropylene based, polyethylene being the least expensive and most economical. A preferred embodiment is a hook sheet 668 made of polyethylene resin, either a linear low standard injection mold grade or film grade.

For the preferred embodiment of the wrapping of FIGS. 20 and 20A, the pouch holds a thermal, therapeutic pack, and dimension $L_3$ is approximately 7.5 inches. Dimension $L_2$ is variable. Dimension $W_1$ is approximately 6 inches.

Figure 20F:
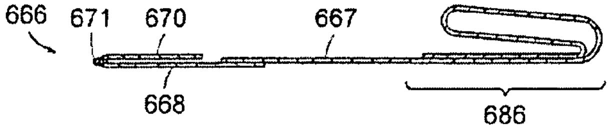
FIG. 20F is a cross section view of another form of the continuous web in the last step of the process performed by the system of FIG. 20C before cutting off individual wrappings.

In a preferred embodiment, the manufacturing process is on a bagging machine with a limited capacity to handle the joined sheets 666 widthwise. Folding the non-woven loop sheet 667 throughout the process enables the processing of a much longer wrapping on a machine that typically would not handle such a long item. A typical bagging machine 679 is commercially available from GN. Typical bagging machines are 54 inches in width, so wrappers longer than 40 inches require folding to process. In this case, FIG. 20F shows wrapping 666 as it finishes the manufacturing process of FIG. 20C with its loop section 667 folded (as part 686) so that the wrapping 666 can fit widthwise through the manufacturing process. This fold is accomplished during the process of FIG. 20C by continuously folding sheet 667 as it is unrolled from supply roll 681.

Figure 21:
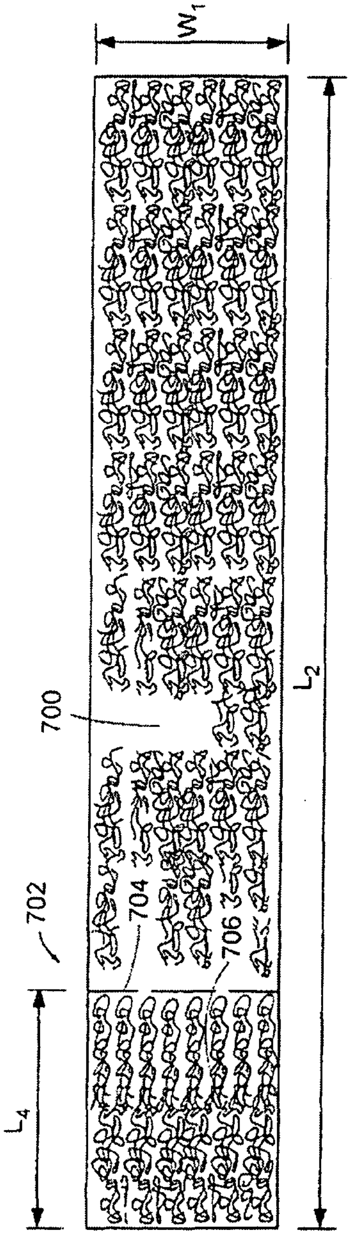
FIG. 21 is a plan view of non-woven loop material to be folded to form a wrapping.
Figure 21A:
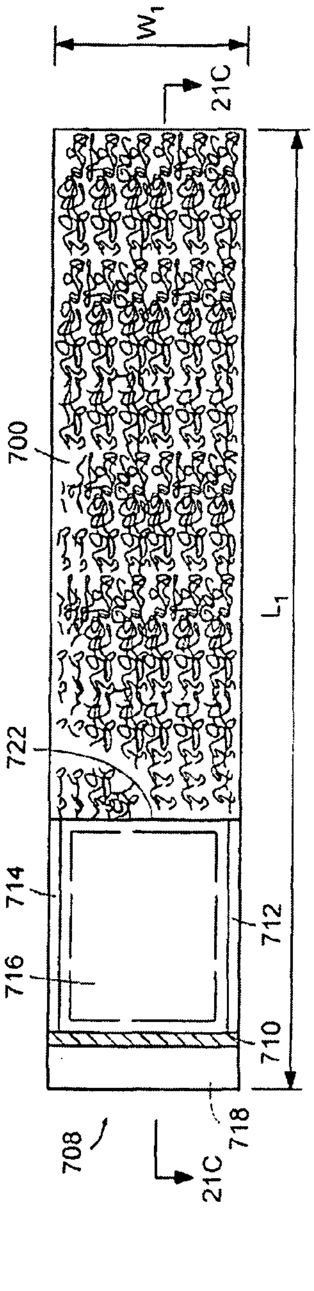
FIG. 21A is a plan view of a wrapping constructed from the material of FIG. 21.
Figure 21B:
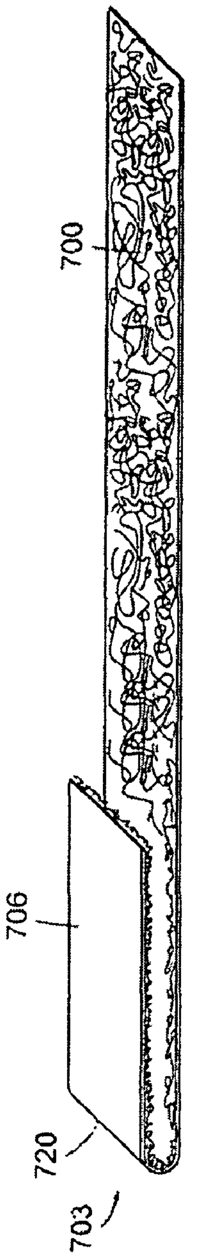
FIG. 21B is a view of the material of FIG. 21 folded to form a wrapping with a pouch.
Figure 21C:
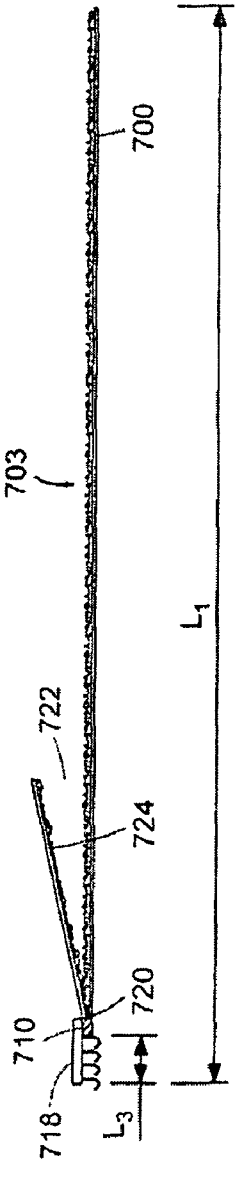
FIG. 21C is a cross section view of the wrapping of FIG. 21A.

In another embodiment 708, illustrated in FIGS. 21A and 21C, the main body of the wrapping as well as the entire pouch are formed of preformed loop material, and the hook material is joined in the region in which the loop material is folded back upon itself. Again, two welds, both transverse to the machine direction, form the sides of the pouch and the pouch opening is inside the wrapping. The embodiment 708 is a conformable wrapping of length $L_1$ and width $W_1$.

The embodiment 708 of FIGS. 21A and 21C is a conformable wrapping of length $L_1$ and width $W_1$ for securing a removable therapeutic pack 716 against a body part 8. A sheet 702 of hook-engageable non-woven loop fabric of length $L_2$, greater than $L_1$, is provided. The sheet 702 is folded along an axis 704 transverse to its length and this fold 720 forms sections 700 and 706 as illustrated in FIGS. 21 and 21B. This fold 720 is done in such a manner that the folded sheet 703 has hook-engageable loop sides of 700 and 706 facing one another as illustrated in FIG. 21B. A sheet 718 of hook web having length $L_4$, a minor part (for example, less than ¼) of the overall length $L_1$ of the wrapping 708, is also provided. This hook sheet 718 can be manufactured using the process illustrated in FIGS. 3 and 3A. The hook sheet 718 is joined to the end of the sheet 703 at weld 710 with hooks 4 facing the opposite direction of loops 6 of section 706 as illustrated in FIG. 21C. Welds 712 and 714 seal loop section 706 to loop section 700 forming a pouch 724 with an opening 722. The opening 722 is oriented such that whenever contents are put into the pouch 724, the contents cannot fall out because the opening 722 is against the body 8 on which the strap is wrapped. A therapeutic pack 716 may be inserted into pouch 724 through opening 722 to form embodiment 708.

A preferred embodiment uses polyethylene resin for the hook material 718 but other resins, which are compatible with the non-woven loop material to make the pocket and the wrap, could also be used. The benefits or features of this wrap are that the wrapping 708 mainly consists of porous non-woven loop material so that the wrapping 708 can bend or ventilate and not create a clammy or sweaty condition against the skin. The hook portion 718 is oriented such that when the weld 710 is created, the hooks 4 melt to form a good attachment without need for film on the back of the non-woven loop strap 706.

Figures 21D, 21E, 21F:
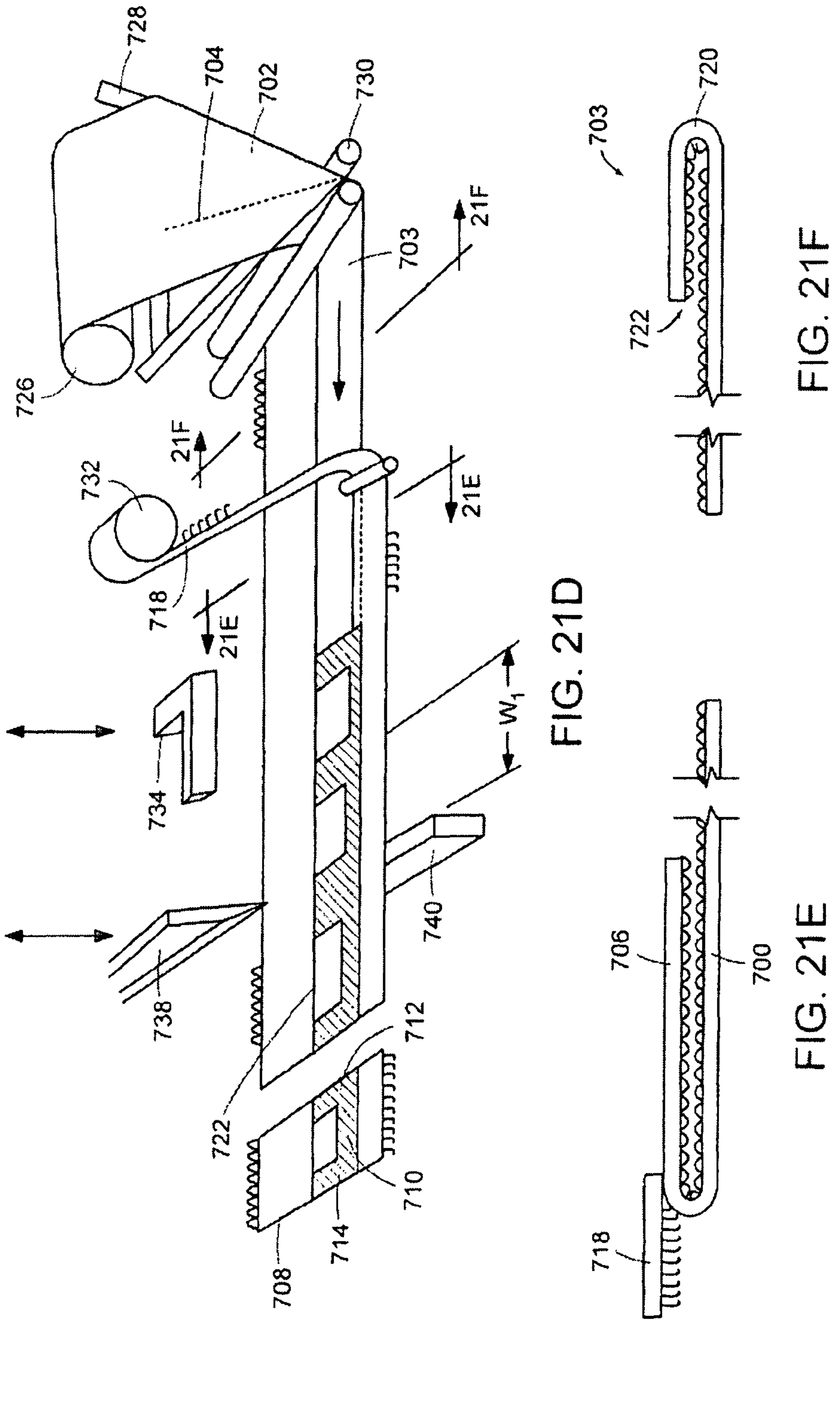
FIG. 21D is a diagrammatic, perspective view of a flat bagging system for making the wrapping of FIG. 21A.
FIG. 21E is a cross section view of the continuous web in the process performed by the system of FIG. 21D before welds are formed.
FIG. 21F is a cross section view of the continuous folded material of FIG. 21 in the process performed by the system of FIG. 21D.

FIGS. 21D, 21E and 21F illustrate the automated manufacturing process to make the wrapping 708 illustrated in FIG. 21A. Moving from right to left, a roll 726 of non-woven loop material 702 is positioned on an unwind and positioned such that a jay-fold is managed at fold line 704. A folding bar or board 728 is provided. Rollers 730 pinch the fold 720 just after the fold plate or folding board 728 creates the J-fold 720. Moving left, sheet 702 enters into a flat bag sealing machine to form the rest of the wrapping 708. Typical flat bag-sealing machines are available from GN or RO-AN. The GN style bag sealing machine is illustrated where the web is intermittently positioned into a tooling station. Roll 732 provides the hook web 718 that is laid on top of the fold line 704, and then positioned under weld station 734.

Weld station 734 produces an "L" seal that ultimately results in welds 710, 712, and 714. At each index, weld station 734 positions an "L" weld shape, resulting in a welds 710 and 736 as illustrated in FIG. 21D. Welds 710 and 736 form an "L" configuration, where the bottom of the "L" is single width and is represented by weld 710, and the vertical or up and down portion of the "L" is double width and is represented by weld 736. The cutoff jaw 738 bisects the double width of weld 736 so that the welds become standard width all the way around the pouch 724. Moving towards the left, upper shear 738 cuts the web against lower shear 740.

In the process illustrated in FIG. 21D, the web is intermittently advanced, so that at each advance, there is a period within the process where all of the devices such as 734 and 738 act on the web. The repeat length $W_1$ defines the width $W_1$ of the strap, not the length $L_1$, and it is determined by the stroke of the film advance. Tooling for 734 is designed based on the width $W_1$ of the strap. As in FIG. 20F, if the sheet 702 is so long that it will not fit widthwise in the bagging machine, then the sheet 702 could be folded back on itself to allow it to go through.

For both embodiments of FIGS. 20F and 21A, if an extra long strap is required, the cutoff shear mechanism can cut through the folded loop material and then it can be unfolded afterwards. In some of the next embodiments, a cutoff shear mechanism uses a hot wire. In this case, none of the components can be folded because the resulting end seal prevents unfolding the wrapping.

Figure 22:
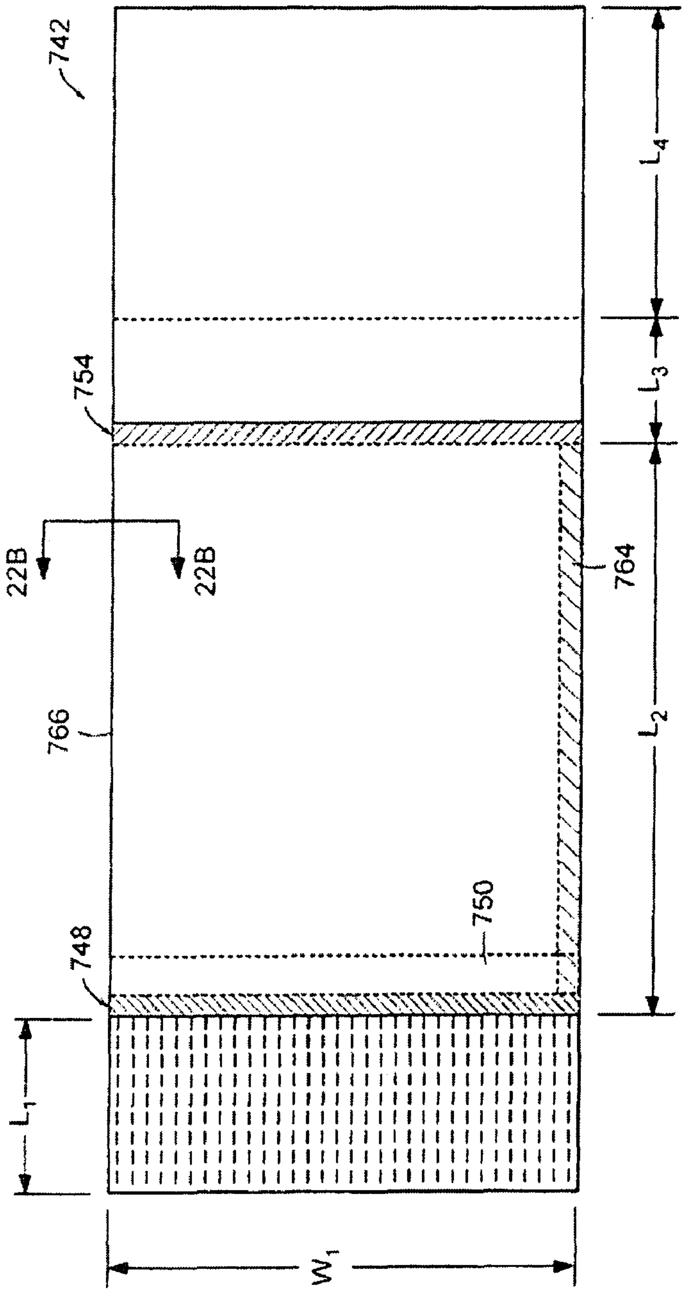
FIG. 22 is a plan view of a wrapping of another construction.
Figure 22B:
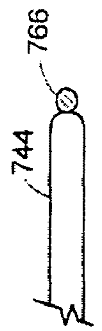
FIG. 22B is a cross section view of an edge weld in the wrapping shown in FIG. 22.
Figure 22A:
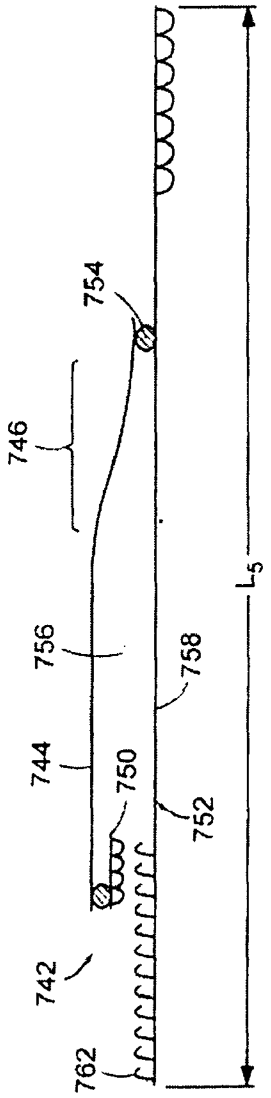
FIG. 22A is a cross section view of the wrapping shown in FIG. 22.

Another embodiment is illustrated in FIGS. 22 and 22A. This embodiment 742 is different from the previous wrappings constructed using bag making machines because the pouch is not breathable, it is waterproof, and the pouch contents may be wet and will not seep out of the wrapping. The pouch opening is re-sealable with hook and loop touch fastener strips. The wrapping keeps everything external to the wrapping dry. The wrapping embodiment will also keep the treatment area drip-proof or somewhat dry as well. This wrapping has an overall length of $L_5$ and a width of $W_1$. For the thermal pack version of this embodiment, the preferred dimensions are $L_1$ of 1.5 inches, $W_1$ is 8 inches, $L_2$ is 6 inches, $L_3$ is variable, $L_4$ is 6 inches, and $L_5$ is up to 25 inches. The total length $L_5$ depends on the intended application of the wrapping. If the wrapping is intended to wrap around an ankle, $L_5$ is about 17.5 inches. If the wrapping is intended to wrap around a knee, $L_5$ is about 25 inches. If the wrapping is intended to wrap around a wrist, then $L_5$ is about 13.5 inches.

As illustrated in FIG. 22A, top portion 746 is a preformed assembly consisting of a composite loop material strip 750 and a preformed biaxially-oriented film sheet 744 welded together at weld 748. The composite loop strip 750 with plastic backing is produced via the process illustrated in FIGS. 2 and 2A. The preformed sheet 752 with loop section 760, hook section 762, and plain plastic section 758 spanning the loop section 760 and the hook section 762 is produced via the process illustrated in FIGS. 3 and 3A. The preformed biaxially-oriented film sheet 744 is joined to section 758 at weld 754 forming pouch 756. Thus, weld 754 joins top portion 746 to bottom portion 752. Hook section 762 is used to seal the pouch 756 shut and also fastens the wrapping in place. The length of sheet 752 is limited only by the calender tool roll length.

Welds 766 and 764, formed at cutoff of each individual wrapping from the web, are edge welds that seal the remaining edges of the pouch. In this embodiment, the process utilized to make this wrapping is a standard flat bagging machine where the cutoff is formed by a radiant heat sensitive knife. A radiant heat sensitive knife is extremely hot, at 600 to 700 degrees Fahrenheit. Radiant energy is absorbed by the edges and a bead 766 or 764 is formed.

Figure 22C:
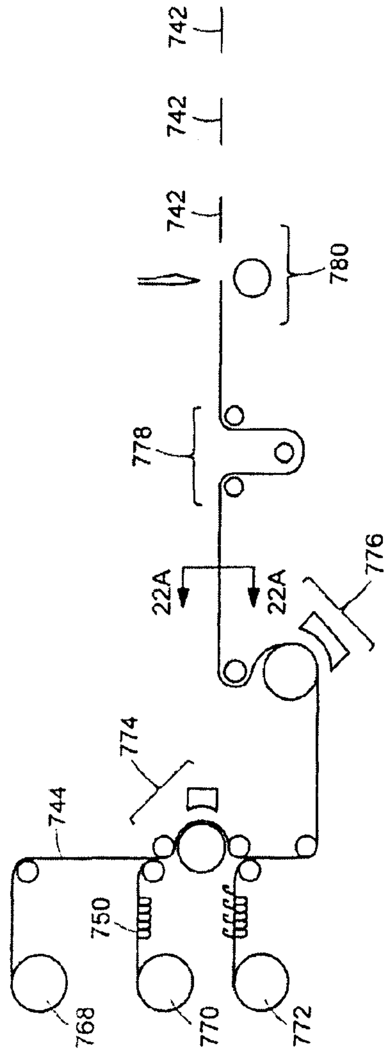
FIG. 22C is a side view of a flat bagging system for making the wrapping shown in FIG. 22.

The process for making the wrapping embodiment of FIGS. 22 and 22A is illustrated in FIG. 22C. For this process, three supply rolls are provided: a roll of preformed biaxially-oriented film 768, roll of loop material 770, and a roll of preformed composite sheet 772 with hooks and loops. In the preferred embodiment, supply roll 768 holds the biaxially-oriented film 744 that is polyethylene based, approximately 0.002 to 0.004 inch thick Supply roll 770 holds a web of non-woven or woven material 750 with loops. In the preferred embodiment, this web has a polyethylene backing produced by the process of FIGS. 2 and 2A. Supply roll 772 holds the preformed composite 752 with hooks and loops.

Figure 22D:
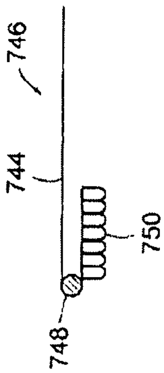
FIG. 22D is a cross section view of the continuous web in an intermediate step in the process shown in FIG. 22C.

The first step in the process of FIG. 22C is performed by weld station 774 which joins biaxially-oriented plastic sheet 744 with non-woven laminated sheet 750 at weld 748. The assembly 746 consisting of the two joined sheets with weld 748 is illustrated in FIG. 22D.

The next step in the process consists of weld station 776 producing weld 754 that joins the assembly 746 to the composite sheet 752. The typical seal equipment that is used in weld stations 774 and 776 are commercially available drag sealers. These drag sealers are continuous motion sealers, as opposed to clamp-type sealers. The film runs continuously through these drag sealers.

This entire process can be performed on a standard bag sealing machine. This machine includes a dancing mechanism 776 which changes a web from continuous to intermittent motion. This is required because cutting station 780 is a radiant end seal assembly that intermittently produces welds 764 and 766 as well as cuts individual wraps 742 free from the continuous web.

Figure 23:
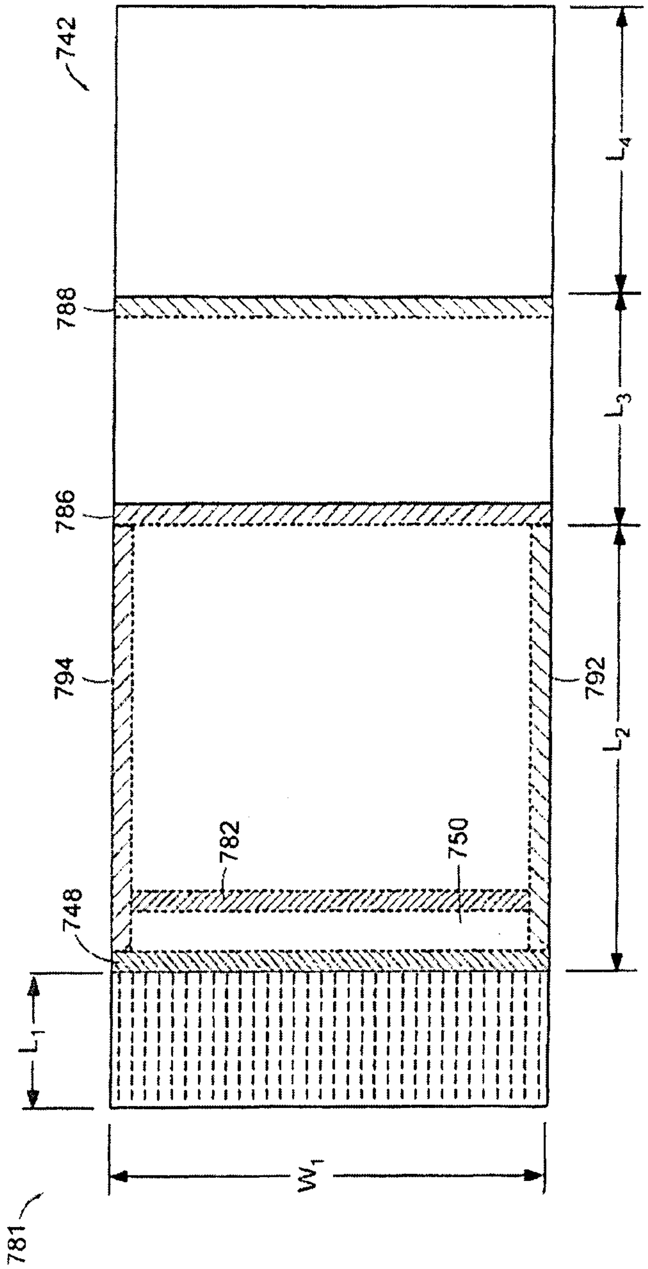
FIG. 23 is a plan view of a wrapping of another construction.
Figure 23A:
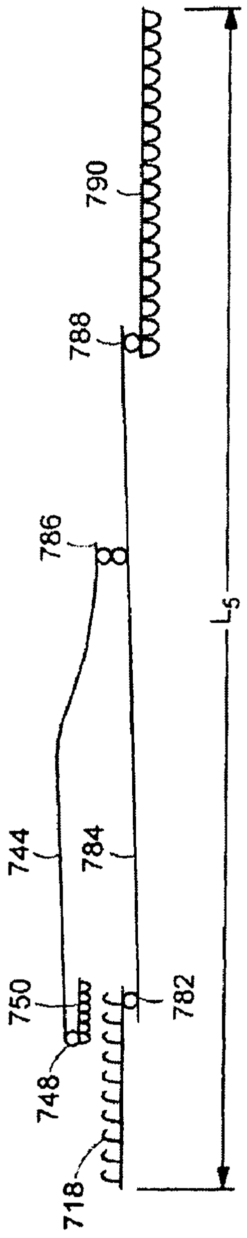
FIG. 23A is a cross section view of the wrapping shown in FIG. 23.

FIGS. 23 and 23A illustrate another wrapping embodiment that is similar to the wrapping of FIGS. 22 and 22A. One advantage of the current embodiment is that it uses more preformed biaxially-oriented plastic film and less calender rolled film, which is more cost effective because film made by the calender roll process, illustrated in FIGS. 4 and 4A, is more expensive than biaxially-oriented plastic film. Another advantage is that the length of the wrapping is only limited to the width of a flat bag sealing process, unlike the wrapping of FIGS. 22 and 22A which is limited by the length of the rollers of a calender roll process.

This embodiment has a sub assembly consisting of calender roll formed non-woven loop strip 750 with plastic backing that is joined to biaxially-oriented film strip 744 at weld 748. This sub assembly is joined to film sheet 784 at weld 786. Film sheet 784 is a preformed biaxially-oriented plastic film sheet that is introduced into the bag sealing machine and is joined to preformed hook strip 718 at weld 782. Furthermore, calender roll formed non-woven loop strip 790 with plastic backing is joined to preformed biaxially-oriented plastic film 784 at weld 786. Biaxially-oriented plastic film sheets 784 and 744 can be cast or they can be blown. Both 784 and 744 are commercially available and can be different types of resins based on the requirements of the end wrap, as well as the hook materials and loop materials.

In this design, as in the previous embodiment, hook strip 718 has a dual role. The right side of hook strip 718 serves as the hooks to close the pouch by means of the loops of non-woven loop strip 750 and also serves as a means of attaching or securing the wrapping in place. Typical dimensions for the preferred embodiment are as follows: for wrapping about ankles, $L_5$ is about 17.5 inches, about the knees $L_5$ is about 25 inches, and about a wrist $L_5$ is about 13.5 inches. These dimensions are based on cold pack therapy. The bulge of the cold pack may add an uncertain amount to the requirement of the overall dimension due to the uncertain width and height of the cold pack. Using the wrapping for heat therapy for instance, might result in significantly different dimensions. For the preferred cold pack embodiment, the width $W_1$ of the wrapping is eight inches to secure the cold pack.

Figure 23B:
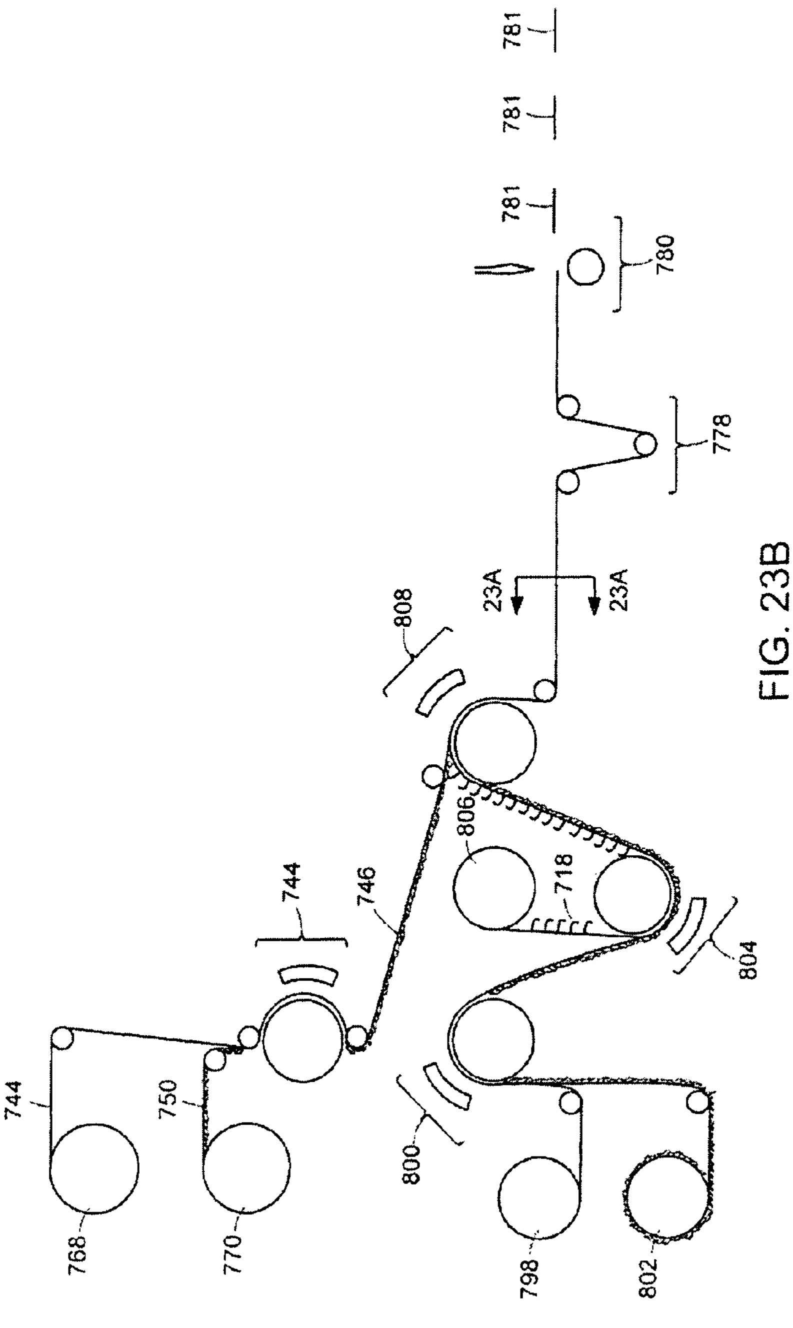
FIG. 23B is a cross section view of a flat bagging system for making the wrapping shown in FIG. 23.

The process for manufacturing the embodiment of FIG. 23 is illustrated in FIG. 23B. The first supply roll 768 provides biaxially-oriented film 744, the second supply roll 770 provides non-woven loop material 750 with plastic backing, the third supply roll 798 provides biaxially-oriented plastic film 784, and the fourth supply roll 802 provides non-woven loop material 790 with plastic backing. Welding station 744 forms weld 748, which joins the loop strip 750 to the biaxially-oriented plastic film sheet 744. Welding station 800 creates weld 788 that joins the biaxially-oriented plastic film 784 to the non-woven loop strip 790. Welding station 804 forms weld 782 which joins the hook strip 718 to the biaxially-oriented plastic film sheet 784. Welding station 808 creates a third weld 786 which joins the face 744 of the pouch to the backside 784 of the pouch. The welding stations 744, 800, 804 and 806 are drag type welders where the film is continuously moving under the weld head. FIG. 23A shows the resulting composite assembly after these welding steps.

The next step in the process to manufacture the wrapping of FIG. 23 is a dancing mechanism 778, which was described in the previous description of the process on a bag sealing machine as a mechanism that allows the film to stop momentarily while individual wrappings 781 are separated and cut off by the hot knife 780. Hot knife 778 also creates edge seals 792 and 794 that close off the sides of the pouch. Welds 792 and 794 are bead type welds, similar to the edge seals created by the process of FIG. 22C.

Another wrapping embodiment is similar to the wrapping of FIG. 23 because preformed biaxially-oriented plastic sheet is also used to form the pouch. This wrapping is illustrated in FIGS. 24, 24A, 24B and 24C. As in the previous embodiment's description, using plastic sheet to form the pouch results in a waterproof pouch. However, in the current embodiment, the pouch is formed by folding a preformed biaxially-oriented plastic sheet 811 rather than joining two separate flat sheets. An additional feature is a stretch component 810 on the hook end which enables the wrapping to be tightly fastened. This stretch component 811 increases the flexibility of the wrapping and allows for some expansion so it is not so constricting.

The pouch of this wrapping is formed by a folded sheet 302 of preformed biaxially-oriented film. Folded film 811 may be introduced into the manufacturing process in two ways. The film 811 is jay-folded and is joined to stretchy sheet 810 at weld 813 directly on the fold line. Hook strip 810 is joined to a stretchy material 810 using the off-line calender roll process of FIGS. 4 and 4A to form assembly 815. Hook sheet assembly 810 is joined to a preformed biaxially-oriented plastic sheet 811 at weld 813.

Non-woven loop sheet 814 is joined to folded film 811 at weld 812. Non-woven loop sheet 814 either has a polyethylene backing from the calender roll process of FIGS. 2 and 2A, that is done prior to this assembly, or it can be non-woven loop material without polyethylene backing, depending on the required quality of the weld and the other requirements of the application. The amount of hook and loop material in both of these cases can be adjusted according to cost concerns.

As a variant to this embodiment, the opening of the pouch can be made sealable by adding a pressure-sensitive assembly 816 to the film 811 prior to folding the film 811. The pressure sensitive assembly 816 consists of a pressure-sensitive adhesive strip 817 with a release tab of 818 and that allows the pouch to be sealed after the cold pack or other therapeutic pack is manually inserted into the pouch. After release tab 818 is pulled off, pressure sensitive strip 817 sticks to the other side of folded film 811 and seals the pouch opening shut.

This embodiment may also be varied by replacing the film 811 with a woven or non-woven knit. This replacement material may be waterproof and is commercially available as Tyvek®, Typar®, or scrim.

Figures 24, 24A, 24B:
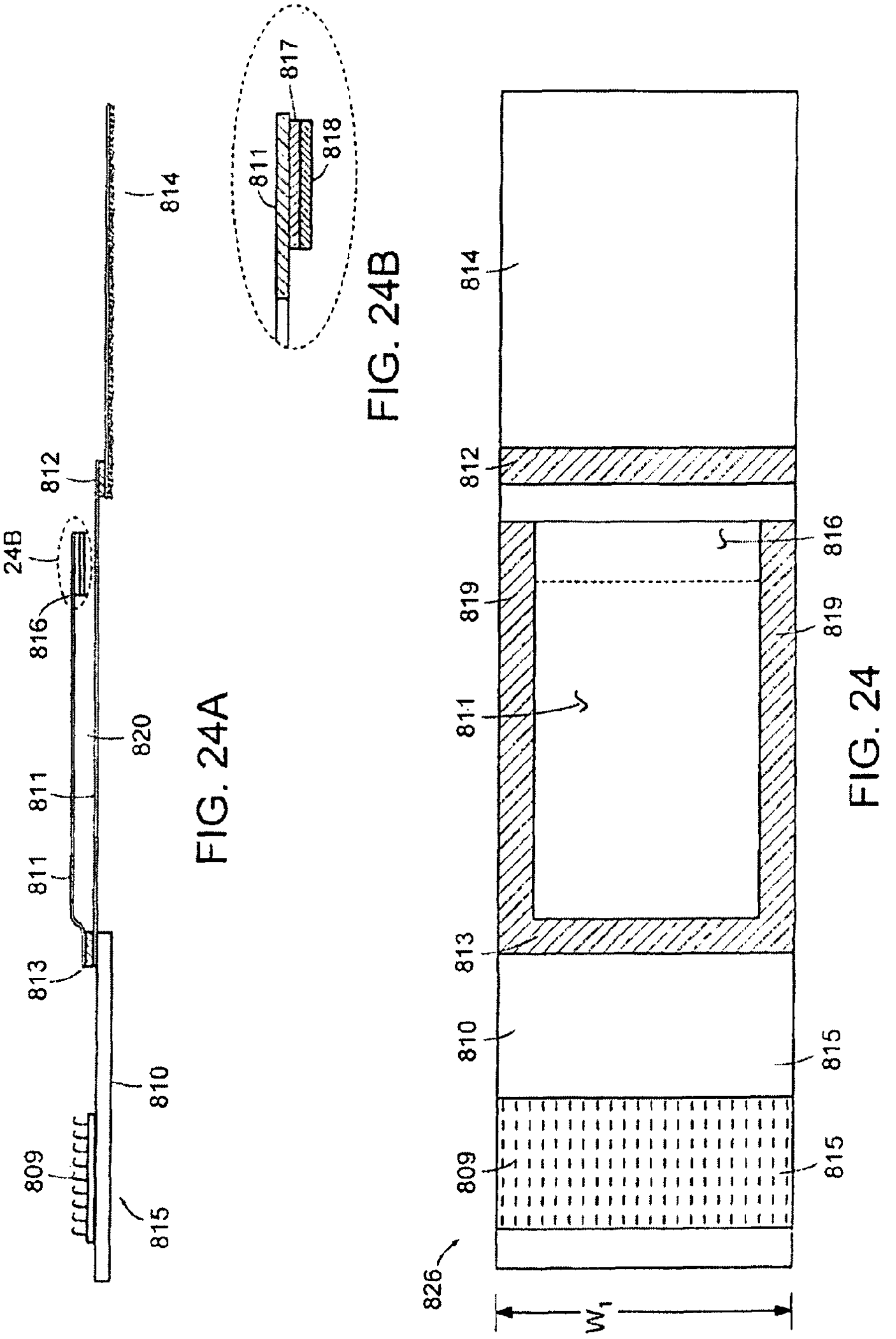
FIG. 24 is a plan view of a wrapping of another construction.
FIG. 24A is a cross section view of the wrapping shown in FIG. 24.
FIG. 24B is a magnification of a sealing assembly at the edge of the pouch flap of the wrapping shown in FIG. 24.
Figure 24C:
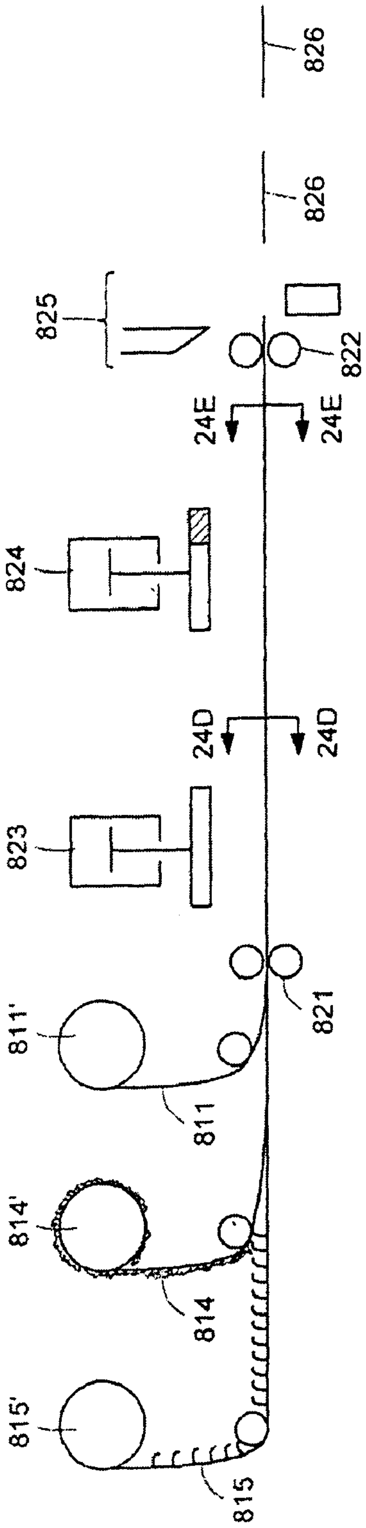
FIG. 24C is a side view of the flat bagging system for making the wrapping shown in FIG. 24.
Figure 24D:
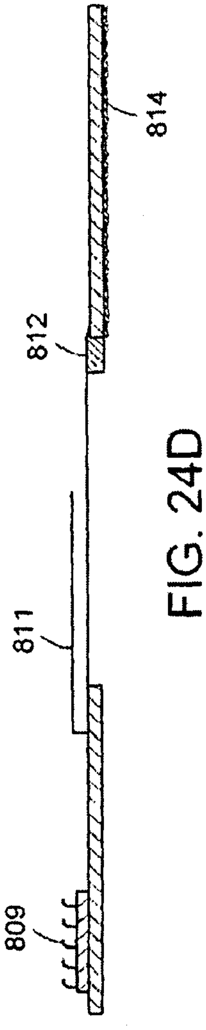
FIG. 24D is a cross section view of the continuous web in an intermediate step in the process shown in FIG. 24C.
Figure 24E:
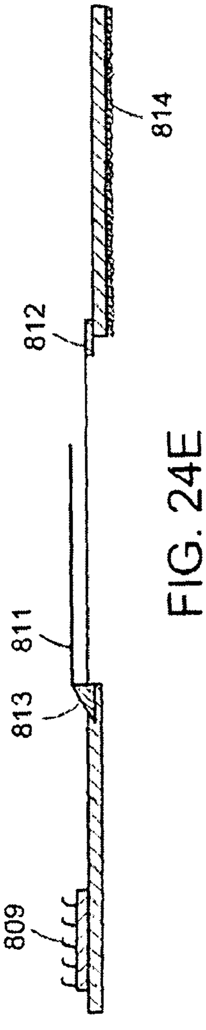
FIG. 24E is a cross section view of the continuous web in the step before cutoff in the process shown in FIG. 24C.

The process of manufacturing this embodiment is illustrated in FIGS. 24C, 24D and 24E. For this process, supply rolls 815', 814' and 811' with material for features 815, 814 and 811, respectively are provided. Preformed biaxially-oriented plastic film 811 may be jay-folded and rolled up in the supply roll or two sheets of biaxially-oriented plastic film could be double wound in the supply roll. A set of nip rolls 821 work in conjunction with 822 as a servo drive mechanism. The process indexes intermittently and repeats with a repeat length that is the width of the wrapping $W_1$. Weld station 823 makes weld 812 that joins the pouch material 811 and the loop material 814. Weld station 824 uses a "L" shaped welder to make the welds 813 at the fold line of pouch material 811 that joins the pouch 820 to the hook and stretchy material subassembly 815. Weld station 824 also creates a double-width edge weld that is transverse to machine direction. Finish servo rollers 822 are located just before the cutoff section 825. The cutoff section 825 is a cold knife and cuts the double-width edge weld in half. This cutoff 825 cuts and bisects the double-width edge weld down the middle to create welds 819 on two wrappings 826. This produces a finished wrapping 826 with three sealed pouch edges.

Another wrapping embodiment is illustrated in FIGS. 25, 25A, 25B and 25C. This wrapping is similar to the embodiment of FIG. 17 because this wrapping has hook and loops symmetrically placed on both sides. This wrapping is similar to the embodiment of FIG. 21 because this wrapping is mostly formed of non-woven loop material. This wrapping consists of two sheets of non-woven loop material 832 that are laid down on top of one another and welded to form a pouch 828. The sheets both have strips of hooks 827 on one end. The advantages to this design are that the non-woven material 832 is more durable and comfortable against the skin than biaxially-oriented film. Furthermore, the non-woven loop material has the appearance of being cloth-like and is comfortable, permeable and breathable. Since there are loops and hooks on both sides, the wrapping may be wrapped two different ways, making the wrapping easy to use.

Loop section 833 is an end section of the wrapping that is die cut to make it easier to peel the hooks 827 from the loops 832. Hook strips 827 are welded onto non-woven loop material 832. The body of the wrapping has loops 832 on both sides. Welds 829 close off the pouch 828. There is also the option of creating multiple pouches in the wrapping by putting more welds 831 along the length of the wrapping. The pouch 828 is welded completely around its periphery except for the top of the wrapping as an entry point to the pouch. As an option, a window 830 could be die-cut into one side, allowing any contents that are in the pouch 828 to be in intimate contact with the skin or surface to which it is wrapped. The pouch contents could be any kind of medication or anything else that is desired to have contact to the surface of the skin.

Figure 25A:
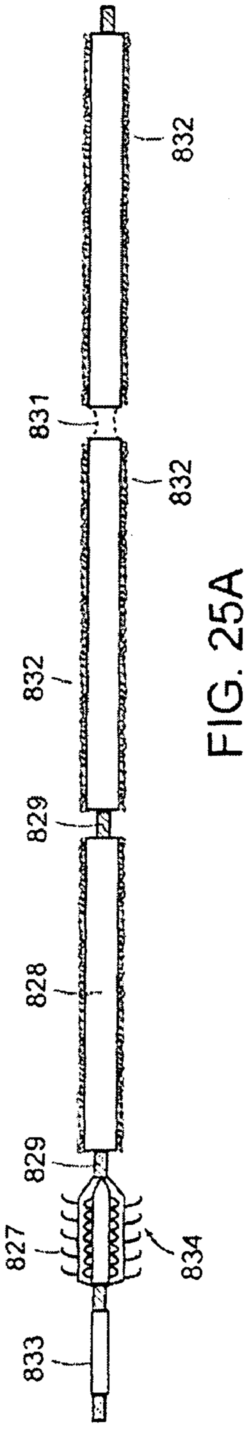
FIG. 25A is a side view of the wrapping of FIG. 25.
Figure 25:
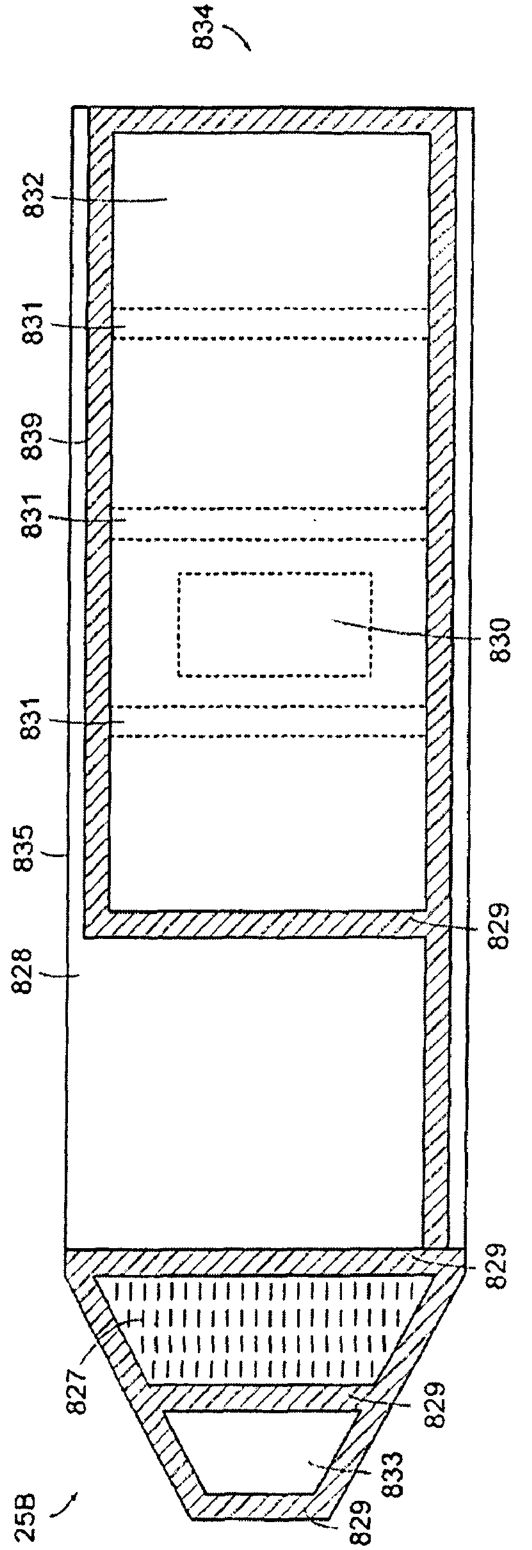
FIG. 25 is a plan view of a wrapping of another construction shown as part of a continuous web.
Figure 25B:
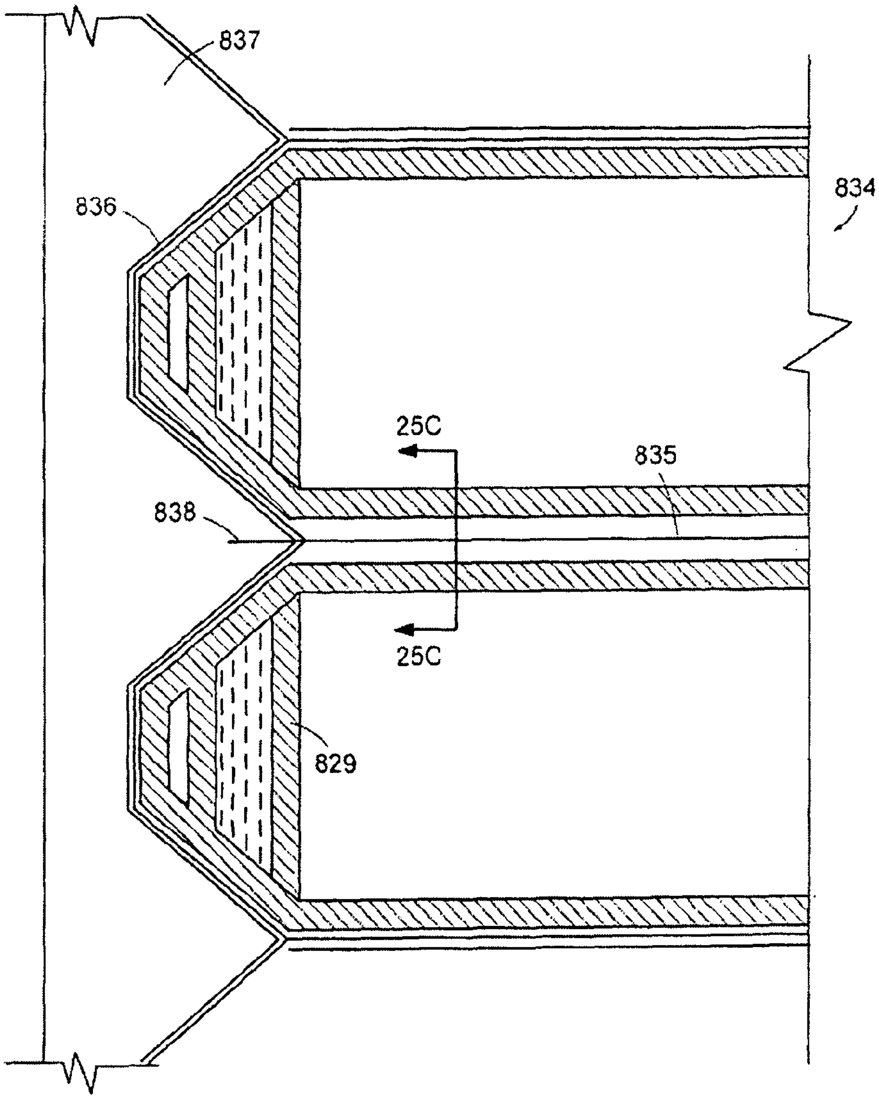
FIG. 25B is a magnification of the end of the continuous web shown in FIG. 25.
Figure 25C:
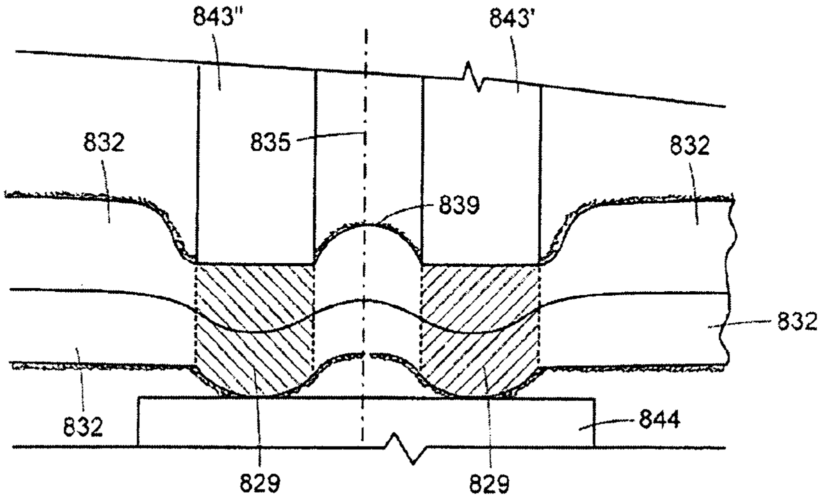
FIG. 25C is a magnified cross section view of the welds being formed to make the wrapping shown in FIG. 25.
Figure 25D:
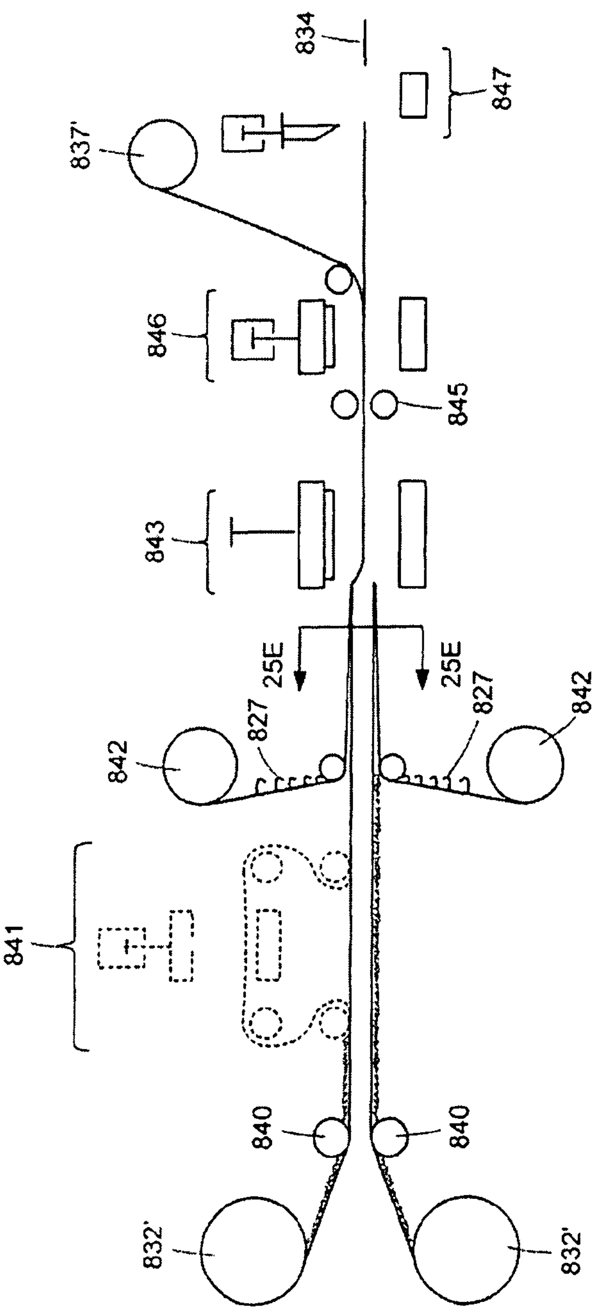
FIG. 25D is a side view of the flat bagging system for making the wrapping shown in FIG. 25.
Figure 25E:
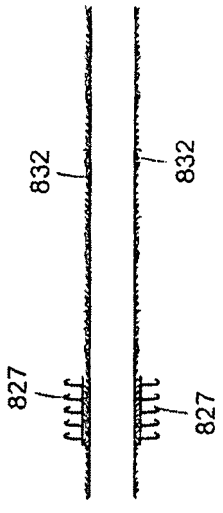
FIG. 25E is a cross section view of the continuous web before welding in the process shown in FIG. 25D.

The continuous process for manufacturing this wrapping embodiment is illustrated in FIG. 25D. First, two supply rolls unroll out non-woven loop material 832 into servo drives 840. As an option, a die cutting station 841 can cut an access window 830 into one sheet 832. Since die cutting station 841 is a discrete operation, a shuttle device is provided to hold a targeted portion of sheet in a fixed position despite a continuous input and output flow of sheet material. After optional station 841, two supply rolls 842 unroll out hook sheets 827. One hook sheet 827 is positioned on top of each of the two loop sheets 832.

Welding station 843 creates welds 829 and optionally 831 to seal the sheets 832 and 827 together and form the pouch 828. These welds 829 and 831 extend transversely and longitudinally to machine direction.

FIG. 25C shows a space between the individual transverse welds which produces a free edge 839 of the loop after individual wrappings are cut from the web along line 835. This results in a flexible, lofty soft, non-woven edge 839 for the wrapping. Weld station 843 uses weld head 843' and weld head 843". Separated between these two weld heads is a space which results in unwelded material 839. The knife section 847 cuts at line 835 and the free edge 839 is formed beside the cut.

Die cutter 846 continuously cuts the end tab out following line 836. This cut removes material 837 as illustrated in FIG. 25B and this material is rolled up in excess roll 837'. At the end, cutting station 846 performs a cold sheer cut along line 835 and separates the individual wrappings 834 from the continuous web. FIG. 25B shows the trim 837 and a cutting line 836. The cutting line 835 is slightly thinner than cutting line 836 because knife station 847 is thinner. Cut 836 is generated or cut by die-cutting station 846. By extending the width of the knife's blade 846, cutting is guaranteed if the web moves slightly left or right. The width of cut 836 allows the knife edge to cleanly cut the web or the part free. Cutting line 835 is also extended into the excess material 837 and this extension is 838. These extensions allow the part to be cut free from the web even if the web moves just subtly left or right, or repeated move or a little bit of tolerance with repeat advance. These extensions guarantee a wrapping part 834 which is free from the trim web.

Figure 26A:
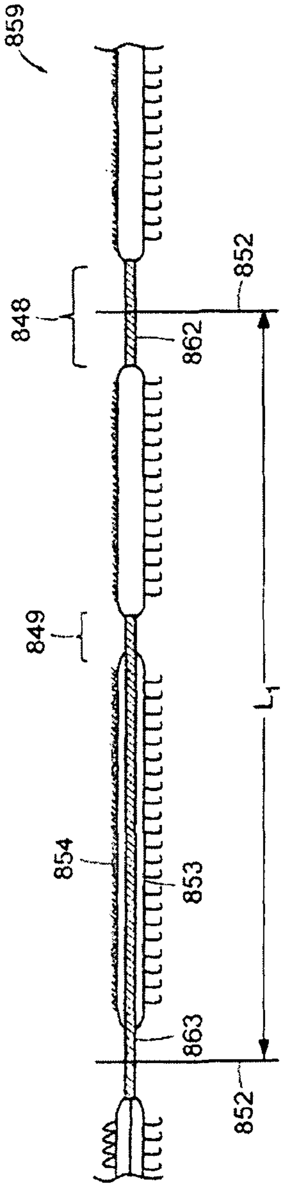
FIG. 26A is a side view of the continuous web shown in FIG. 26.
Figure 26:
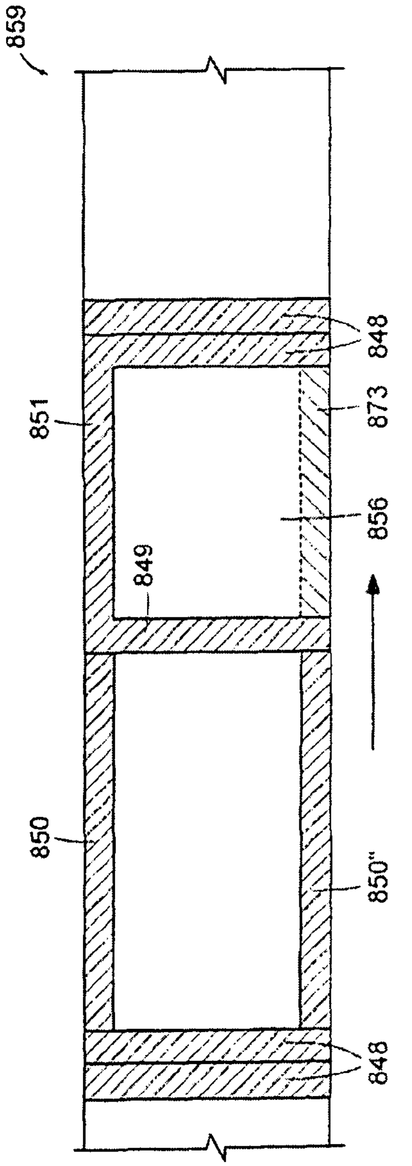
FIG. 26 is a plan view of the continuous web that forms wrappings of another construction.

FIG. 26 shows a wrapping embodiment 859 with length $L_1$ that is similar to the wrapping of FIGS. 7-12. However, the current embodiment is made from two sheets: a hook web 853, and a loop web 854 whereas the embodiment of FIGS. 7-12 is made from one folded sheet. Beyond that, FIGS. 26B (flat bagging sealing process) and 26E (pouching process) show similar processing that have been already described.

Figure 26B:
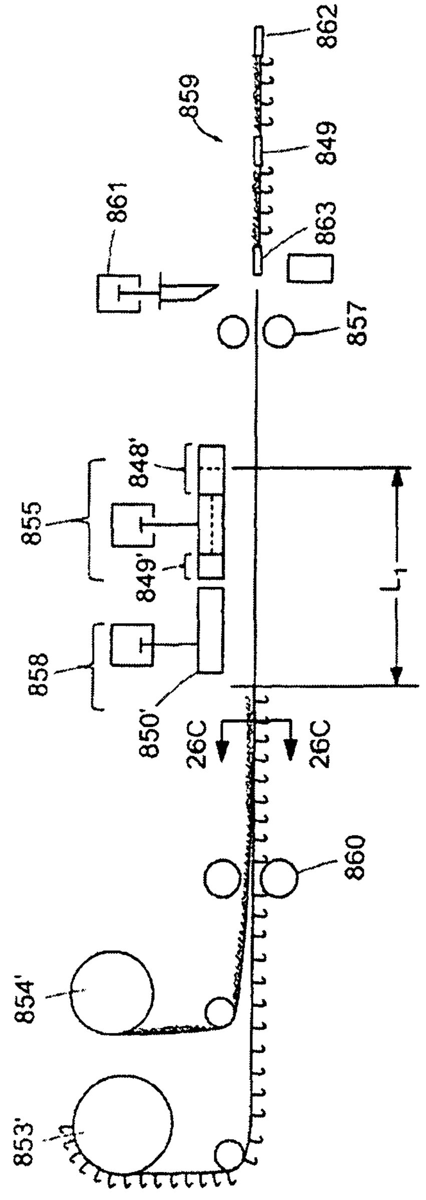
FIG. 26B is a side view of a flat bagging system for making the wrapping shown in FIG. 26.
Figure 26C:
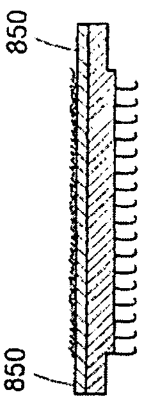
FIG. 26C is a cross section view of the continuous web before welding in the process shown in FIG. 26B.
Figure 26D:
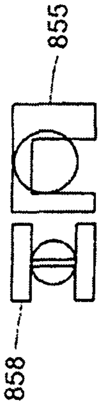
FIG. 26D is a plan view of the weld heads used in the process shown in FIG. 26B.

The flat bag sealing process of FIG. 26B shows an intermittent motion machine using servos 860 and 857 with a repeat distance of $L_1$. The flat bag sealing process utilizes two weld stations 858 and 855 to seal the sheets along the length of the wrapping. Weld station 858 creates welds 850. Weld station 855 has a unique shape, illustrated in FIG. 26D, to create double width transverse weld 848 and machine direction weld 851 that leave a opening, along machine direction, in the wrapping for pouch 856. Cold cutoff knife 861 cuts off individual wrappings 859 transversely to machine direction by bisecting transverse weld 848. Bisected weld 848 becomes weld 862 that forms the end of one wrapping 859 and weld 863 that forms the beginning of another wrapping 859. The pouch 856 is formed between welds 862 and 849.

Figure 26E:
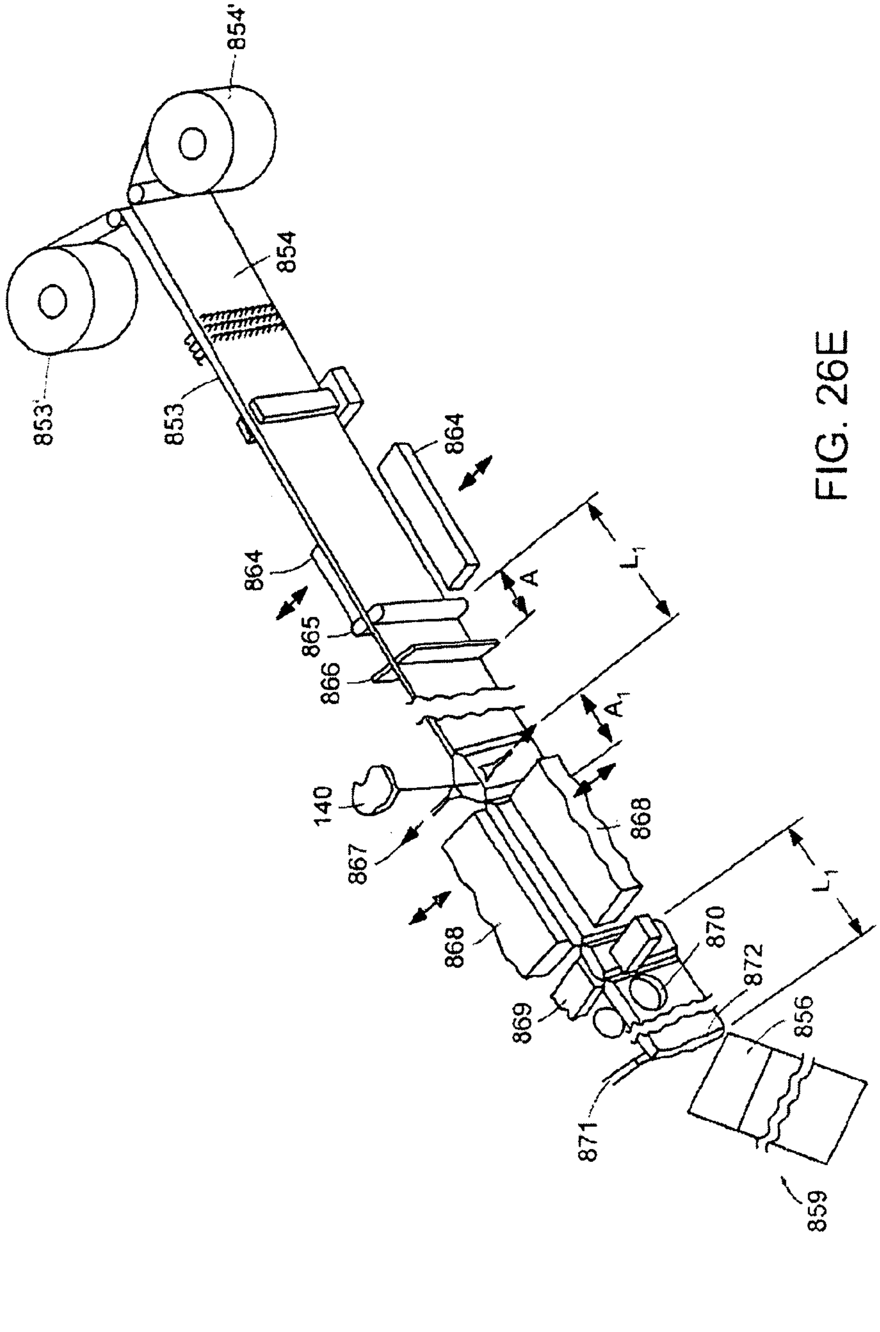
FIG. 26E is a perspective view of a pouching system alternately used to make the wrapping shown in FIG. 26.

FIG. 26E shows another process for making wrapping 859. The pouching process consists of the two webs 853 and 854 going through a servo mechanism into a bottom sealer 864 and then the rest is similar to the pouching process of FIGS. 7-12. In this pouching process, contents 140 are placed in the pouch 856 and the pouch is sealed using weld 873. One advantage of this pouching process is that the non-woven loop material can either have a plastic backing or be without a plastic backing because weld sealing jaws 864, 868 and 869 are used. This is because weld sealing jaws heat the material sufficiently long so that the binder in non-woven loop material seals with other plastic sheets. The benefit to using loop material without plastic backing, is that the pouch is breathable and the calender roll step of FIGS. 2 and 2A is eliminated.

Figure 27A:
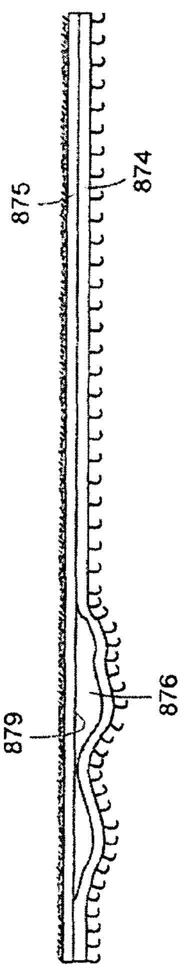
FIG. 27A is a side view of the wrapping shown in FIG. 27.
Figure 27:
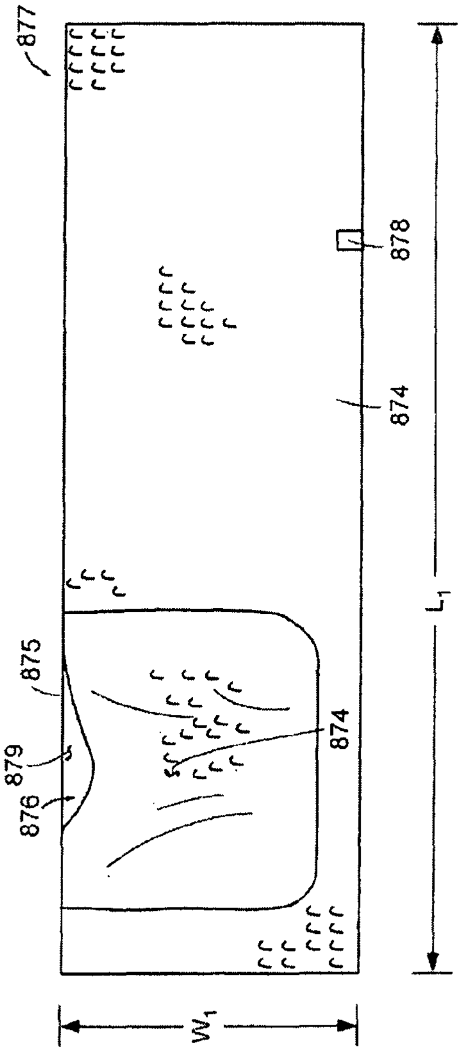
FIG. 27 is a plan view of a wrapping of another construction.

Another wrapping embodiment with width $W_1$ and length $L_1$ is illustrated in FIGS. 27 and 27A. This design provides a way to create a finished wrapping 877 with a pouch 876 directly from the calender roll process. Since the calender roll process of FIGS. 4 and 4A laminates the non-woven loop material 875 with a plastic backing of hooks 874, preventing this lamination in a select area creates the pouch 876. This is accomplished by printing an overprint varnish 879 on the non-woven loop material 875 before the calender process which prevents lamination in certain areas between the hook backing 874 and the non-woven loop material 875. Afterwards, the desired contents of the pouch 876 are manually inserted. One benefit to this embodiment is that the loop material 875 over the pouch 876 will not be sealed with resin so that it is porous and breathable and more comfortable against the skin.

Figure 27B:
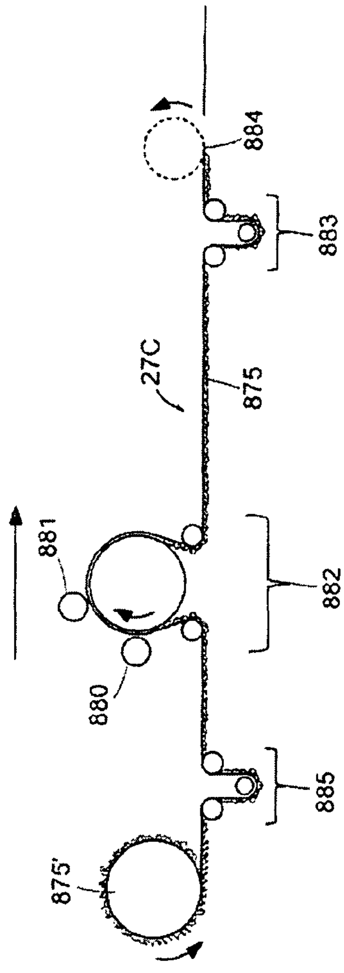
FIG. 27B is a side view of a flat bagging system for making the wrapping shown in FIG. 27.
Figure 27C:
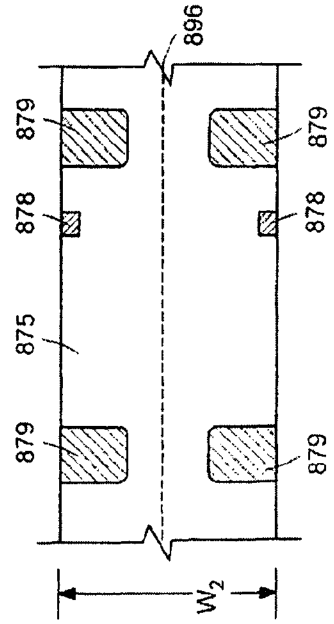
FIG. 27C is a plan view of the continuous web after printing in the system shown in FIG. 27B.

FIGS. 27B and 27C illustrate the process of printing the overprint varnish or "resin-resist" 879 on the backside of the loop. Supply roll 875' supplies a continuous sheet of non-woven loop material 875 of width $W_2$, which is twice $W_1$, such that this sheet continuously forms the material that is split downstream into two wrappings 877. A dancer mechanism 885 provides tension control and uniform feed of the loop material 875 going into a center impression, flexographic printing process for printing the varnish on the back 879 of the loop material. An alternative printing process is a sack-pressed flexographic printing process. The center impression printing process is preferred because its center drum is easily heated, which speeds up the drying process of the overprint varnish and potentially eliminates the need for a drying oven in the process. The center impression printing process has printing rolls 880 and 881. Printing roll 880 produces the resist print area 879. Printing roll 881 produces registration mark 878. Registration mark 878 is preferably black ink and used in the downstream calender roll process. The resulting sheet with print areas 878 and 879 is illustrated in FIG. 27C.

Figure 27D:
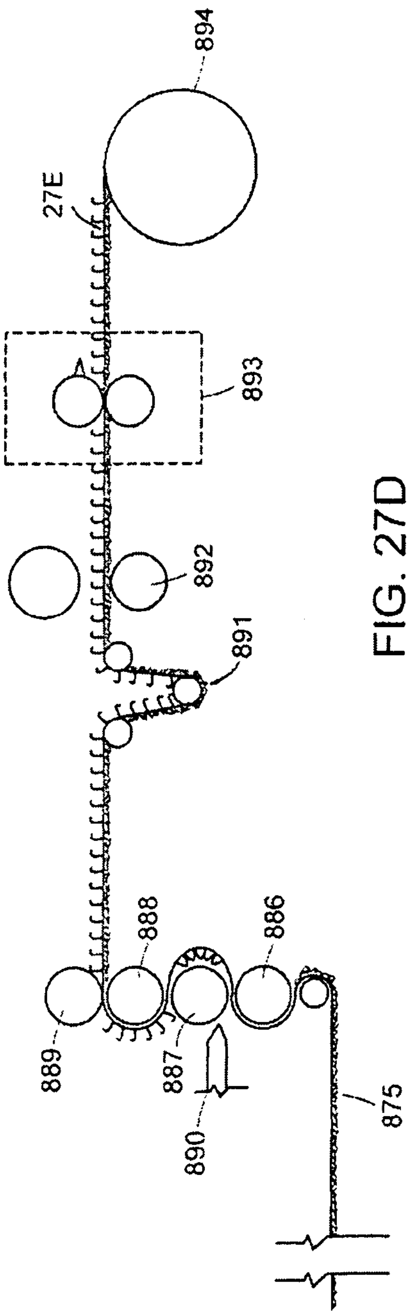
FIG. 27D is a side view of the flat bagging system for making the wrapping shown in FIG. 27.

Continuing along the process of FIG. 27B, another dancer mechanism 883 provides tension control of continuous sheet 875 to feed it into the calender roll process of FIG. 27D. An alternative method of production is to wind up this continuous sheet into finish roll 884. If this alternative method is used, then subsequently finish roll 884 feeds continuous sheet 875 into the calendar roll process of FIG. 27D.

After varnish resist 879 and ink 878 is printed on the continuous sheet 875, the sheet 875 enters the calendar stack consisting of rolls 886, 887, 888 and 889 as illustrated in FIG. 27D. Resin for the plastic backing with hooks 874 is extruded by extruder nozzle 890. Once the hooks 874 are formed on the printed loop material 875, the continuous sheet exits and goes into a dancer mechanism 891 to establish correct tension through the system and to provide some speed variation.

Slitting station 892 is just before the perforating station 893 and cuts the sheet with width $W_2$ along longitudinal line 896 into two sheets, each of width $W_1$. These two sheets are kept in place using tension control.

Figure 27E:
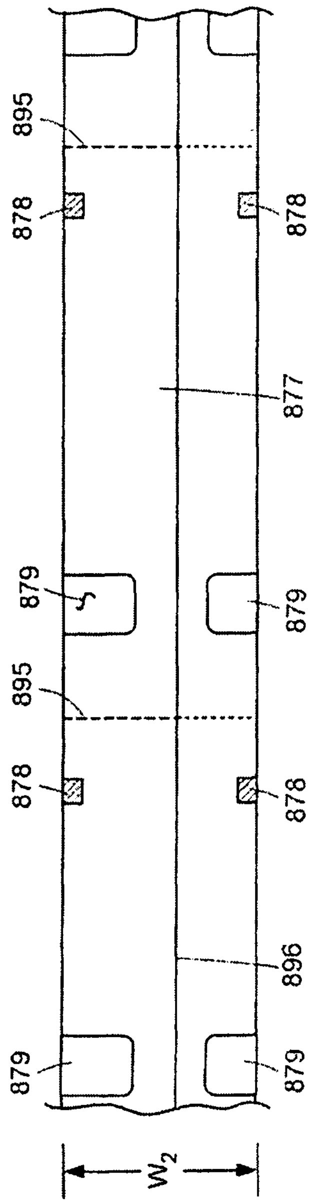
FIG. 27E is a plan view of the continuous web in the system shown in FIG. 27B.

Perforating station 893 puts perforation into the continuous sheet along transverse lines 895 so that a user can subsequently separate the individual wrappings 877 from each other. The continuous sheet with perforation is illustrated in FIG. 27E. This perforating station 893 is an episodic cutter. While cutting, it travels at the speed of the continuous sheet, once pass the cutting process, the rotation is sped up to catch up and in time with the next registration mark 878. Perforation station 893 is either an episodic cam or a rotary index cutter, where a servo drive is doing the accelerating and decelerating. Most importantly, the cutter 893, when engaged with a continuous sheet, runs at the same speed as the film so that it does not tear or otherwise slow down the continuous sheet. The registration mark triggers the perforating process. The individual perforations are sized correctly and in enough numbers so that the perforations still hold the continuous sheet together but enough fibers and film have been cut so that individual wrappings 877 can be ripped from the continuous sheet without propagating tears within each wrapping 877. Lastly, the continuous sheet with perforations or without perforations is rolled up into finish roll 894.

As an alternative, perforating station 893 could be removed and no perforations are put into the continuous sheet. In this case, the wrappings 877 are separated from the continuous sheet by a manual cutting operation as the finish roll 894 is unrolled.

Figure 28:
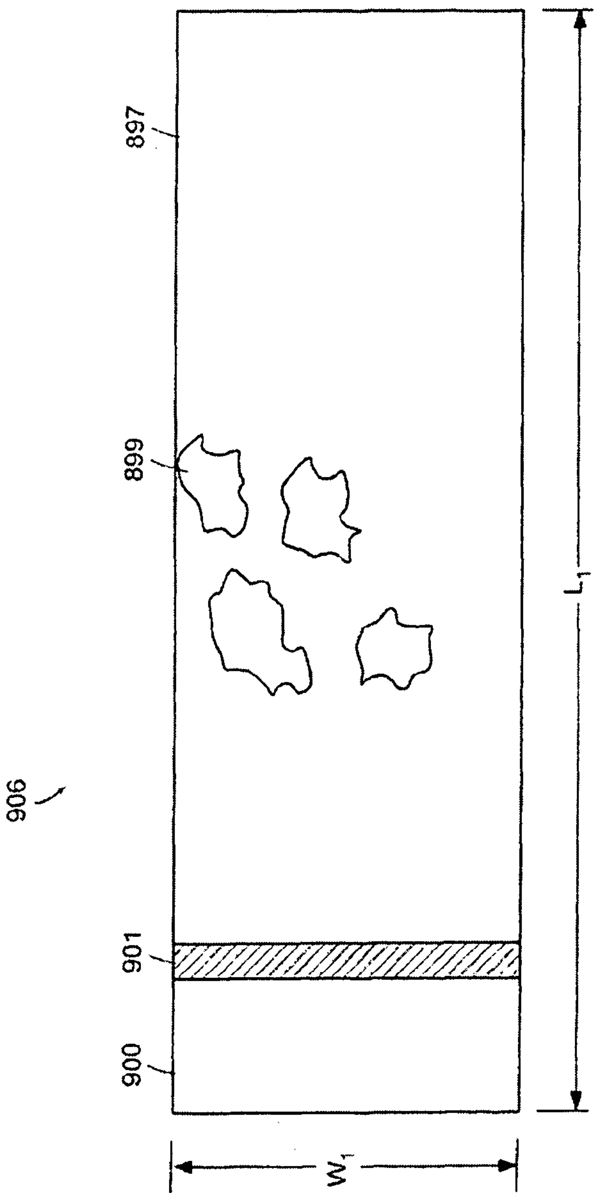
FIG. 28 is a plan view of a wrapping of another construction.
Figures 28A, 28B, 28C, 28D:
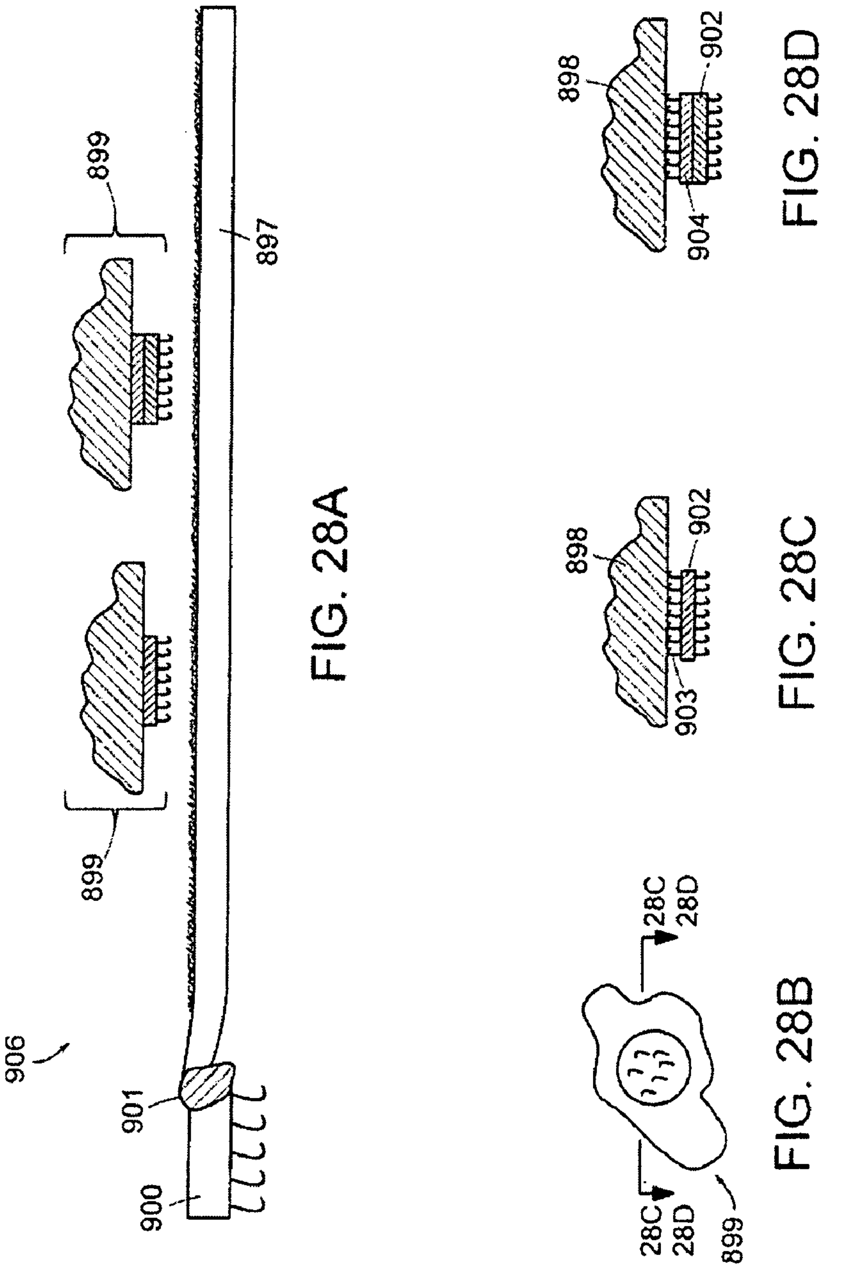
FIG. 28A is a side view of the wrapping shown in FIG. 28.
FIG. 28B is a plan view of an upside down medicinal patch used with the wrapping shown in FIG. 28.
FIG. 28C is a cross section view of one embodiment of the medicinal patch taken along line 28C-28C of FIG. 28B.
FIG. 28D is a cross section view of another embodiment of the medicinal patch taken along line 28D-28D of FIG. 28B.

Another wrapping embodiment, illustrated in FIGS. 28 and 28A, is a wrapping 906 whose functional area is multiple individual spot treatment areas 899 rather than a pouch with therapeutic contents. This wrapping 906, with length $L_1$ and width $W_1$, has non-woven loop material 897 and an edge strip with hooks 900. Hook strip 900 is joined to non-woven loop sheet 897 at weld 901 using a process similar to the flat bag, drag sealing process illustrated in FIG. 19A. FIG. 28B shows individual spot treatment areas 899 that are attached to the non-woven loop material 897 via pressure sensitive hooks 902. Spot treatment areas 899 are comprised of medicinal treatment area 898 and spot hook strips 902. In the preferred embodiment, spot hook strips 902 are joined to treatment area 898 using touch sensitive adhesive layer 903. In an alternate embodiment, depending on if the treatment material is hook engageable (such as gauze), spot hook strips 902 are joined to treatment area 898 using another hook strip 904. The hook to hook components 902, 904 can be either formed hook on hook using a calender roll process or they can be joined with glue or solvent or some other standard means.

Figure 29:
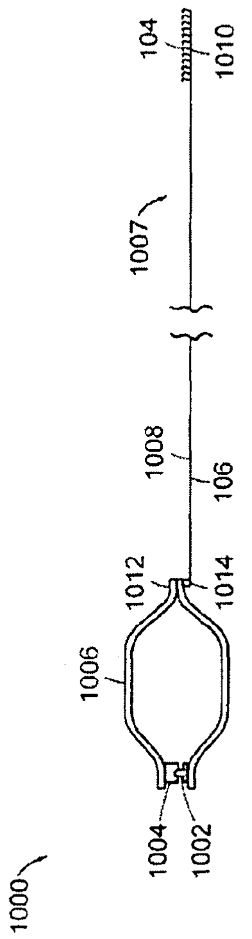
FIG. 29 is a cross section view of a self securing wrapping with a bag having a closure.
Figure 29A:
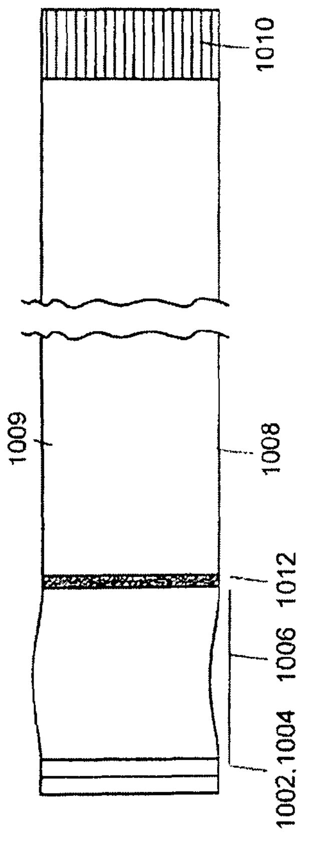
FIG. 29A is a plan view of the wrapping of FIG. 29.
Figure 29B:
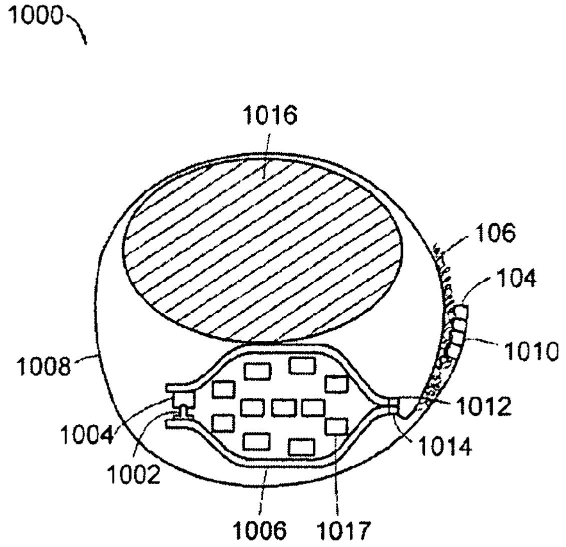
FIG. 29B is a diagrammatic, highly magnified cross-sectional view of the wrapping of FIG. 29 showing the flexible wrapping wrapped about an object, positioning the filled pouch with respect to it.

Referring to FIGS. 29 and 29A, a wrapping 1000 uses a rib 1002 fastener and a groove 1004 fastener to seal ice in a bag 1006 permanently joined to a composite material 1007 that includes a non-woven hook-engageable loop material 1008 having loops 104 (FIG. 1D) and a discrete band 1010 of hooks 4 (FIG. 1A) for wrapping around a body part and releasably self-attaching. An example of material 1008 is an elastomeric non-porous non-woven loop material available from Tredegar Film Products of Richmond, Va. Material 1008 can also be inelastic. FIG. 29B illustrates how wrapping 1000 can be used to hold a cold pack against an irregularly shaped body part 1016 representing a knee, an ankle, a wrist, and other body parts. Bag 1006 holds ice 1017 and material 1008 is wrapped around bag 1006 so that hooks 4 of band 1010 releasably engage with loops 104 on material 1008. The tension of wrapped material 1008 held in place by the engagement of loops 6 with hooks 4 holds bag 1006 tightly against body part 1016 for cold therapy. Since loops 6 are along the entire length of material 1008, a user can stretch the wrapping 1000 to different lengths depending on the size of body part 1016 and the user's comfort level. The rib 1002 and groove 1004 fasteners can be configured to be water tight when engaged to prevent the bag 1006, when heated from contact with body part 1016 and ice 1017 subsequently melts, from leaking water.

Weld 1012 joins bag 1006 to non-woven loop material 1008. Non-woven loop material 1008 with hook band 1010 is made with weld bead 1014. Hook band 1010 is formed in the machine direction from an extruded band of resin laminated in situ directly to the surface of material 1008, and molded to form hooks or hook preforms by mold cavities in the molding roll. Weld bead 1014 is formed at the same time in the machine direction from an extruded band of resin laminated in situ directly to the surface of material 1008, and molded into weld bead 1014 by a mold cavity in the molding roll. Wrapping 1000 is then made by welding a plastic bag with rib and groove fasteners to composite material 1007 at weld bead 1014. Wrapping 1000 can also be made with a folded plastic sheet having continuous rib and groove fastener strips in a continuous process using flat bag making machinery.

Figure 30B:
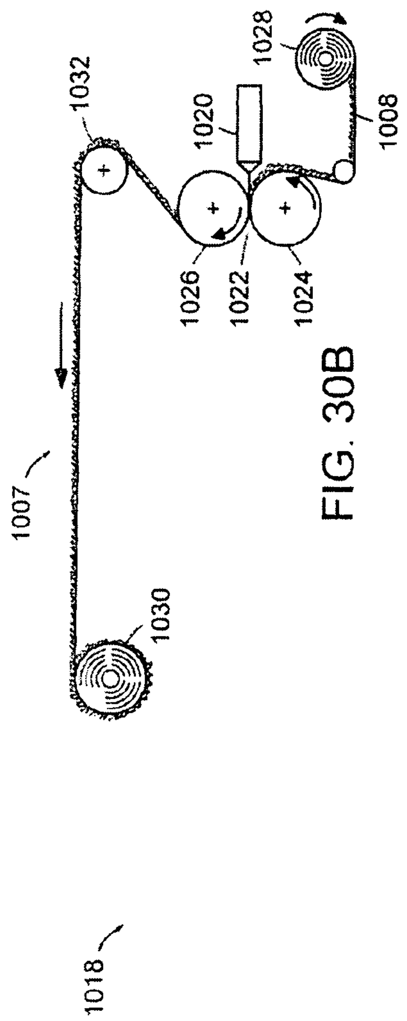
FIG. 30 is a diagrammatic plan view.
FIG. 30A is a cross section view, and FIG. 30B a diagrammatic end view, of a calender-forming-and-uniting machine producing a continuous composite, flexible web material from which wrappings with bags are formed.
Figure 30:
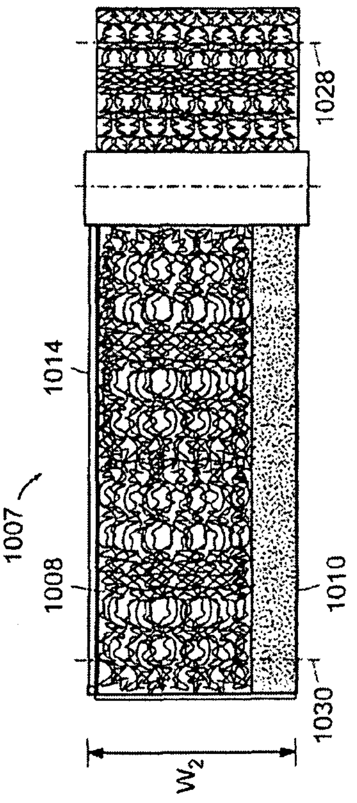
Figure 30A:

An apparatus 1018 and continuous process for making composite material 1007 is described with reference to FIGS. 30, 30A and 30B. Extruder 1020 provides to the nip 1022 a molten strip of the resin of width corresponding to the width of the desired band 1010 of molded hooks 4 as described previously with reference to FIGS. 3 and 3A. Completion of the in situ lamination is achieved by the pressure of the calender nip 1022 formed by pressure roll 1024 and mold roll 1026. Resin of a band of resin applied by extruder 1020 enters mold cavities in mold roll 1026, forming hook band 1010 that includes hooks 102 or hook preforms molded integrally with a base resin layer that is in situ laminated to the loop web by the action of the calendar nip 1022. At the same time, resin of another band of resin applied by extruder 1020 enters mold cavities in mold roll 1026, forming weld bead 1014 that is in situ laminated to the loop web 1008 by the action of the calendar nip 1022. After cooling, the finished wrapping material 1007 is removed from mold roll 1026 and rolled up in supply roll 1030, in which form the finished composite material 1007 is delivered to a wrapping forming machine.

Figure 31:
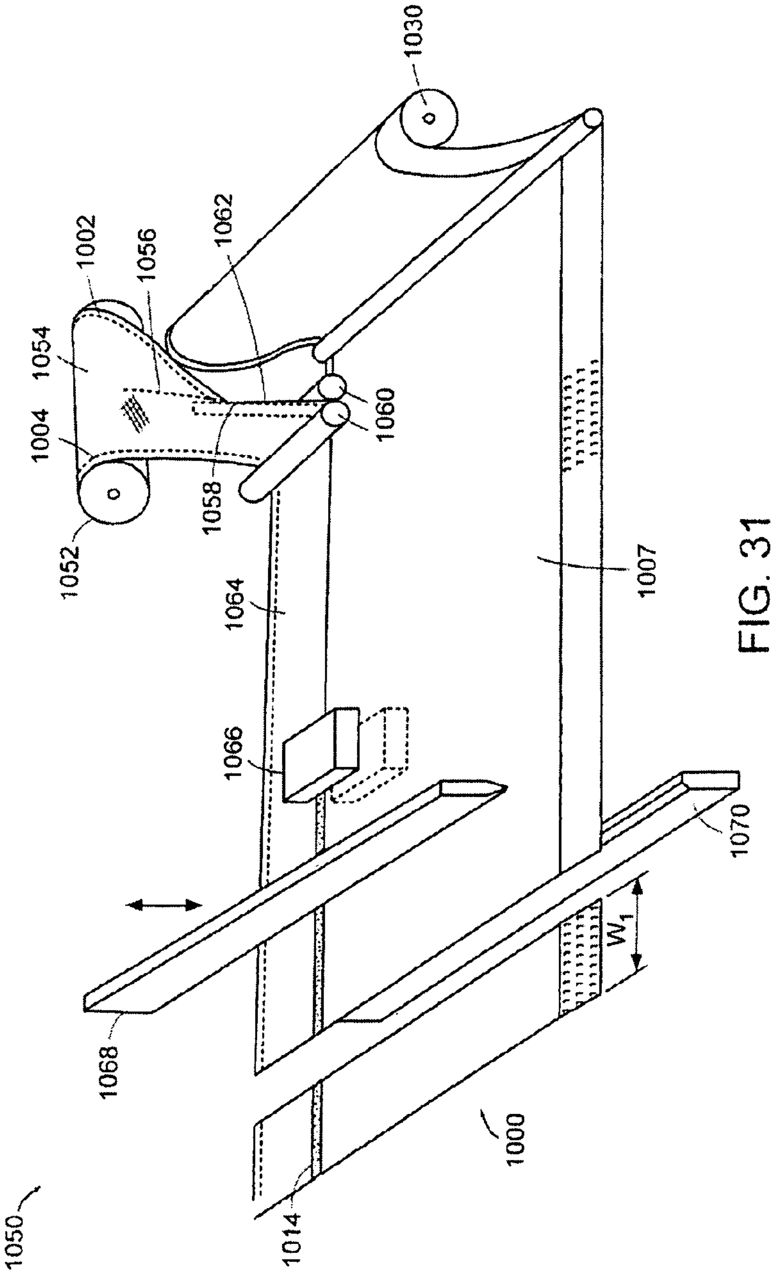
FIG. 31 is a perspective view of a flat bag making machine for making the wrappings of FIG. 29.

FIG. 31 illustrates a machine 1050 and method for making the wrapping 1000 described above. Plastic film 1054 is supplied as a roll 1052 with rib 1002 and groove 1004 fasteners welded previously to or integrally formed with the film 1054 using techniques such as extrusion. Roll 1052 of continuous plastic film 1054 is positioned such that a fold in plastic film 1054 is managed at a center fold line 1056. A folding bar or board 1058 is provided. Rollers 1060 pinch the fold 1062 just after the fold plate or folding board 1058 creates the center fold 1056. Folded sheet 1064 enters into the flat bag sealing machine 1050 on top of non-woven loop material 1008 with hook strip 1010 and weld bead 1014 to form the wrapping 1000. Typical flat bag-sealing machines of this type are available from Ro-An Industries Corp of Middle Village, N.Y. The Ro-An Industries style bag sealing machine 1050 is illustrated where the web is intermittently positioned into a tooling station. Roll 1030 positions the non-woven loop material 1008 with hook strip 1010 and weld bead 1014 into the bag sealing machine such that fold 1062 is laid on top of weld bead 1014, and then the weld bead 1014 and fold 1062 are positioned under weld sealing station 1066. Weld sealing station 1066 permanently joins folded plastic sheet 1054 and composite material 1007 using weld bead 1014.

Moving towards the left, heated seal bar 1068 simultaneously seals edges of bag 1006 using radiant heat and cuts the web in the cross machine direction against anvil roller 1070. In the process illustrated in FIG. 31, the web is intermittently advanced, so that at each advance, there is a period within the process where the device 1068 acts on the web. The repeat length $W_1$ defines the width $W_1$ of the strap and is determined by the stroke of the film advance. As in a previous example illustrated in FIG. 20F, particularly wide sheets 1007 may be folded for processing.

Another example of flat bag-sealing machines is available from GN Packaging Industries of Mississauga, Ontario, Canada. Using the GN style of bag sealing machine, wrapping 1000 can be manufactured in a similar way to the Ro-An style bag sealing machine except that the cross machine edge of bag 1006 is sealed first by a weld sealing station and then an unheated knife edge cuts the edge against a flat anvil.

In another example of the process illustrated in FIG. 31, the rib 1002 and groove 1004 fasteners are engaged together and then positioned in between the two folded sides of plastic film 1054 as plastic film 1054 is center folded upon entering the machine 1050. This can be done by continuously sliding an engaged rib 1002 and groove 1004 fastener strip into rollers 1060 in between the two folded sides of plastic film 1054. Moving to the left, the engaged rib 1002 and groove 1004 fasteners are welded to the two folded sides of plastic film 1054 using top and bottom heat sealers. In a related example, the plastic film 1054 can be manufactured as a tube with one end slit to form a pre-folded plastic film. In this example, the two edges of the plastic film 1054 are separated to enable entry of the engaged rib 1002 and groove 1004 fasteners.

In still another example, hook and loop fasteners can replace the rib 1002 and groove 1004 fasteners to make another type of wrapping. Such a wrapping can be manufactured by welding on a hook strip and a non-woven loop strip to opposite edges of plastic film 1054 prior to entering the machine 1050. In this example, bag 1006, closed with hooks and loops, is not necessarily water tight but for certain applications there is no problem with some leakage of water from a cold pack. In these cases, the cold therapy is improved by the spillage of water since thermal heat transfer between irregular body part 1016 and bag 1006 is improved with an interface of water.

Figure 32:
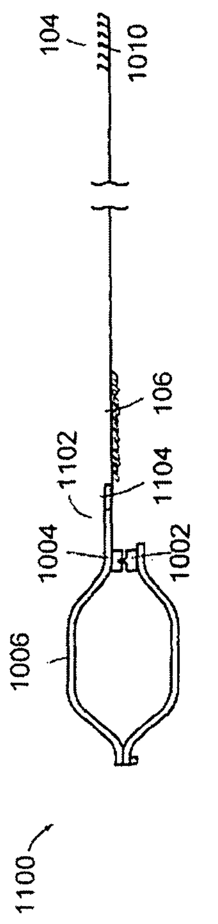
FIG. 32 is a cross section view of a self securing wrapping with a bag having a closure.
Figure 32A:
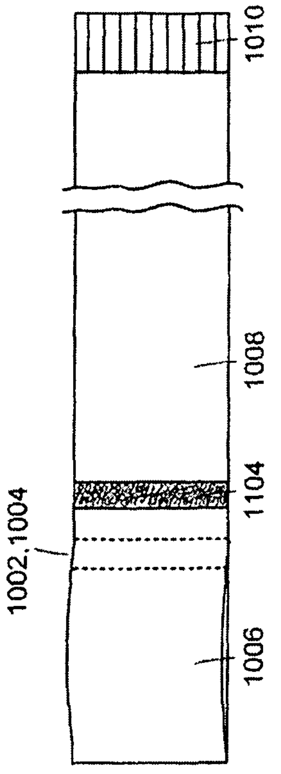
FIG. 32A is a plan view of the wrapping of FIG. 32.
Figure 32B:
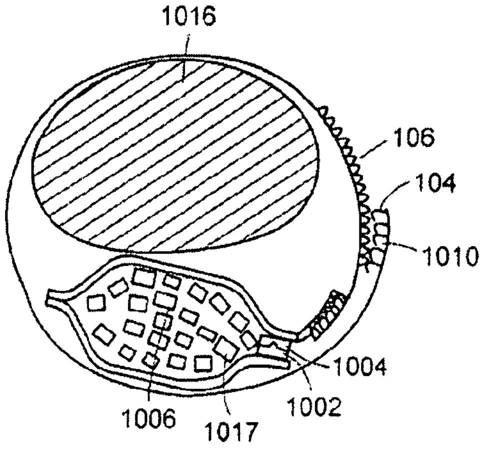
FIG. 32B is a diagrammatic, highly magnified cross-sectional view of the wrapping of FIG. 32 showing the flexible wrapping wrapped about an object, positioning the filled pouch with respect to it.

Referring to FIGS. 32 and 32A, a variation of wrapping 1000 is wrapping 1100. In this variation, bag 1006 is formed using a j-fold such that a lip 1102 extends past groove 1004 and the opening of bag 1006 with rib 1102 and groove 1004 fasteners faces inside wrapping 1100 rather than outside the wrapping as with wrapping 1000. In some applications, facing the opening of bag 1006 to the inside of the wrapping is advantageous because the weight of contents 1017 does not press against the opening of bag 1006 when a user holds wrapping 1100 by the section with hooks 1010. A weld 1104 permanently joins composite material 1007 to lip 1102. FIG. 32B illustrates how wrapping 1100 can be used to hold a cold pack against the irregularly shaped body part 1016 representing a knee, an ankle, a wrist, and other body parts. Bag 1006 holds ice 1017 and material 1008 is wrapped around bag 1006 so that hooks 4 of band 1010 releasably engage with loops 6 on material 1008 similarly to wrapping 1000.

Figure 33:
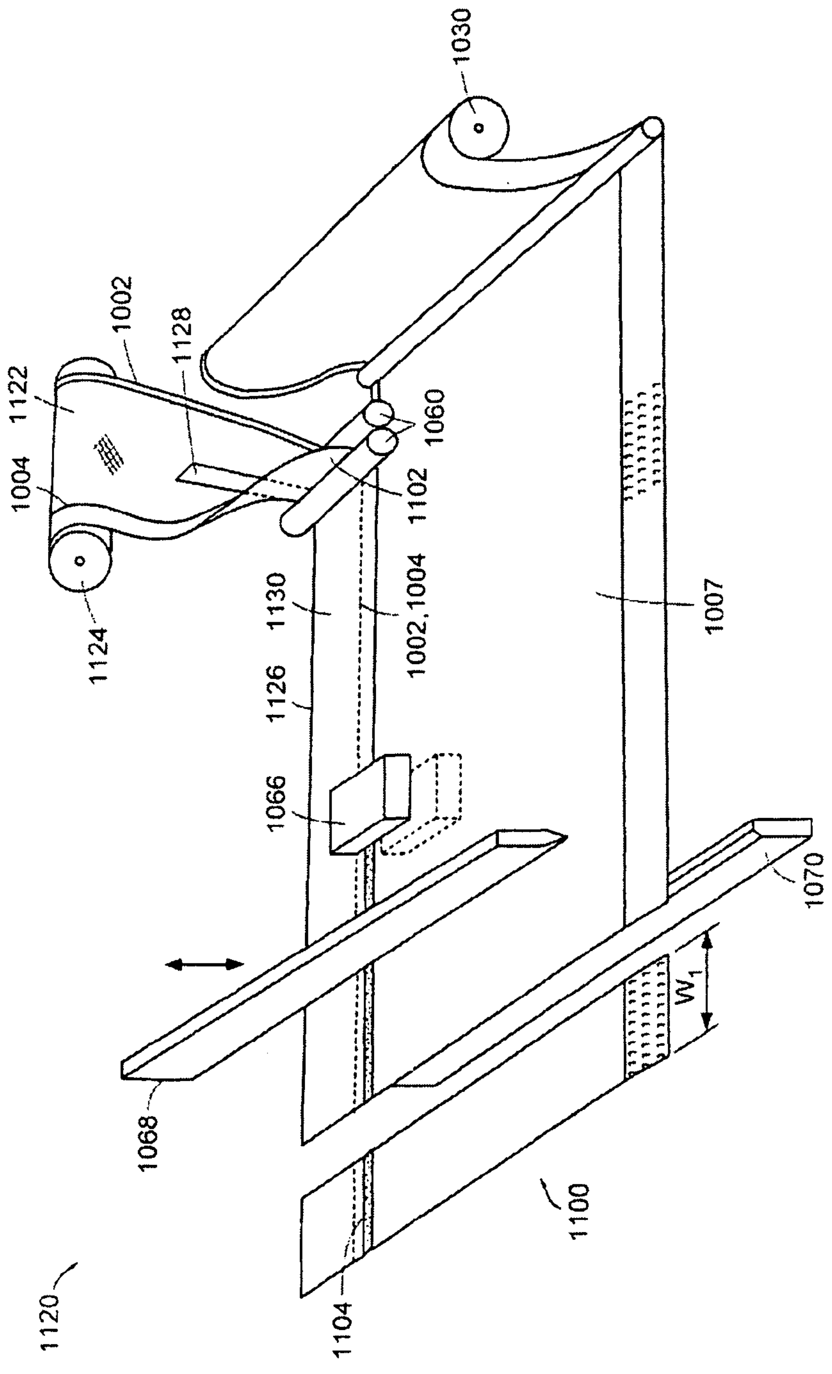
FIG. 33 is a perspective view of a flat bag making machine for making the wrappings of FIG. 32.

Similarly to wrapping 1000, wrapping 1100 can also be made with a folded plastic sheet having continuous rib and groove fastener strips in a continuous process using flat bag making machinery. FIG. 33 illustrates a machine 1120 and method for making the wrapping 1100 described above. Plastic film 1122 is supplied as a roll 1124 with rib 1002 and groove 1004 fasteners previously welded to or integrally formed with the film 1122. Roll 1124 of continuous plastic film 1122 is positioned such that a fold is managed at a j-fold 1126. A folding bar or board 1128 is provided. Rollers 1060 pinch the j-fold 1126 just after the fold plate or folding board 1128 creates the j-fold 1126. Folded sheet 1130 enters into a flat bag sealing machine on top of non-woven loop material 1008 with hook strip 1010 and weld bead 1014 to form the wrapping 1100. Roll 1030 positions the non-woven loop material 1008 with hook strip 1010 and weld bead 1014 into the bag sealing machine such that lip 1102 is laid on top of weld bead 1014, and then the weld bead 1014 and lip 1102 are positioned under weld sealing station 1066. Weld sealing station 1066 permanently joins folded plastic sheet 1130 and composite material 1007 using weld bead 1014.

Moving towards the left, upper heated seal bar 1068 again simultaneously seals edges of bag 1006 using radiant heat and cuts the web against lower anvil roller 1070. In the process illustrated in FIG. 33, the web is intermittently advanced, so that at each advance, there is a period within the process where the device 1068 acts on the web. The repeat length $W_1$ defines the width $W_1$ of the strap and is determined by the stroke of the film advance. As in a previous example illustrated in FIG. 20F, particularly wide sheets 1007 may be folded for processing.

The variations of the process of FIG. 31 described above similarly apply to the process of FIG. 33. Thus, a GN style machine can be substituted for the machine illustrated in FIG. 33. Furthermore, the rib 1002 and groove 1004 fasteners can be welded in-line using machine 1120. Similarly, hook and loop fasteners can be substituted for the rib 1002 and groove 1004 fasteners for a non-water tight wrapping.

In another variation of the wrapping 1100 of FIG. 32, the wrapping 1100 can be made without the rib 1002 and groove 1004 fasteners such that bag 1006 has an open end at the lip 1102. In this variation, the contents of bag 1006 can include ice or a preformed, closed cold pack filled with cooling gel or chemicals that create an endothermic reaction when mixed. Such cooling gel is available from Kobayashi Healthcare of Wayne, Pa. These contents are kept inside bag 1006 by the engagement of hooks 4 with the loops 6 of material 1008 when wrapping 1100 is wrapped around body part 1016 (as illustrated in FIG. 32B).

In still another variation of the wrapping 1100 of FIG. 32, the wrapping 1100 is manufactured using the process illustrated in FIG. 33 except that sheet 1122 is folded such that lip 1102 is below the other side of J-fold 1126. In this variation the rib 1002 and groove 1004 fasteners are positioned on the other side of the lip 1102 such that rib 1002 is on the same surface as lip 1102.

Figure 34:
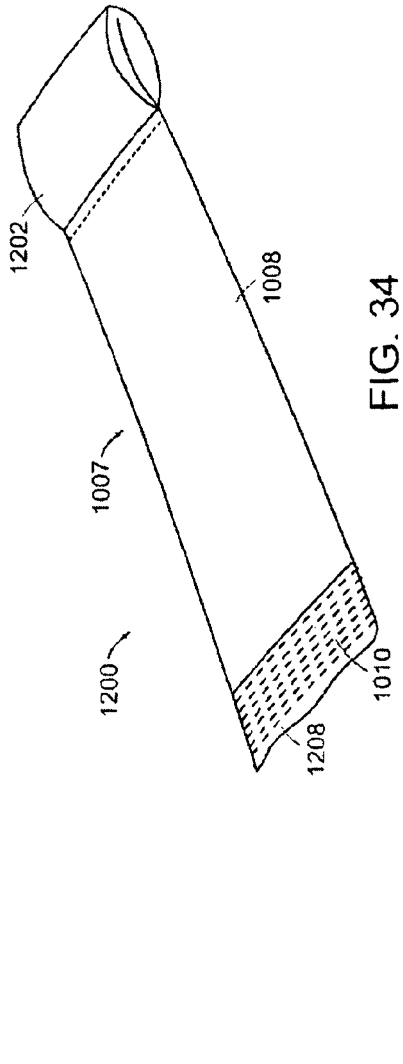
FIG. 34 is a perspective view of a wrapping with a wound care dressing.
Figure 34A:
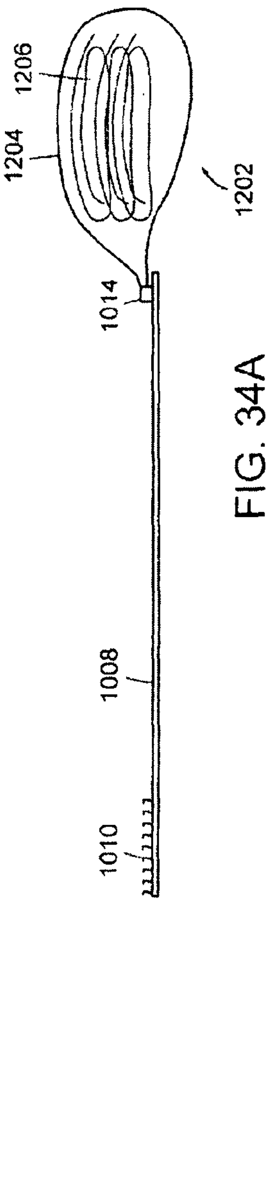
FIG. 34A is a cross section view of the wrapping of FIG. 34.

Referring to FIGS. 34 and 34A, a wound care wrapping 1200 enables a user to quickly secure a dressing pouch 1202 to a wound on a body part without using tape. The dressing pouch 1202 is permanently joined to the previously described composite material 1007. The user secures dressing 1202 to the wound by grasping an end 1208 and wrapping around the body part and releasably engaging hooks 4 with loops 6. Using a wound care wrapping without tape is useful because a paramedic does not require a third hand to apply the tape while a first hand holds the dressing on the wound and a second hand wraps the wrapping around. This is particularly important in accident or battlefield situations where a quick first aid response is required for wounds and the number of medical personnel is limited. Furthermore, applying the wound care dressing using this wrapping can result in pressure being applied directly from the dressing pouch 1202 towards the wound area due to the stretch of the wrapping around the body part. This pressure can result in close contact of dressing pouch 1202 with the wound that is useful to absorb blood loss from the wound. This pressure is particularly useful when the dressing pouch 1202 contains chemicals that are beneficial for stemming blood loss or for improving the healing of the wound because the chemicals need to come into contact with the wound area.

The dressing pouch 1202 includes a dressing sponge cloth 1204 wrapped around a folded combine dressing 1206. Dressing sponge cloth 1204 is a multi-layer absorbent cloth designed for use on top of wounds and incisions. Dressing sponge cloth 1204 is covered with a fabric facing designed to resist entanglement with the wound as it heals. Dressing sponge cloth 1204 is available as Topper® dressing sponge from Johnson & Johnson of New Brunswick, N.J. Combine dressing 1206 is an absorbent secondary dressing for use with moderate to heavy draining wounds. Combine dressing 1206 is available as Surgipad® combine dressing from Johnson & Johnson of New Brunswick, N.J. Dressing sponge cloth 1204 and combine dressing 1206 can be coated with blood clotting agents and other medicinal agents for improving the healing of the wound being treated. Following common practice, combine dressing 1206 is folded up into a rectangular package and enclosed by dressing sponge cloth 1204 to form dressing pouch 1202. The edges of dressing sponge cloth 1204 are folded into the dressing to have a clean rectangular dressing package without exposed cloth edges that could become engaged in a wound.

Dressing pouch 1202 is permanently joined to the composite material 1007 by welding dressing sponge to weld bead 1014. This welding occurs by positioning the edge of dressing pouch 1202 (dressing sponge 1204) over weld bead 1014 and heating the edge. The plastic in weld bead 1014 melts and flows into the fibers of the edge of dressing sponge 1204. After cooling, the plastic forms a bond between dressing sponge 1204 and material 1008. Composite material 1007 is manufactured using the process illustrated in FIGS. 30-30B. In one example, dressing 1202 can be preformed and then welded using a hand heater to individual wrappings cut from a continuous length of composite material 1007.

Figure 35:
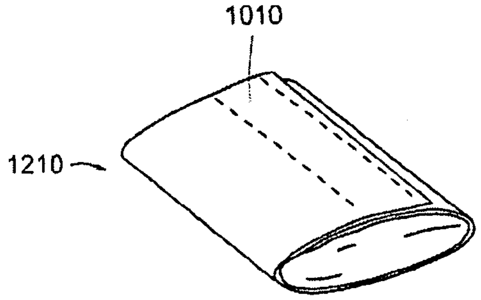
FIG. 35 is a perspective view of the wrapping of FIG. 34 folded up for storage.
Figure 36A:
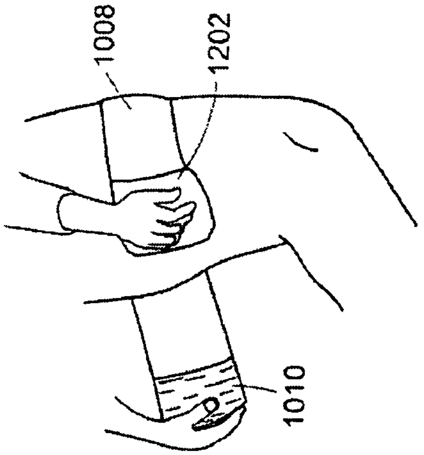
FIGS. 36, 36A, 36B and 36C are views of steps in the use of the wound care wrapping of FIG. 34 to bandage a wound on an inner thigh.
Figure 36C:
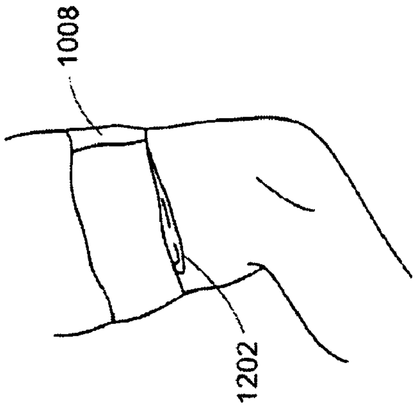
Figure 36:
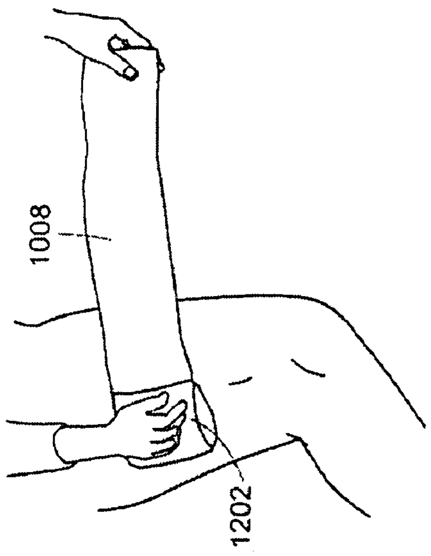
Figure 36B:
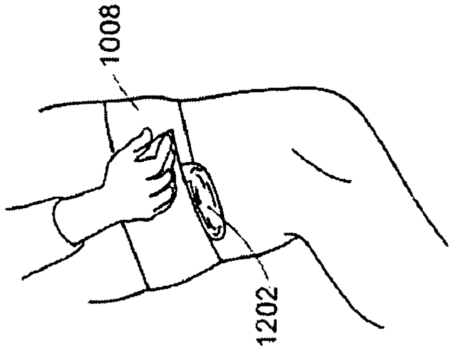

As illustrated in FIG. 35, the wound care wrapping 1200 can be wrapped together for storage by engaging hooks 4 in band 1010 with loops 6 in material 1008 for convenient storage in a sterile package 1210. After opening the sterile package 1210, a paramedic unwinds the wrapping 1200 by peeling hooks 4 in band 1010 away from loops 6 of material 1008, holding the hook band 1010, and letting the weight of dressing pouch 1202 unwind the wrapping 1200, or by grasping the exposed end of the wrapping and throwing the dressing to disengage the fastening elements and uncoil the wrapping in one quick motion. FIGS. 36-36C sequentially illustrate the use of wound care wrapping 1200 to bandage a wound on an inner thigh, using only two hands. First, the paramedic holds the dressing 1202 against the wound with one hand and extends material 1008 with the other hand (FIG. 36). Next, the paramedic wraps the material 1008 around the leg bringing the hook band 1010 towards the dressing 1202 while applying tension to material 1008 (FIG. 36A). Next, while maintaining tension in the stretched material, the paramedic attaches hooks 4 in band 1010 to loops 6 (FIG. 36B). The dressing pouch 1202 is now securely fastened to the wound, as illustrated in FIG. 36C, the thickness of dressing pouch 1202 causing localized pressure against the wound to stop bleeding. Subsequently, when the dressing pouch 1202 needs to be changed, the paramedic simply peels hooks 4 in band 1010 from loops 6 of material 1008 to release the wrapping 1200 and unwinds the wrapping 1200 away from the body part.

Several of the above-described constructions can be fashioned with minimal material costs and weight. In one example, a wrap of was formed of a substrate of high density polyethylene (HDPE) with an overall area of 6 inches (15 centimeters) by 34 inches (86 centimeters), provided with suitable hook and loop components, and still weighed only about 0.48 ounces (15 grams) with nothing in its pouch. Thus, fully configured wraps with weight-to-area ratios of less than about 150 grams per square meter, and correspondingly low material and disposal costs, are readily obtainable with the methods described above.

A number of embodiments of the invention have been described. Nevertheless, it will be understood that various modifications may be made without departing from the spirit and scope of the invention.

What is claimed is:

1. A medical wrap comprising a flexible, sheet-form substrate carrying a field of fibers exposed on one side thereof for engagement by fastener elements, and an array of fastener elements extending from a side of the substrate opposite the exposed fibers, the fastener elements each having a respective stem extending from and formed integrally with a film of resin disposed in a band across the substrate and encapsulating surface features of the substrate, the fastener elements constructed to snag the exposed fibers when the substrate is wrapped about the living tissue in an overlapping manner, to secure the wrap about the tissue; wherein the wrap defines a pouch in a discrete medical function delivery region adapted to be placed against living tissue to provide a desired medical effect, wherein the fastener elements and field of fibers are configured to enable removal of the wrap from the tissue by application of a peeling force of less than about 0.2 pounds of force per transverse inch of engaged width of the engaged fastener elements, to limit tissue trauma during wrap removal.

2. The medical wrap of claim 1 wherein the function delivery region is disposed at one end of the substrate.

3. The medical wrap of claim 1 contained in a sealed package with the substrate wrapped about the end at which the pouch is disposed, with the fastener elements releasably snagging fibers of the substrate to hold the substrate in a wrapped condition.

4. The medical wrap of claim 1 wherein the function delivery region comprises a wound covering.

5. The medical wrap of claim 4 wherein the pouch contains a dressing sponge.

6. The medical wrap of claim 4 wherein the pouch contains an absorbent material.

7. The medical wrap of claim 6 wherein the absorbent material comprises a combine dressing.

8. The medical wrap of claim 1 wherein the pouch contains a material substantially colder than normal human body temperature, for removing heat from human tissue.

9. The medical wrap of claim 1 wherein the pouch contains a material substantially warmer than normal human body temperature, for heating human tissue.

10. The medical wrap of claim 1 wherein the wrap is constructed to apply pressure against the tissue when the substrate is wrapped about the tissue and over the pouch under tension.

11. The medical wrap of claim 1 wherein the fastener elements are disposed in a discrete region adjacent an end of the substrate.

12. The medical wrap of claim 11 wherein the fastener elements are disposed adjacent an end of the substrate furthest from the function delivery region.

13. The medical wrap of claim 12 wherein the substrate comprises a non-fastening, graspable end region extending beyond the array of fastener elements.

14. The medical wrap of claim 1 wherein the substrate is resiliently stretchable in a direction extending between the function delivery region and the array of fastener elements.

15. The medical wrap of claim 1 of a length sized to enable wrapping the wrap about an extremity, torso, or head of a human being or animal in an overlapped condition.

16. The medical wrap of claim 1 wherein the pouch contains a functional agent in an inactivated state.

17. The medical wrap of claim 16 wherein the functional agent comprises unmixed ingredients that, when activated by mixing, generate an endothermic reaction.

18. The medical wrap of claim 16 wherein the functional agent comprises an ingredient that, when activated by exposure to air, generates an exothermic reaction.

19. The medical wrap of claim 1 wherein the peeling force is less than about 0.1 pounds of force per transverse inch of engaged width.

20. A medical wrap comprising a flexible, sheet-form substrate carrying a field of fibers exposed on one side thereof for engagement by fastener elements; and an array of fastener elements extending from a side of the substrate opposite the exposed fibers, the fastener elements each having a respective stem extending integrally with a film of resin disposed in a band across the substrate and encapsulating surface features of the substrate, the fastener elements constructed to snag the exposed fibers when the substrate is wrapped about living tissue in an overlapping manner, to secure the wrap about the tissue; wherein the fastener elements and field of fibers are configured to enable removal of the wrap from the tissue by application of a peeling force of less than about 0.2 pounds of force per transverse inch of engaged width of the engaged fastener elements, to limit tissue trauma during wrap removal.

21. The medical wrap of claim 20 wherein the peeling force is less than about 0.1 pounds of force per transverse inch of engaged width.

22. The medical wrap of claim 20 comprising a wound covering.

23. The medical wrap of claim 22 containing a dressing sponge separated from the tissue by a permeable delivery region of the substrate.

24. The medical wrap of claim 22 wherein the wound covering comprises a fluid-permeable surface of a pouch containing an absorbent material.

25. The medical wrap of claim 24 wherein the absorbent material comprises a combine dressing.

26. The medical wrap of claim 20 containing a material substantially colder than normal human body temperature, for removing heat from the tissue.

27. The medical wrap of claim 20 containing a material substantially warmer than normal human body temperature, for heating the tissue.

28. The medical wrap of claim 20 wherein the wrap is constructed to apply pressure against the tissue when the substrate is wrapped about the tissue and over the function delivery region under tension.

29. The medical wrap of claim 20 wherein the substrate is resiliently stretchable in a direction extending between the function delivery region and the array of fastener elements.

30. The medical wrap of claim 20 containing a functional agent in an inactivated state.

31. The medical wrap of claim 30 wherein the functional agent comprises unmixed ingredients that, when activated by mixing, generate an endothermic reaction.

32. The medical wrap of claim 30 wherein the functional agent comprises an ingredient that, when activated by exposure to air, generates an exothermic reaction.

33. The medical wrap of claim 20 wherein the fastener elements and field of fibers are configured to resist an applied shear load, along the wrap, of at least 1.0 pound per square inch of engaged fastener area.

34. The medical wrap of claim 20 having a total weight of less than about 150 grams per square meter of overall wrap area.

35. A thermic treatment wrap comprising a flexible, sheet-form substrate carrying both a field of fibers exposed on one side thereof for engagement by fastener elements, and an array of fastener elements extending from a side of the substrate opposite the exposed fibers adjacent one end of the substrate, the fastener elements each having a respective stem extending from and formed integrally with a film of resin disposed in a band across the substrate and encapsulating surface features of the substrate; the wrap defining a pouch containing a material activatable to initiate a thermic reaction, for transferring heat with respect to a patient about which the wrap is wrapped in overlapping manner, with the fastener elements engaging the fibers of the substrate to hold the pouch against the patient, wherein the fastener elements and field of fibers are configured to enable removal of the wrap from the tissue by application of a peeling force of less than about 0.2 pounds of force per transverse inch of engaged width of the engaged fastener elements, to limit tissue trauma during wrap removal.

36. The thermic treatment wrap of claim 35 wherein the activatable material produces an endothermic reaction when activated, for removing body heat.

37. The thermic treatment wrap of claim 35 wherein the activatable material produces an exothermic reaction when activated, for warming the patient.

38. The thermic treatment wrap of claim 35 wherein the pouch is disposed at one end of the substrate.

39. The thermic treatment wrap of claim 35 contained in a sealed package with the substrate wrapped about the pouch, with the fastener elements releasably snagging fibers of the substrate to hold the substrate in a wrapped condition.

40. The thermic treatment wrap of claim 35 wherein the substrate has a nominal width shorter than its length, and wherein the pouch is disposed substantially within the width of the substrate, such that the wrap effectively envelops the pouch when wrapped about the patient, to hold the pouch in place.

* * * * *

UNITED STATES PATENT AND TRADEMARK OFFICE

CERTIFICATE OF CORRECTION

PATENT NO. : 8,314,283 B2
APPLICATION NO. : 10/738847
DATED : November 20, 2012
INVENTOR(S) : Howard A. Kingsford et al.

It is certified that error appears in the above-identified patent and that said Letters Patent is hereby corrected as shown below:

In the Specifications:

Col. 1, line 6, delete “or” and insert --of--;

In the Claims:

Claim 20, Col. 43, line 30, after “extending” insert --from and formed--.

Signed and Sealed this
Thirtieth Day of April, 2013

Teresa Stanek Rea
*Acting Director of the United States Patent and Trademark Office*